United States Patent
Norris et al.

(10) Patent No.: US 6,740,744 B2
(45) Date of Patent: *May 25, 2004

(54) VMP-LIKE SEQUENCES OF PATHOGENIC BORRELIA

(75) Inventors: Steven J. Norris, Houston, TX (US); Jing-Ren Zhang, Delmar, NY (US); John M. Hardham, Gales Ferry, CT (US); Jerrilyn K. Howell, Houston, TX (US); Alan G. Barbour, Newport Beach, CA (US); George M. Weinstock, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/143,024

(22) Filed: Jul. 31, 2002

(65) Prior Publication Data

US 2003/0092903 A1 May 15, 2003

Related U.S. Application Data

(62) Division of application No. 09/125,619, filed on Jan. 27, 1999, now Pat. No. 6,437,116, which is a continuation of application No. PCT/US97/02952, filed on Feb. 20, 1997.
(60) Provisional application No. 60/012,028, filed on Feb. 21, 1996.

(51) Int. Cl.[7] .................. C07H 21/04; C07H 21/02; A61K 31/70; A61K 49/00; A61K 39/00
(52) U.S. Cl. ............. 536/23.1; 424/184.1; 424/185.1; 424/190.1; 424/192.1; 424/234.1; 435/4; 435/7.1; 435/7.2; 435/7.32; 436/501; 530/300; 530/350; 536/23.4; 536/23.7
(58) Field of Search ................... 424/184.1, 185.1, 424/190.1, 192.1, 234.1; 435/4, 7.1, 7.2, 7.32; 436/501; 530/300, 350; 536/23.1, 23.4, 23.7

(56) References Cited

U.S. PATENT DOCUMENTS

| | | | |
|---|---|---|---|
| 4,801,540 A | 1/1989 | Hiatt et al. | 435/411 |
| 5,155,022 A | 10/1992 | Naqui et al. | 435/7.32 |
| 5,178,859 A | 1/1993 | Simon et al. | 435/139.1 |
| 5,187,065 A | 2/1993 | Schutzer | 435/7.32 |
| 5,217,872 A | 6/1993 | Dorward et al. | 435/7.32 |
| 5,217,874 A | 6/1993 | Guadagno et al. | 435/28 |
| 5,246,844 A | 9/1993 | Norris et al. | 435/480 |
| 5,279,938 A | 1/1994 | Rosa | 435/6 |
| 5,283,175 A | 2/1994 | Weaver et al. | 435/6 |
| 5,304,718 A | 4/1994 | Ward et al. | 800/266 |
| 5,324,630 A | 6/1994 | LeFebvre et al. | 435/6 |
| 5,385,826 A | 1/1995 | Schell et al. | 435/7.32 |
| 5,434,077 A | 7/1995 | Simon et al. | 435/243 |
| 5,436,000 A | 7/1995 | Barbour et al. | 424/93.2 |
| 5,571,718 A | 11/1996 | Dunn et al. | 435/252.3 |
| 6,475,492 B1 | 11/2002 | Philipp et al. | 424/234.1 |
| 6,610,301 B1 | 8/2003 | Motz et al. | 424/190.1 |

FOREIGN PATENT DOCUMENTS

| | | | | |
|---|---|---|---|---|
| WO | WO 91/13630 | 9/1991 | | A61K/39/00 |

OTHER PUBLICATIONS

GenBank Accession No. AAC45733.
GenBank Accession No. AAB09432.
GenBank Accession No. AAB17737.
Balmelii and Piffatetti, "Analysis of the genetic polymorphism of *Borrelia burgdorferi* sensu lato by multilocus enzyme electrophoresis," *Int. J. Syst. Bacteriol.*, 46:167–172, 1996.
Barbour and Garon, "Linear plasmids of the bacterium *Borelia burdorferi* have covalently closed ends," *Science*, 237:409–411, 1987.
Barbour et al., "Structural analysis of the variable major proteins of *Borrelia hermsii*," *J. Exp. Med.*, 158:2127–2140, 1983.
Barbour et al., "Tandem insertion sequence–like elements define the expression site for variable antigen genes of *Borrelia hermsii*," *Infect. Immun.*, 59:390–397, 1991.
Barbour et al., "Variable antigen genes of the relapsing fever agent *Borrelia hermsii* are activated by promoter addition," *Mol. Microbiol.*, 5:489–493, 1991.
Barbour et al., "Variable major proteins of *Borrelia hermsii*," *J. Exp. Med.*, 156:1312–1324, 1982.
Barbour, "Immunochemical analysis of Lyme disease spirochetes," *Yale J. Biomed.*, 57:581–586, 1984.
Barbour, "Plasmid analysis of *Borrelia burgdorferi*, the Lyme disease agent," *J. Clin. Microbiol.*, 26(3):475–478, 1988.
Barstad et al., "Variable major proteins of *Borrelia hermsii*. Epitope mapping and partial sequence analysis of CNBr peptides," *J. Exp. Med.*, 161:1302–1314, 1985.
Benach et al., "A murine IgM monoclonal antibody binds an antigenic determinant in outer surface protein A, and immunodominant basic protein of the lyme disease spirochete," *The Journal of Immunology*, 140:265–272, 1988.
Berg et al., "The laboratory diagnosis of lyme disease," *Arch. Dermatol.*, 127:866–870, 1991.

(List continued on next page.)

*Primary Examiner*—Rodney P Swartz
(74) *Attorney, Agent, or Firm*—Fulbright & Jaworski LLP

(57) ABSTRACT

The present invention relates to DNA sequences encoding Vmp-like polypeptides of pathogenic Borrelia, the use of the DNA sequences in recombinant vectors to express polypeptides, the encoded amino acid sequences, application of the DNA and amino acid sequences to the production of polypeptides as antigens for immunoprophylaxis, immunotherapy, and immunodiagnosis. Also disclosed are the use of the nucleic acid sequences as probes or primers for the detection of organisms causing Lyme disease, relapsing fever, or related disorders, and kits designed to facilitate methods of using the described polypeptides, DNA segments and antibodies.

31 Claims, 12 Drawing Sheets

OTHER PUBLICATIONS

Figure 2A:
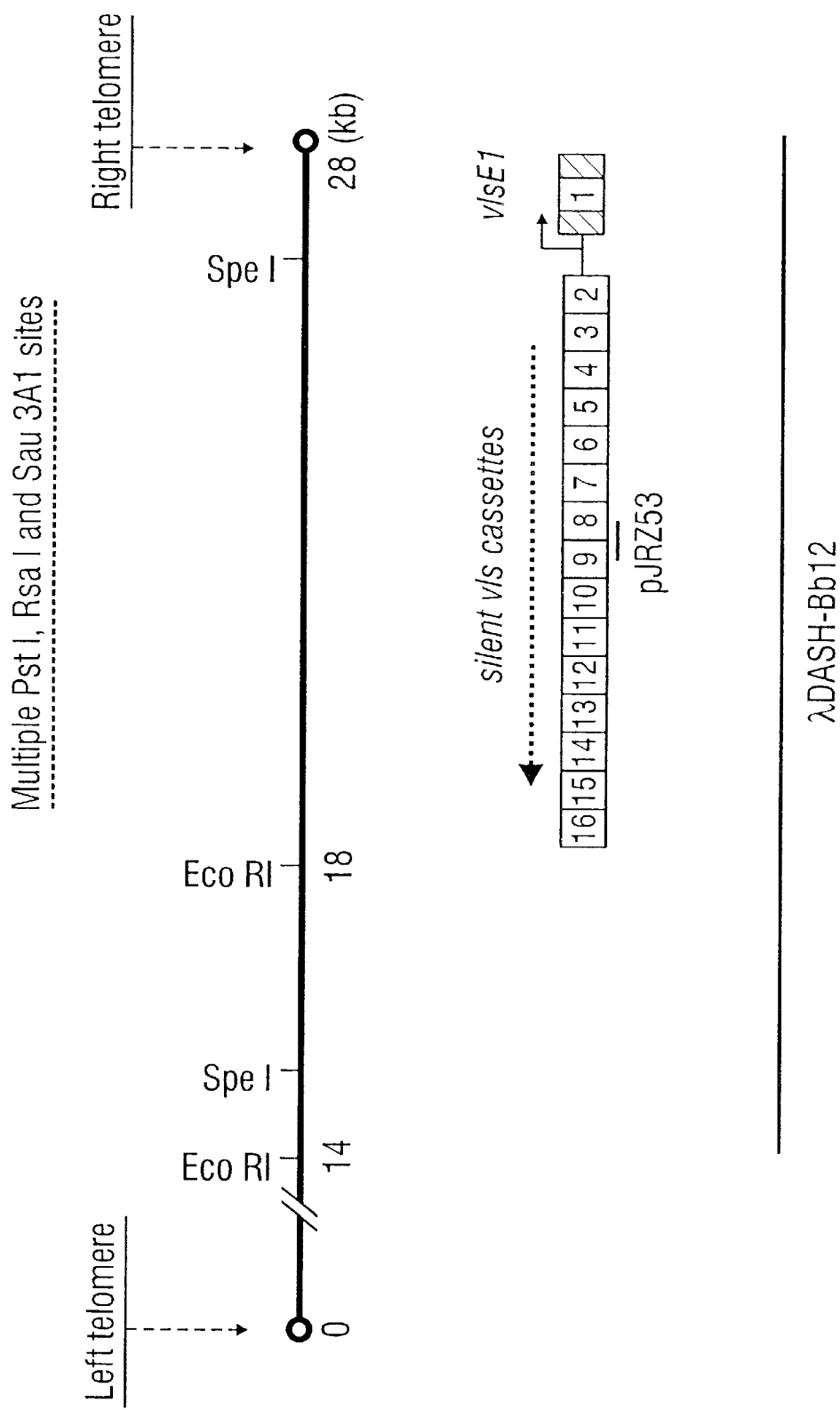

Borenstein et al., "Evidence for surface exposure of a 29kDa *Borrelia burgdorferi* antigen," *Abstracts of the Annual Meeting of American Soc. Microbiol.*, 90(0):46, Abstract B–116, 1990.

Brandt et al., "Immunogenic integral membrane proteins of *Borrelia burgdorferi* are lipoproteins," *Infect. Immun.*, 58(4):983–991, 1990.

Burman et al., "The variable antigens Vmp7 and Vmp21 of the relapsing fever bacterium *Borrelia hermsii* are structurally analogous to the VSG proteins of the African trypanosome," *Molecular Mocrobiology*, 4(10);1715–1726, 1990.

Carroll and Gheradini, "Membrane protein variations associated with in vitro passage of *Borrelia burgdorfei*," *Infect. Immun.*, 64:392–398, 1996.

Carter et al., "A family of surface–exposed proteins of 20 kilodaltons in the genus *Borrelia*," *Infect. Immun.*, 62:2792–2799, 1994.

Casjens et al., "Linear chromosomes of Lyme disease agent spirochetes: genetic diversity and conservation of gene order," *J. Bacteriol.*, 177:2769–2780, 1995.

Cluss and Boothby, "Thermoregulation of protein synthesis in *Borrelia burgdorferi*," *Infect. Immun.*, 58(4):1038–1042, 1990.

Cunningham et al., *Ann. NY Acad. Sci*, 539:376–378, 1988. Dialog Search Report.

Donelson, "Mechanisms of antigenic variation in *Borrelia hermsii* and African trypanosomes," *J. Biol. Chem.*, 270:7783–7786, 1995.

Fawcett et al., "Detection of antibodies to the recombinant p39 protein of *Borrelia burgdorferi* using enzyme immunoassay and immunoblotting," *J. Rheumatology*, 20(4):734–738, 1993.

Grodzicki and Steere, "Comparison of immunoblotting and indirect enzyme–linked immunosorbent assay using different antigen preparations for diagnosing early lyme disease," *J. Infect. Dis.*, 157(4):790–797, 1988.

Howe et al., "A single recombinant plasmid expressing two major outer surface proteins of the lyme disease spirochete," *Science*, 227:645–646, 1985.

Howe et al., "Organization of genes encoding two outer membrane proteins of the lyme disease agent *Borrelia burgdorferi* within a single transcriptional unit," *Infect. Immun.*, 54:207–212, 1986.

Hyde et al., "Detection of antigens in urine of mice and humans infected with *Borrelia burgdorferi*, etiologic agent of lyme disease," *Journal of Clinical Microbiology*, 27(1):58–61, 1989.

International Search Report dated Jan. 21, 1995.(PCT/US94/10729) (UTFH:195P).

International Search Report dated Jan. 26, 1993.(PCT/US92/09145) (UTFH:162P).

International Search Report dated Jul. 25, 1997 (PCT/US97/02952) (UTFH:234P).

Jiang et al., "Cross–antigenicity between the major surface proteins (ospA and ospB) and other proteins of *Borrelia burdorferi*," *J. Immun.*, 144(1):284–289, 1990.

Kalish, "Lyme Disease," *Infect. Arthritis*, 19(2):399–426, 1993.

Karlsson, "Western immunoblot and flagellum enzyme–linked immunosorbent assay for serodiagnosis of lyme borreliosis," *J. Clin. Microbiol.*, 28(9):2148–2150, 1990.

Kitten and Barbour, "Juxtaposition of expressed variable antigen genes with a conserved telomere in the bacterium *Borrelia hermsii*," *Proc. Natl. Acad. Sci. USA*, 87:6077–6081, 1990.

Kitten et al., "Intragenic recombination and a chimeric outer membrane protein in the relapsing fever agent *Borrelia hermsii*," *J. Bacteriol.*, 175(9):2516–2522, 1993.

LeFebvre et al., "Characterization of *Borrelia burgdorferi* isolates by restriction endonuclease analysis and DNA hybridization," *Journal of Clinical Microbiology*, 27(4):636–639, 1989.

Luft et al., Biochemical and immunological characterization of the surface proteins of *Borrelia burgdorferi*, *Infect. Immun.*, 57(11):3637–3645, 1989.

Margolis et al., "Homology between *Borrelia burgdorferi* OspC and members of the family of *Borrelia hermsii* variable major proteins," *Gene*, 143:105–110, 1994.

Moody et al., "Lyme borreliosis in laboratory animals: effect of host species and in vitro passage of *Borrelia burgdorferi*," *Am. J. Trop. Med. Hyg.*, 43(1):87–92, 1990.

Norris et al., "Comparison of protein and fatty acid profiles of low– and high–passage strains of *Borrelia burgdoreferi*," Annual Meeting American Soc. Microbiol., 90(0):103, Abstract D–135, 1990.

Norris et al., "High– and low–infectivity phenotypes of clonal populations of in vitro–cultured *Borrelia burgdorferi*," *Infect. Immun.*, 63:2206–2212, 1995.

Norris et al., "Low–passage–associated proteins of *Borrelia burgdoreferi* B31: characterization and molecular cloning of OspD, a surface–exposed, plasmid–encoded lipoprotein," *Infect. Immun.*, 60:4662–4672, 1992.

Persing et al., "Genetic stability of *Borrelia burgdorferi* recovered from chronically infected immunocompetent mice," *Infect. Immun.*, 62:3521–3527, 1994.

Plasterk et al., "Transposition of structural genes to an expression sequence on a linear plasmid causes antigenic variation in the Bacterium *Borrelia hermsii*," *Nature*, 318:257–263, 1985.

Restrepo and Barbour, "Antigen diversity in the bacterium *B. hermsii* through 'somatic' mutations in rearranged *vmp* genes," *Cell*, 78:867–876, 1994.

Restrepo et al., "Activation of a *vmp* pseudogene in *Borrelia hermsii*: and alternate mechanism of antigenic variation during relapsing fever," *Mol. Microbiol.*, 13:287–299, 1994.

Restrepo et al., "Subtelomeric expression regions of *Borrelia hermsii* linear plasmids are highly polymorphic," *Mol. Microbiol.*, 6:3299–3311, 1992.

Sadziene et al., "*Borrelia burgdorferi* mutant lacking osp: biological and immunological characterization," *Infection and Immunity*, 63(4):1573–1580, 1995.

Schutzer et al., "Sequestration of antibody to *Borrelia burgdorferi* in immune complexes in seronegative Lyme disease," *Lancet.*, 335:312–315, 1990.

Schwan and Simpson, "Factors influencing the antigenic reactivity of *Borrelia burgdorferi* the lyme disease spirochete," *Scand. J. Infect. Dis.*, 77:94–101, 1991.

Schwan et al., "Changes in antigenic reactivity of *Borrelia burgdorferi* the lyme disease spirochete, during persistent infection in mice," *Can. J. Microbiol.*, 37:450–454, 1991.

Scriba et al., "The 39–kilodalton protein of *Borrelia burgdorferi*: a target for bactericidal human monoclonal antibodies," *Infect. Immun.*, 61(10):4523–4526, 1993.

Simpson et al., "Reactivity of human lyme *borreliosis sera* with a 39–kilodalton antigen specific to *Borrelia burgdorferi*" *J. Clin. Microbiol.*, 28(6):1329–1337, 1990.

Simpson et al., "Antibody to a 39–kilodalton *Borrelia burgdorferi* antigen (P39) as a marker for infection in experimentally and naturally innoculated animals," *J. Clinical Microb.*, 29(2):236–243, 1991.

Steere, "Medical progress, Lyme disease," *New England J. Med.*, 321(9):586–596, 1989.

Stevenson et al., "Expression and gene sequence of outer surface protein C of *Borrelia burgdorferi* reisolated from chronically infected mice," *Infect. Immun.*, 62:3568–3571, 1994.

Szczepanski and Benach, "Lyme borreliosis: host responses to *Borrelia burgdorferi*," *Microb. Rev.*, 55(1):21–34, 1991.

Thiessen et al., "Evolution of the *Borrelia burgdorferi* outer surface protein OspC," *J. Bacteriol.*, 177:3036–3044, 1995.

Wallich et al., "The *Borrelia burgdorferi* flagellum–associated 41–kilodalton antigen (flagellin):molecular cloning, expression and amplification of the gene," *Infect. Immun.*, 58(6):1711–1719, 1990.

Wilske et al., "Antigenic variation and strain heterogenecity in Borrelia spp," *Res. Microbiol.*, 143:583–596, 1992.

Wise and Weaver, "Detection of the lyme disease bacterium, *Borrelia burgdorferi*, by using the polymerase chain reaction and a nonradioisotopic gene probe, "*Journal of Clinical Microbiology*, 29(7):1523–1526, 1991.

Written Opinion dated Mar. 10, 1998 (PCT/US97/02952) (UTFH:234P).

Zhang et al., "Antigenic variation in lyme disease borreliae by promiscuous recombination of VMP–like sequence cassettes," *Cell*, 89:275–285, 1997.

Liang et al., "An immunodominant conserved region within the variable domain of VlsE, the variable surface antigen of *Borrelia burgdorferi*," *J. Immunology*, 163:5566–5573, 1999.

Liang et al., "Characterization of a *Borrelia burgdorferi* VlsE invariable region useful in canine lyme disease serodiagnosis by enzyme–linked immunosorbent assay," *J. Clinical Microbiology*, 38(11):4160–4166, 2000.

Liang et al., "Sensitive and specific serodiagnosis of lyme disease by enzyme–linked immunosorbent assay with a peptide based on an immunodominant conserved region of *Borrelia burgdorferi* VlsE," *J. Clinical Microbiology*, 37(12):3990–3996, 1999.

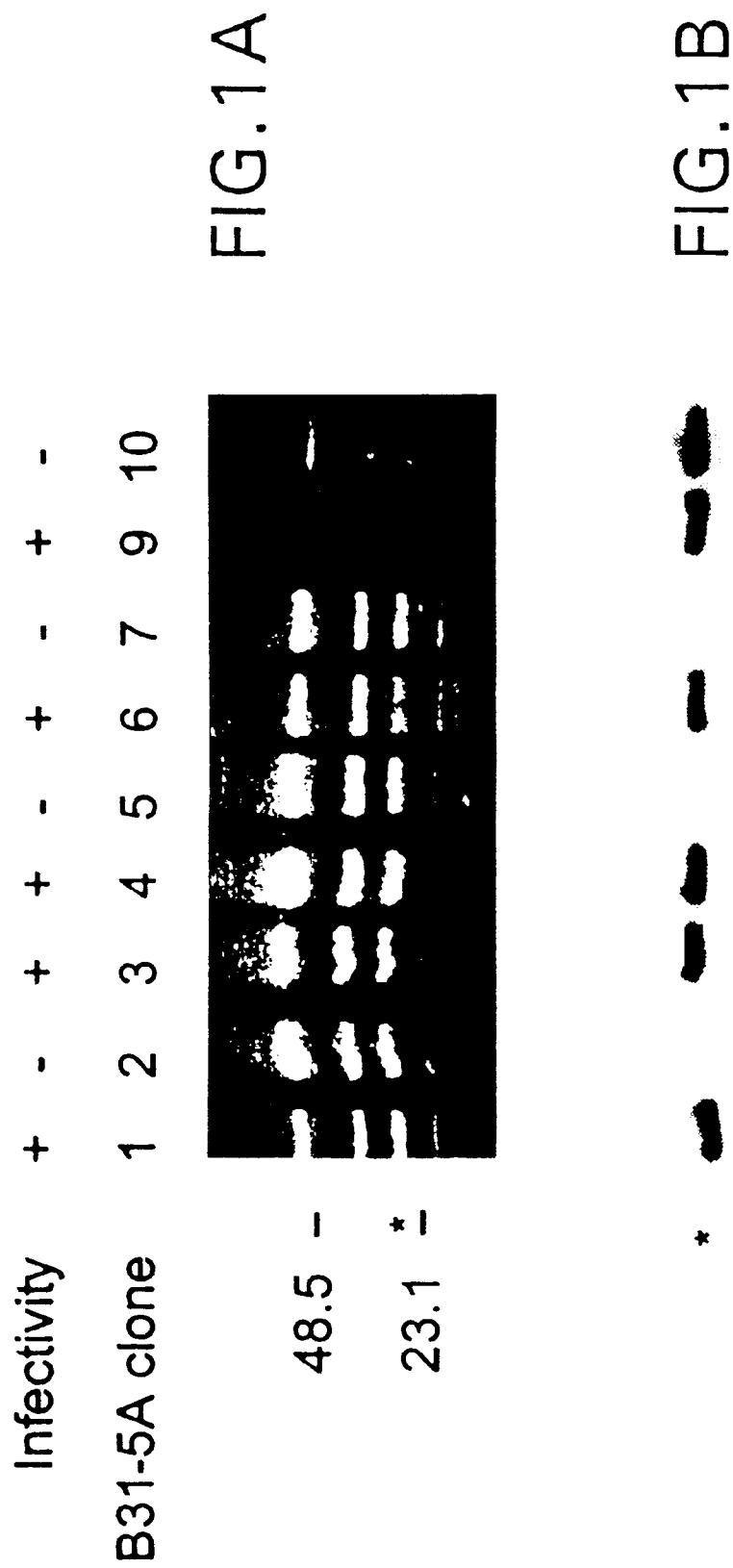

```
                                                                                    Lipoprotein signal peptide
                          -35                         -10              RBS
     ACCTACACTTGTTAAAACTCTCTTTTTGAGTTAAGATGATAACTTATACTTTCATTCATTGAAAAAAATTCAAGTGCAAGTTATTAACAACTTCTTTGTT
   1                                                                    M  K  K  I  S  S  A  S  L  L  T  T  F  F  V  F TTATTAATTGTAAAAGCCAAGTTGCTGATAAGGACGACCCAACAAACAAATTTACCAATCTGTCATACAATTAGTAACGGATTCTTGATGTATTCACATCTTTGGTGGGTTAGTAG
 121  I  N  C  K  S  Q  V  A  D  K  D  D  P  T  N  K  F  Y  Q  S  V  I  Q  L  G  N  G  F  L  D  V  F  T  S  F  G  G  L  V  A CAGAGGCTTTTGGATTTAAATCAGATCCAAAAAAATCTGATGTAAAAACCTATTTTACTGTAGCTGCCAAATTGGAAAAAACAAAAACCGATCTTAATAGTTGCCTAAGGAAAAAA
 241  E  A  F  G  F  K  S  D  P  K  K  S  D  V  K  T  Y  F  T  T  V  A  K  L  E  K  T  K  T  D  L  N  S  L  P  K  E  K  S 17-bp direct repeat
     GCGATAAGTAGTACGACGACGGGAAACCAGATAGTACAGGTTCTGTTGGAACTGCCGTTGAGGGGCTATTAAGGAGTTAGGCAGTTGTTGGATAAGCTGTAAAGCTGTAAAGACAG
 361  D  I  S  S  T  T  G  K  P  D  S  T  G  S  V  G  T  A  V  E  G  A  I  K  E  V  S  E  L  L  D  K  L  V  K  A  V  K  T  A
                                          Primer F4120

CTGAGGGGCTTCAAGTGGCTACTGCTGCTGTTAGTGCTGTTAGTGGGGAGCAATTGTGGCCTGATGCTGATGCGGATGCTGCAAAGTTGCTGATAAGGCGAGTGTGAAGGGGATAAAAGGAGATTGTTG
 481  E  G  A  S  S  G  T  A  A  I  G  E  V  V  A  D  A  D  A  A  K  V  A  D  K  A  S  V  K  G  I  A  K  G  I  K  E  I  V  E

AAGCTCTGGGGGAGTGAAAAGCTGAAAGCTGTTGCTGTTAGTGCTGCTAAAGGGGAGAATAATAAAGGGGAAGCAGGAAAGCTGGTGTTTGGGAAGGCAGGAGCAGCACATGGGGACAGTGAGGCTG
 601  A  A  G  G  S  E  K  L  K  A  V  A  A  K  G  E  N  N  K  G  A  G  K  L  F  G  K  A  G  A  A  A  H  G  D  S  E  A

CTAGCAAGGCGGCTGGTGCTGCTGTTAGTGCTGAAGCAGATAATTAAGTGCCATTGTTACGGCTGCTGATGCGGCTGAGCAGGATGGAAAGAAGCCTGAGGAGGCTAAAAAATCCGA
 721  S  K  A  A  G  A  V  S  A  V  S  G  E  Q  I  L  S  A  I  V  T  A  A  D  A  A  E  Q  D  G  K  K  P  E  E  A  K  N  P  I
                                                        Primer F4064

TTGCTGCTGCTATTGGGGATAAAGATGGGGGTCCGGAGTTTGGTCAGGATGAAATGAAGAAGGATGATCAGATTGCTGCTATTGCTTTGAGGGGATGCCTAAGGATGGAAAGTTTG
 841  A  A  A  I  G  D  K  D  G  G  A  E  F  G  Q  D  E  M  K  K  D  D  Q  I  A  A  I  A  L  R  G  M  A  K  D  G  K  F  A
                                                                                 Primer R4066
                    Primer R4121            17-bp direct repeat
     CTGTGAAGGATGGTGAGAAGAAGAAGGCTGAGGGGCTATTAAGGAGCTGCTGAGTCGCAGTTCGCAAAGTTTAGGGCTATTACTGGGCTAATAGGACGCCGTGAGTTCCGGC
 961  V  K  D  G  E  K  E  A  E  G  A  I  K  G  A  A  E  S  A  V  R  K  V  L  G  A  I  T  G  L  I  G  D  A  V  S  S  G  L TAAGGAAAGTCGGTGATTCAGTGAAGCTGTAGTAAAGAAACACCTCCTGCCTTGAATAAGTGATTAATTAAGTGTATGGACGACTATGCCCTCATGATTGAGGAAATAGTCGAGA
1081  R  K  V  G  D  S  V  K  A  A  S  K  E  T  P  P  A  L  N  K  *

1201 GATATATATACTAAAGATAATAAATA 1227
```

FIG.2C

```
VlsE1    1  MKKISSASLLTTFFVFINCKSQVADKDDPTNKFYQSVIQLGNGFLDVFTSFGGLVAEAFGFKSDPKKSDVKTYFTTVAAKLEKTKTDLNSLPKEKSDISS
            |::|   || :::|: |:: ::   ||::   ||   :  |::|   ||    ||::|: |||:: |||:   ||: |||::   :
Vmp17    1  MRKRISAIIMTLFMVLVSCNSGGVA.EDPKTVYLTSIANLGKFLDVFVTFGDMVTGAFGIKADTKKSDIGKYFTDIESTMTSVKKKLQ.........D

VlsE1  101  TTGKPDSTGSVGTAVEGAIKEVSELLDKLVKAVKTAEGASSGTAAIGEVVADADAAKVADKASVKGIAKGIKEIVEAAGGSEKLKAVAAKGENNKGAGK
            ..|..:.| |||   |||:  ::|:|||| :::|::|  ||||::|||.|||||||| ||:: :||||:||||  :  |:|  ::  ..|.::  ||
Vmp17   90  EVAKNGNYPKVKTAVD....EFVAILGKIEKGAKEASKGATGDVIIGNTVKNGDAV.PGEATSVNSLVKGIKEIVGVVLKEGKADA.DATKDDSKKDIGK

VlsE1  201  LFGKAGAAHGDSEAASKAAGAVSAVSGEQILSAIV......TAADAAEQDGKKPEEAKNPIAAAIGDKDGGAEFGQDEMKKDDQIAAAIALRGMAKDGKF
            ||.:|  :.:|||.|: ||| ::|| |:|| |::       :|:||.:|  :|  |    |  ||||| ::: :|||::||::|| ||| || |::||
Vmp17  184  LFTATTDANRADNAAAQAAAASIGAVTGADILQAIVQSKENPVANSTDGIEKATDAAEIAVAPAKDNKKE......IKDGAKKDAVIAAGIALRAMAKNGTF

VlsE1  296  AVKDGEKEKAEGAIKGAAESAVRKVLGAITGLIGDAVSSGLRKVGDSVKAASKETPPALNK  356
            .:.| :|::  ::|:     |:|  || ||  |:|...|||| :| ||: :     :
Vmp17  280  SIKNNE.DAAVTTINSAAASAVNKILSTLIIAIRNTVDSGLKTINEALATVKQEDKSVEAT  339
```

FIG. 3A

FIG. 3B

Proteinase K Digestion

− +

− +

− +

```
B. burgdorferi
    B31-5A3
         │
         │   Inoculation
         │   ($10^5$ cells/mouse ID)
         ▼
 8 C3H/HeN
    mice
         │
         │  4 weeks
        ╱ ╲
       ╱   ╲
     Ear    Blood
      │       │
      │       │ Reisolation
      ▼       ▼
 Select isolated colonies
 (clones) for each isolate
      │       │
      ▼       ▼
 Amplify visE cassette region
      by PCR & sequence
```

FIG. 5A

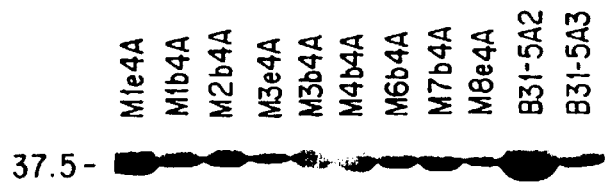
FIG. 6A
FIG. 6B
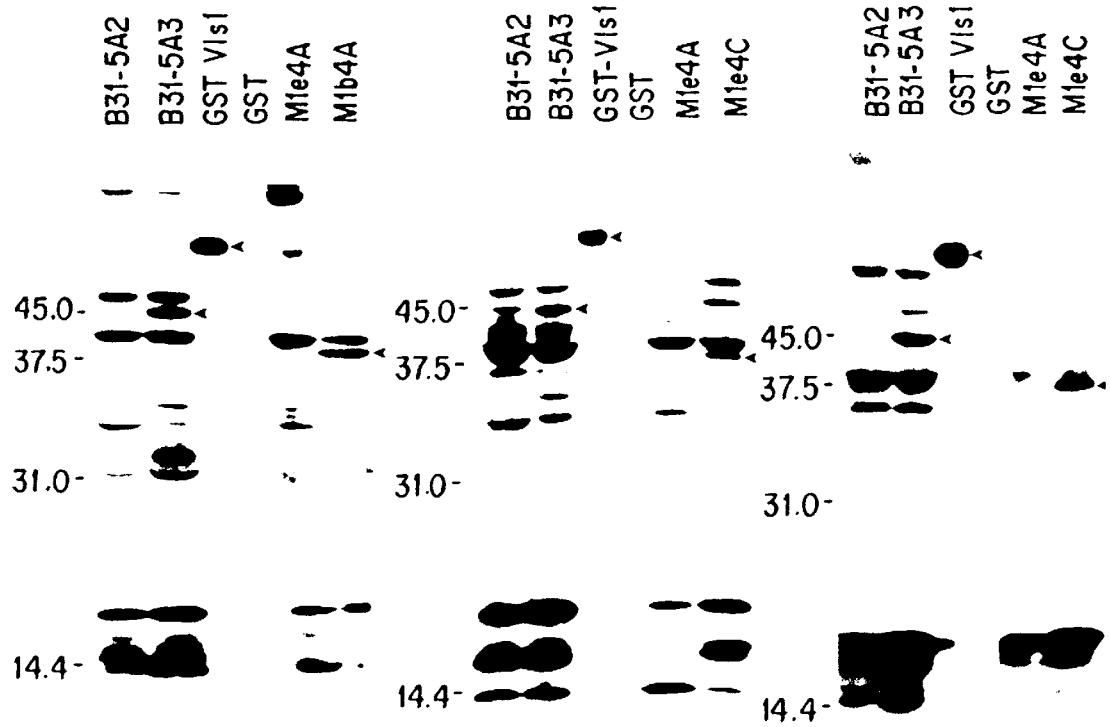
FIG. 6C  FIG. 6D  FIG. 6E

VMP-LIKE SEQUENCES OF PATHOGENIC BORRELIA

This application is a Divisional Application of U.S. application Ser. No. 09/125,619 filed on Jan. 27, 1999 now U.S. Pat. No. 6,437,116, which is a continuation of PCT Application PCT/US97/02952 filed Feb. 20, 1997, which is a continuation-in-part and claims priority to Provisional Application Serial No. 60/012,028 filed on Feb. 21, 1996.

1.0 BACKGROUND OF THE INVENTION

1.1 Field of the Invention

The invention relates to the field of molecular biology; in particular, to immunogenic compositions and recombinant VMP-like genes useful for treatment and diagnosis of Lyme disease. Also included are methods for the determination of virulence factors in Lyme disease.

1.2 Description of Related Art

Lyme disease is a bacterial infection caused by pathogenic spirochetes of the genus Borrelia. The infection can occur in humans, dogs, deer, mice and other animals, and is transmitted by arthropod vectors, most notably ticks of the genus Ixodes. *Borrelia burgdoferi*, the most common cause of Lyme disease in North America, was first cultured in 1982. *B. garinii* and *B. afzelii* are the most common infectious agents of Lyme disease in Europe, and another species, *B. japonicum*, has been described in Japan. These organisms are closely related and cause similar manifestations with multiple stages: an expanding rash at the site of the tick bite (erythema migrans); fever, lymphadenopathy, fatigue, and malaise; effects of disseminated infection, including carditis, meningoradiculitis, and polyarthritis; and chronic manifestations including arthritis and neurologic disorders. Lyme disease is often difficult to diagnose because of shared manifestations with other disorders, and it can also be refractory to treatment during late stages of the disease. It is most common in areas such as suburban regions of upstate New York and Connecticut, where large populations of deer and white-footed mice serve as the principal mammalian hosts and reservoirs of infection. Approximately 10,000 cases of Lyme disease in humans are reported per year in the United States, and it is also a significant veterinary problem due to a high infection rate of dogs and other domestic animals in endemic regions.

*B. burgdorferi*, the etiologic agent of Lyme disease, is able to persist for years in patients or animals despite the presence of an active immune response (Steer, 1989; Schutzer, 1992). Antigenic variation has been postulated previously as a mechanism whereby *B. burgdorferi* evades the immune response in the mammalian host (Schwan et al., 1991; Wilske et al., 1992). Antigenic variation has been defined as changes in the structure or expression of antigenic proteins that occurs during infection at a frequency greater than the usual mutation rate (Borst and Geaves, 1987; Robertson and Meyer, 1992; Seifert and So, 1988).

Relapsing fever is another disease caused by pathogenic Borrelia. It has both epidemic and endemic forms. The epidemic form is caused by *B. recurrentis* and is transmitted between humans by lice. It was a major source of morbidity and mortality during World War I, but has been rare since then due largely to public health measures. Endemic relapsing fever is an epizootic infection caused by several Borreliae species, including *B. hermsii*. It occurs sporadically among hunters, spelunkers, and others who come in contact with infected soft-bodied ticks of the genus Ornithidorus. Relapsing fever is characterized by two or more episodes or "relapses" of high bacteremia (up to $10^8$/ml). The first wave of infection is caused by Borreliae expressing a certain Variable Major Protein (VMP) on their surface (e.g. Vmp21). The gene encoding this VMP is located at a promoter site in the expression plasmid, whereas over 24 nonexpressed copies of different VMP genes are present on the so-called silent plasmid. When the host develops antibodies against the expressed VMP, the organisms of that stereotype are destroyed and the patient improves. However, a small proportion of organisms have undergone antigenic switching to a different stereotype. Nonreciprocal recombination occurs between the expression plasmid and the silent plasmid, resulting in the insertion of a different VMP gene in the expression site (e.g., Vmp7). The organisms expressing Vmp7 are not affected by the anti-Vmp21 antibodies, and therefore multiply in the host and cause a second episode of the disease. Up to five of these 3–5 day episodes can occur, separated by 1–2 week intervals.

Such well-demarcated episodes of infection do not occur during Lyme disease, and fewer organisms are present in the blood and in tissues at any stage. However, there are reasons to suspect that similar mechanisms of antigenic variation may occur in *B. burgdorferi* and other Lyme disease Borreliae The infection, if untreated, commonly persists for months to years despite the occurrence of host antibody and cellular responses; this observation indicates effective evasion of the immune response. Lyme disease may be disabling (particularly in its chronic form), and thus there is a need for effective therapeutic and prophylactic treatment.

Certain *B. burgdorferi* genes and proteins have been patented, including Outer Surface Protein D (OspD) (U.S. Pat. No. 5,246,844; issued Sep. 21, 1993). OspD has not proven to be a useful protein for diagnosis or immunoprotection. Other proteins, including OspA and OspC, have been considered as vaccine candidates for Lyme disease, including a recombinant OspA vaccine currently in human clinical trials. Other vaccines are in use or undergoing testing in veterinary applications, including vaccination of dogs. However, animal studies indicate that OspA vaccination may not be effective against all strains of Lyme disease Borreliae. OspA is also not useful for immunodiagnosis, due to weak antibody responses to OspA in Lyme disease patients.

Previous studies have generally failed to provide evidence for the occurrence of antigenic variation in Lyme disease Borrelia. Genetic heterogeneity in the genes encoding the membrane lipoproteins OspA, OspB, OspC, and OspD has been well documented among strains of Lyme disease Borreliae (Marconi et al., 1993; Marconi et al., 1994; Livey et al., 1995). In addition, mutations in ospA and ospB have been shown to occur in vitro (Rosa et al., 1992; Sadziene et al., 1992). However, no significant antigenic change (Barthold, 1993) or gross genetic alteration (Persing et al., 1994; Stevenson et al., 1994) has been detected in *B. burgdorferi* N40 isolates from chronically infected BALB/c and C3H mice, other than the loss of the 38-kilobase (kb) plasmid encoding OspD. Therefore the heterogeneity in Osp proteins observed among *B. burgdorferi* sensu lato isolates appears to represent evolutionary divergence ("antigenic drift") rather than antigenic variation.

There is a commercial demand for vaccines and diagnostic kits for Lyme disease, both for human and veterinary use. Several companies have active research and development programs in these areas.

2.0 SUMMARY OF THE INVENTION

Partial and complete DNA sequences have been determined for several recombinant clones containing DNA encoding VMP-like sequences. The identification and characterization of these sequences now allows: (1) identification of the expressed gene(s) in *B. burgdorferi;* (2) expression of these gene(s) by a recombinant vector in a host organism such as *E. coli;* (3) immunization of laboratory animals with the resulting polypeptide, and determination of protective activity against *B. burgdorferi* infection; (4) use of antibodies against the expressed protein to identify the reactive polypeptide(s) in *B. burgdorferi* cells; (5) use of the expressed protein(s) to detect antibody responses in infected humans and animals; (6) determination of the presence, sequence differences, and expression of the VMP-like DNA sequences in other Lyme disease Borreliae.

The invention is contemplated to be useful in the immunoprophylaxis, diagnosis, or treatment of Lyme disease, relapsing fever, or related diseases in humans or animals. It is expected that recombinant or native proteins expressed by the VMP-like genes (or portions thereof) will be useful for (a) immunoprophylaxis against Lyme disease, relapsing fever, or related disorders in humans and animals; (b) immunotherapy of existing Lyme disease, relapsing fever, or related illnesses, by way of immunization of injection of antibodies directed against VMP-like proteins; and (c) immunodiagnosis of Lyme disease, relapsing fever, or related diseases, including their use in kits in which the VMP-like proteins are the sole antigen or one of multiple antigens. The DNA may be employed in: (a) production of recombinant DNA plasmids or other vectors capable of expressing recombinant polypeptides; and (b) design and implementation of nucleic acid probes or oligonucleotides for detection and/or amplification of VMP-like sequences. The latter is expected to have application in the diagnosis of infection with Borrelial organisms.

Similar sequences in *B. burgdorferi* and other Lyme disease Borreliae have not been reported previously, as determined by BLAST searches of current nucleotide and amino acid databases including Genbank, the EMBL DNA database, and the Swiss Protein database. Although there is some similarity between the *B. burgdorferi* deduced amino acid sequences with previously published *B. hermsii* VMP deduced amino acid sequences, the degree of identity and similarity is only ~30% and ~50%, respectively. Outer surface protein C (OspC) of Lyme disease organisms has been reported to have sequence similarities to VMPs, but the highest similarity is to a different subgroup of VMPs than the sequences reported here (Carter et al., 1994). The VMP-like sequences such as those contained in pJRZ53-31 have a low degree of homology with OspC from some Lyme disease organisms (e.g. *B. burgdorferi* 2591), as indicated by a BLASTP homology score of 60 and a probability of 0.0013. Thus, the *B. burgdorferi* VMP-like DNA sequences are unique, although they have an apparent evolutionary relationship with other Borrelia genes.

Another aspect of the invention is the method for identification of possible virulence factors. This approach entails subtractive hybridization of target DNA from high infectivity organisms with driver DNA from low-infectivity strains or clones. This procedure greatly enriches for sequences which differ between the high- and low-infectivity strains and thus may encode proteins important in virulence. Of particular utility is the use of closely related isogenic clones that differ in their infectivity; in this case, the DNA differences should be restricted more stringently to those related to infectivity.

Open reading frames in a *B. burgdorferi* plasmid that encode hypothetical proteins resembling the VMP proteins of relapsing fever organisms have now been identified. The inventors have found that the presence of the plasmid containing these VMP-like sequences in *B. burgdorferi* clones correlates strongly with infectivity. Thus it is likely that the proteins encoded by the VMP-like sequences are important in immunoprotection and pathogenesis. Proteins encoded by the VMP-like sequences of *B. burgdorferi* may provide protection when used either alone or in combination with other antigens. They may also be useful for immunodiagnosis.

The invention is considered to include DNA segments corresponding to 20, 30, and 40 base pairs of the VMP-like sequences; DNA segments inclusive of the entire open reading frames of the VMP-like sequences; amino acid sequences corresponding to both conserved and variable regions of the VMP-like sequences; recombinant vectors encoding an antigenic protein corresponding to the above amino acid sequences; recombinant cells where extrachromosomal DNA expresses a polypeptide encoded by the DNA encoding Borrelia VMP-like sequences; a recombinant *B. burgdorferi* or *E. coli* cell containing the DNA encoding VMP-like sequences; methods of preparing transformed bacterial host cells using the DNA encoding the VMP-like polypeptides; methods using the plasmid or vector to transform the bacterial host cell to express *B. burgdorferi* polypeptides encoded by the DNA sequences; methods for immunization of humans or animals with the native *B. burgdorferi* polypeptide or polypeptides expressed by recombinant cells that include DNA encoding the VMP-like polypeptides; and methods for identifying potential virulence factors using subtractive hybridization between target DNA from high-infectivity cells and driver DNA from low-infectivity cells.

Also included in the invention are primer sets capable of priming amplification of the VMP-like DNA sequences; kits for the detection of *B. burgdorferi* nucleic acids in a sample, the kits containing a nucleic acid probe specific for the VMP-like sequences, together with a means for detecting a specific hybridization with the probe; kits for detection of antibodies against the VMP-like sequences of *B. burgdorferi* and kits containing a native or recombinant VMP-like polypeptide, together with means for detecting a specific binding of antibodies to the antigen.

2.1 Methods of Treatment

An important aspect of the invention is the recognition that Borrelia VMP-like sequences recombine at the vls site, with the result that antigenic variation is virtually limitless Multiclonal populations therefore can exist in an infected patient so that immunological defenses are severely tested if not totally overwhelmed. Thus there is now the opportunity to develop more effective combinations of immunogens for protection against Borrelia infections or as preventive inoculations such as in the form of cocktails of multiple antigenic variants based on a base series of combinatorial VMP-like antigens.

VMP-like protein preparations may be administered in several ways, either locally or systematically in pharmaceutically acceptable formulations. Amounts appropriate for administration are determined on an individual basis depending on such factors as age and sex of the subject, as well as physical condition and weight. Such determinations are well within the skill of the practitioner in the medical field.

Other methods of administration may include injection of Borrelia VMP-like DNAs into vaccine recipients (human or animal) driven by an appropriate promoter such as CMV, (so called DNA vaccines). Such preparations could be injected directly into lesions or transplanted into patients for systemic immunization. DNA vaccinations techniques are currently well past the initial development stage and have shown promise as vaccination strategies.

2.2 VMP-like Genes

Recombinant proteins and polypeptides encoded by isolated DNA segments and genes are often referred to with the prefix "r" for recombinant. As such, DNA segments encoding rVMPs, or rVMP-related genes, etc. are contemplated to be particularly useful in connection with this invention. Any recombinant vls combining any of the vlsE expression site loci and/or silent vls cassettes (vls2-vls-16) gene would likewise be very useful with the methods of the invention.

Isolation of the DNA encoding VMP polypeptides allows one to use methods well known to those of skill in the art and as herein described to make changes in the codons for specific amino acids such that the codons are "preferred usage" codons for a given species. Thus for example, preferred codons will vary significantly for bacterial species as compared with mammalian species; however, there are preferences even among related species. Shown below is a preferred codon usage table human. Isolation of spirochete DNA encoding VMP will allow substitutions for preferred human codons, although expressed polypeptide product from human DNA is expected to be homologous to bacterial VMP and so would be expected to be structurally and functionally equivalent to VMP isolated from a spirochete. However, substitutions of preferred human codons may improve expression in the human host, thereby improving the efficiency of potential DNA vaccines.

screening of a cDNA or genomic library, using primers or probes with sequences based on the above nucleotide sequence. Such fragments may be readily prepared by, for example, directly synthesizing the fragment by chemical means, by application of nucleic acid reproduction technology, such as the PCR™ technology of U.S. Pat. Nos. 4,683,195 and 4,683,202 (herein incorporated by reference). The practice of these techniques is a routine matter for those of skill in the art, as taught in various scientific texts (see e.g., Sambrook et al., 1989), incorporated herein by reference. Certain documents further particularly describe suitable mammalian expression vectors, e.g., U.S. Pat. No. 5,168,050, incorporated herein by reference. The VMP genes and DNA segments that are particularly preferred for use in certain aspects of the present methods are those encoding VMP and VMP-related polypeptides.

It is also contemplated that one may clone other additional genes or cDNAs that encode a VMP or VMP-related peptide, protein or polypeptide. The techniques for cloning DNA molecules, i.e., obtaining a specific coding sequence from a DNA library that is distinct from other portions of DNA, are well known in the art. This can be achieved by, for example, screening an appropriate DNA library which relates to the cloning of a vls gene such as from the variable region of that gene. The screening procedure may be based on the hybridization of oligonucleotide probes, designed from a consideration of portions of the amino acid sequence of known DNA sequences encoding related Borrelia proteins. The operation of such screening protocols is well known to those of skill in the art and are described in detail in the scientific literature, for example, see Sambrook et al., 1989.

TABLE 1

Homo sapiens

| Codon | $\upsilon^b$ | Total #[a] | Codon | $\upsilon^b$ | Total #[a] | Codon | $\upsilon^a$ | Total #[a] | Codon | $\upsilon^b$ | Total #[a] |
|---|---|---|---|---|---|---|---|---|---|---|---|
| UUU | 16.6 | 72711 | UCU | 14.0 | 62953 | UAU | 12.3 | 55039 | UGU | 9.5 | 42692 |
| UUC | 21.4 | 95962 | UCC | 17.7 | 79482 | UAC | 17.0 | 76480 | UGC | 12.8 | 57368 |
| UUA | 6.3 | 28202 | UCA | 10.7 | 48225 | UAA | 0.7 | 2955 | UGA | 1.2 | 5481 |
| UUG | 11.5 | 51496 | UCG | 4.4 | 19640 | UAG | 0.5 | 2181 | UGG | 13.5 | 59982 |
| CUU | 11.7 | 52401 | CCU | 16.7 | 74975 | CAU | 9.6 | 43193 | CGU | 4.6 | 20792 |
| CUC | 19.5 | 87696 | CCC | 20.0 | 89974 | CAC | 14.6 | 65533 | CGC | 11.0 | 49507 |
| CUA | 6.3 | 28474 | CCA | 16.2 | 72711 | CAA | 11.4 | 51146 | CGA | 5.9 | 26551 |
| CUG | 40.6 | 182139 | CCG | 6.9 | 30863 | CAG | 33.7 | 151070 | CGG | 11.3 | 50682 |
| AUU | 15.7 | 70652 | ACU | 12.8 | 57288 | AAU | 16.6 | 74401 | AGU | 11.1 | 49894 |
| AUC | 23.7 | 106390 | ACC | 21.1 | 94793 | AAC | 21.1 | 94725 | AGC | 19.1 | 85754 |
| AUA | 6.7 | 30139 | ACA | 14.7 | 66136 | AAA | 23.2 | 104221 | AGA | 10.8 | 48369 |
| AUG | 22.6 | 101326 | ACG | 6.7 | 30059 | AAG | 33.9 | 152179 | AGG | 10.9 | 48882 |
| GUU | 10.6 | 47805 | GCU | 18.7 | 83800 | GAU | 22.0 | 98712 | GCU | 11.2 | 50125 |
| GUC | 15.6 | 70189 | GCC | 29.2 | 130966 | GAC | 27.0 | 121005 | GGC | 24.0 | 107571 |
| GUA | 6.6 | 29659 | GCA | 15.3 | 68653 | GAA | 27.8 | 124852 | GGA | 16.9 | 75708 |
| GUG | 30.0 | 134750 | GCG | 7.5 | 33759 | GAG | 40.8 | 182943 | GGG | 16.7 | 74859 |

Coding GC 52.96% 1st letter GC 55.98% 2nd letter GC 42.29% 3rd letter GC 60.60%
[a]Total 4489120
[b]$\upsilon$ = Frequency per 1000

The definition of a "VMP-like gene", "VMP-related gene" as used herein, is a gene that hybridizes, under relatively stringent hybridization conditions (see, e.g., Maniatis et al., 1982), to DNA sequences presently known to include related gene sequences.

To prepare an VMP-like gene segment or cDNA one may follow the teachings disclosed herein and also the teachings of any of patents or scientific documents specifically referenced herein. One may obtain a rVMP- or other related-encoding DNA segments using molecular biological techniques, such as polymerase chain reaction (PCR™) or Techniques for introducing changes in nucleotide sequences that are designed to alter the functional properties of the encoded proteins or polypeptides are well known in the art, e.g., U.S. Pat. No. 4,518,584, incorporated herein by reference, which techniques are also described in further detail herein. Such modifications include the deletion, insertion or substitution of bases, and thus, changes in the amino acid sequence. Changes may be made to increase the VMP activity of a protein, to increase its biological stability or half-life, to change its glycosylation pattern, and the like. All such modifications to the nucleotide sequences are encompassed by this invention.

2.3 VMP-Encoding DNA Segments

The present invention, in a general and overall sense, also concerns the isolation and characterization of novel vls gene segments, which encode combinatorial mosaics of expressed and silent regions of the vls gene. A preferred embodiment of the present invention is a purified nucleic acid segment that encodes a protein that has at least a partial amino acid sequence in accordance with SEQ ID NO:2 Another embodiment of the present invention is a purified nucleic acid segment, further defined as including nucleotide sequences in accordance with SEQ ID NO:1 and SEQ ID NO:3.

In a more preferred embodiment the purified nucleic acid segment consists essentially of the nucleotide sequence of SEQ ID NO:1 and SEQ ID NO:3, their complement or the degenerate variants thereof. As used herein, the term "nucleic acid segment" and "DNA segment" are used interchangeably and refer to a DNA molecule which has been isolated free of total genomic DNA of a particular species. Therefore, a "purified" DNA or nucleic acid segment as used herein, refers to a DNA segment which contains a VMP coding sequence yet is isolated away from, or purified free from, total genomic DNA, for example, total cDNA or borrelia genomic DNA. Included within the term "DNA segment", are DNA segments and smaller fragments of such segments, and also recombinant vectors, including, for example, plasmids, cosmids, phage, viruses, and the like.

Similarly, a DNA segment comprising an isolated or purified vls gene refers to a DNA segment including VMP-related coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences, cDNA sequences or combinations thereof "Isolated substantially away from other coding sequences" means that the gene of interest, in this case vls, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man, nor are other portions or contiguous sequences of naturally occurring DNA excluded.

In particular embodiments, the invention concerns isolated DNA segments and recombinant vectors incorporating DNA sequences which encode a VMP-like protein that includes within its amino acid sequence an amino acid sequence in accordance with SEQ ID NO:2.

Another preferred embodiment of the present invention is a purified nucleic acid segment that encodes a protein in accordance with SEQ ID NO:2, further defined as a recombinant vector. As used herein the term, "recombinant vector", refers to a vector that has been modified to contain a nucleic acid segment that encodes an VMP protein, or a fragment thereof. The recombinant vector may be further defined as an expression vector comprising a promoter operatively linked to said VMP-encoding nucleic acid segment.

A further preferred embodiment of the present invention is a host cell, made recombinant with a recombinant vector comprising an vls gene. The recombinant host cell may be a prokaryotic cell. As used herein, the term "engineered" or "recombinant" cell is intended to refer to a cell into which a recombinant gene, such as a gene encoding VMP, has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a copy of a genomic gene or a cDNA gene, or will include genes positioned adjacent to a promoter not naturally associated with the particular introduced gene.

In certain embodiments, the invention concerns isolated DNA segments and recombinant vectors which encode a protein or peptide that includes within its amino acid sequence an amino acid sequence essentially as set forth in SEQ ID NO:2. Naturally, where the DNA segment or vector encodes a full length VMP-like protein, or is intended for use in expressing the VMP-like protein, the most preferred sequences are those which are essentially as set forth in SEQ ID NO:2. It is recognized that SEQ ID NO:2 represents the full length protein encoded by the vls gene and that contemplated embodiments include up to the full length sequence and functional variants as well.

The term "a sequence essentially as set forth in SEQ ID NO:2" means that the sequence substantially corresponds to a portion of SEQ ID NO:2 and has relatively few amino acids which are not identical to, or a biologically functional equivalent of, the amino acids of SEQ ID NO:2. The term "biologically functional equivalent" is well understood in the art and is further defined in detail herein, as a gene having a sequence essentially as set forth in SEQ ID NO:1 and that is associated with a vls gene in the Borrelia family. Accordingly, sequences which have between about 70% and about 80%; or more preferably, between about 85% and about 90%; or even more preferably, between about 90 and 95% and about 99%; of amino acids which are identical or functionally equivalent to the amino acids of SEQ ID NO:2 will be sequences which are "essentially as set forth in SEQ ID NO:2".

In certain other embodiments, the invention concerns isolated DNA segments and recombinant vectors that include within their sequence a nucleic acid sequence essentially as set forth in SEQ ID NO:1 and SEQ ID NO:3. The term "essentially as set forth in SEQ ID NO:1 and SEQ ID NO:3," is used in the same sense as described above and means that the nucleic acid sequence substantially corresponds to a portion of SEQ ID NO:1 and SEQ ID NO:3, and has relatively few codons which are not identical, or functionally equivalent, to the codons of SEQ ID NO:1 and SEQ ID NO:3. The term "functionally equivalent codon" is used herein to refer to codons that encode the same amino acid, such as the six codons for arginine or serine, as set forth in Table 4, and also refers to codons that encode biologically equivalent amino acids.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences which have between about 70% and about 80%; or more preferably, between about 80%, 85% and about 90%; or even more preferably, between about 90%, 95% and about 99%; of nucleotides which are identical to the nucleotides of SEQ ID NO:1 and SEQ ID NO:3 will be sequences which are "essentially as set forth in SEQ ID NO:1 and SEQ ID NO:3". Sequences which are essentially the same as those set forth in SEQ ID NO:1 and SEQ ID NO:3 may also be functionally defined as sequences which are capable of hybridizing to a nucleic acid segment containing the complement of SEQ ID NO:1 and SEQ ID NO:3 under relatively stringent conditions or conditions of high stringency. Suitable relatively stringent hybridization conditions will be well known to those of skill in the art and are clearly set forth herein, for example conditions for use with Southern and Northern blot analysis, and as described in the examples herein set forth.

Naturally, the present invention also encompasses DNA segments which are complementary, or essentially complementary, to the sequence set forth in SEQ ID NO:1 and SEQ ID NO:3. Nucleic acid sequences which are "complementary" are those which are capable of base-pairing according to the standard Watson-Crick complementary rules. As used herein, the term "complementary sequences" means nucleic acid sequences which are substantially complementary, as may be assessed by the same nucleotide comparison set forth above, or as defined as being capable of hybridizing to the nucleic acid segment of SEQ ID NO:1 and SEQ ID NO:3 under relatively stringent conditions, i e., conditions of high stringency.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared which include a short stretch complementary to SEQ ID NO:1 and SEQ ID NO:3, such as about 10 to 15 or 20, 30, or 40 or so nucleotides, and which are up to 2000 or so base pairs in length. DNA segments with total lengths of about 8000, 7000, 6000, 5000, 4000, 3000, 2000, 1000, 500, 200, 100 and about 50 base pairs in length are also contemplated to be useful.

A preferred embodiment of the present invention is a nucleic acid segment which comprises at least a 14-nucleotide long stretch which corresponds to, or is complementary to, the nucleic acid sequence of SEQ ID NO:1 and SEQ ID NO:3. In a more preferred embodiment the nucleic acid is further defined as comprising at least a 20 nucleotide long stretch, a 30 nucleotide long stretch, 50 nucleotide long stretch, 100 nucleotide long stretch, or at least an 2000 nucleotide long stretch which corresponds to, or is complementary to, the nucleic acid sequence of SEQ ID NO:1 and SEQ ID NO:3. The nucleic acid segment may be further defined as having the nucleic acid sequence of SEQ ID NO:1 and SEQ ID NO:3.

A related embodiment of the present invention is a nucleic acid segment which comprises at least a 14-nucleotide long stretch which corresponds to, or is complementary to, the nucleic acid sequence of SEQ ID NO:1 and SEQ ID NO:3, further defined as comprising a nucleic acid fragment of up to 10,000 basepairs in length. A more preferred embodiment if a nucleic acid fragment comprising from 14 nucleotides of SEQ ID NO:1 and SEQ ID NO:3 up to 5,000 basepairs in length, 3,000 basepairs in length, 2,000 basepairs in length, 1,000 basepairs in length, 500 basepairs in length, or 100 basepairs in length.

Naturally, it will also be understood that this invention is not limited to the particular nucleic acid and amino acid sequences of SEQ ID NO:1 and SEQ ID NO:3. Recombinant vectors and isolated DNA segments may therefore variously include the VMP-like protein coding regions themselves, coding regions bearing selected alterations or modifications in the basic coding region, or they may encode larger polypeptides which nevertheless include VMP-coding regions or may encode biologically functional equivalent proteins or peptides which have variant amino acids sequences.

The DNA segments of the present invention encompass biologically functional equivalent VMP-like proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the VMP-like protein or to test VMP-like mutants in order to examine activity or determine the presence of VMP-like peptide in various cells and tissues at the molecular level.

A preferred embodiment of the present invention is a purified composition comprising a polypeptide having an amino acid sequence in accordance with SEQ ID NO:2. The term "purified" as used herein, is intended to refer to an VMP-related protein composition, wherein the VMP-like protein is purified to any degree relative to its naturally-obtainable state, i.e., in this case, relative to its purity within a eukaryotic cell extract. A preferred cell for the isolation of VMP-like protein is from borrelia organisms; however, VMP-like protein may also be isolated from various patient specimens, specimens from infected animals, recombinant cells, tissues, isolated subpopulations of tissues, and the like, as will be known to those of skill in the art, in light of the present disclosure. A purified VMP-like protein composition therefore also refers to a polypeptide having the amino acid sequence of SEQ ID NO:2, free from the environment in which it may naturally occur.

If desired, one may also prepare fusion proteins and peptides, e.g., where the VMP-like protein coding regions are aligned within the same expression unit with other proteins or peptides having desired functions, such as for purification or immunodetection purposes (e.g., proteins which may be purified by affinity chromatography and enzyme label coding regions, respectively).

Turning to the expression of the vls gene whether from cDNA based or genomic DNA, one may proceed to prepare an expression system for the recombinant preparation of VMP-like protein. The engineering of DNA segment(s) for expression in a prokaryotic or eukaryotic system may be performed by techniques generally known to those of skill in recombinant expression. For example, one may prepare a VMP-GST (glutathione-S-transferase) fusion protein that is a convenient means of bacterial expression. However, it is believed that virtually any expression system may be employed in the expression of VMP-like proteins.

VMP-like proteins may be successfully expressed in eukaryotic expression systems, however, the inventors contemplate that bacterial expression systems may be used for the preparation of VMP for all purposes. The cDNA containing vls gene may be separately expressed in bacterial systems, with the encoded proteins being expressed as fusions with β-galactosidase, avidin, ubiquitin, *Schistosoma japonicum* glutathione S-transferase, multiple histidines, epitope-tags and the like. It is believed that bacterial expression will ultimately have advantages over eukaryotic expression in terms of ease of use and quantity of materials obtained thereby.

It is proposed that transformation of host cells with DNA segments encoding VMP-like proteins will provide a convenient means for obtaining a VMP-like protein. It is also proposed that cDNA, genomic sequences, and combinations thereof, modified by the addition of a eukaryotic or viral promoter, are suitable for eukaryotic expression, as the host cell will of, course, process the genomic transcripts to yield functional mRNA for translation into protein.

Another embodiment is a method of preparing a protein composition containing growing recombinant host cell comprising a vector that encodes a protein which includes an amino acid sequence in accordance with SEQ ID NO:2, under conditions permitting nucleic acid expression and protein production followed by recovering the protein so produced. The host cell, conditions permitting nucleic acid expression, protein production and recovery, will be known to those of skill in the art, in light of the present disclosure of the vls gene.

2.4 Gene Constructs and DNA Segments

As used herein, the terms "gene" and "DNA segment" are both used to refer to a DNA molecule that has been isolated free of total genomic DNA of a particular species. Therefore, a gene or DNA segment encoding an VMP-like polypeptide refers to a DNA segment that contains sequences encoding an VMP-like protein, but is isolated away from, or purified free from, total genomic DNA of the species from which the DNA is obtained. Included within the term "DNA segment", are DNA segments and smaller fragments of such segments, and also recombinant vectors, including, for example, plasmids, cosmids, phage, retroviruses, adenoviruses, and the like.

The term "gene" is used for simplicity to refer to a functional protein or peptide encoding unit. As will be understood by those in the art, this functional term includes both genomic sequences and cDNA sequences. "Isolated substantially away from other coding sequences" means that the gene of interest, in this case, a VMP-like protein encoding gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions, such as sequences encoding leader peptides or targeting sequences, later added to the segment by the hand of man.

2.5 Recombinant Vectors Expressing VMP-like Proteins

A particular aspect of this invention provides novel ways in which to utilize VMP-encoding DNA segments and recombinant vectors comprising vls DNA segments. As is well known to those of skill in the art, many such vectors are readily available, one particular detailed example of a suitable vector for expression in mammalian cells is that described in U. S. Pat. No. 5,168,050, incorporated herein by reference. However, there is no requirement that a highly purified vector be used, so long as the coding segment employed encodes a VMP-like protein and does not include any coding or regulatory sequences that would have an adverse effect on cells. Therefore, it will also be understood that useful nucleic acid sequences may include additional residues, such as additional non-coding sequences flanking either of the 5' or 3' portions of the coding including, for example, promoter regions, or may include various internal sequences, i e., introns, which are known to occur within genes.

After identifying an appropriate VMP-encoding gene or DNA molecule, it may be inserted into any one of the many vectors currently known in the art, so that it will direct the expression and production of the VMP-like protein when incorporated into a host cell. In a recombinant expression vector, the coding portion of the DNA segment is positioned under the control of a promoter. The promoter may be in the form of the promoter which is naturally associated with a VMP-encoding gene, as may be obtained by isolating the 5' non-coding sequences located upstream of the coding segment or exon, for example, using recombinant cloning and/or PCR™ technology, in connection with the compositions disclosed herein.

In certain embodiments, it is contemplated that particular advantages will be gained by positioning the VMP-encoding DNA segment under the control of a recombinant, or heterologous, promoter. As used herein, a recombinant or heterologous promoter is intended to refer to a promoter that is not normally associated with a vls gene in its natural environment. Such promoters may include those normally associated with other borrelia-inhibitory polypeptide genes, and/or promoters isolated from any other bacterial, viral, eukaryotic, or mammalian cell. Naturally, it will be important to employ a promoter that effectively directs the expression of the DNA segment in the particular cell containing the vector comprising a vls gene or gene segment.

The use of recombinant promoters to achieve protein expression is generally known to those of skill in the art of molecular biology, for example, see Sambrook et al., (1989). The promoters employed may be constitutive, or inducible, and can be used under the appropriate conditions to direct high level or regulated expression of the introduced DNA segment. The currently preferred promoters are those such as CMV, RSV LTR, the SV40 promoter alone, and the SV40 promoter in combination with the SV40 enhancer.

2.6 Methods of DNA Transfection

Technology for introduction of DNA into cells is well-known to those of skill in the art. Five general methods for delivering a gene into cells have been described: (1) chemical methods (Graham and VanDerEb, 1973); (2) physical methods such as microinjection (Capecchi, 1980), electroporation (Wong and Neumann, 1982; Fromm et al., 1985) and the gene gun (Yang et al., 1990); (3) viral vectors (Clapp, 1993; Danos and Heard, 1992; Eglitis and Anderson, 1988); (4) receptor-mediated mechanisms (Wu et al., 1991; Curiel et al., 1991; Wagner et al., 1992); and (5) direct injection of purified DNA into human or animals.

2.7 Liposomes and Nanocapsules

The formation and use of liposomes is generally known to those of skill in the art (see for example, Couvreur et al., 1991 which describes the use of liposomes and nanocapsules in the targeted antibiotic therapy of intracellular bacterial infections and diseases). Recently, liposomes were developed with improved serum stability and circulation half-times (Gabizon and Papahadjopoulos, 1988; Allen and Choun, 1987). The following is a brief description of these DNA delivery modes.

Nanocapsules can generally entrap compounds in a stable and reproducible way (Henry-Michelland et al., 1987). To avoid side effects due to intracellular polymeric overloading, such ultrafine particles (sized around 0.1 mm) should be designed using polymers able to be degraded in vivo. Biodegradable polyalkyl-cyanoacrylate nanoparticles that meet these requirements are contemplated for use in the present invention, and such particles may be are easily made, as described (Couvreur et al., 1984; 1988).

Liposomes are formed from phospholipids that are dispersed in an aqueous medium and spontaneously form multilamellar concentric bilayer vesicles (also termed multilamellar vesicles (MLVs). MLVs generally have diameters ranging from 25 mm to 4 mm. Sonication of MLVs results in the formation of small unilamellar vesicles (SUVs) with diameters in the range of 200 to 500 Å, containing an aqueous solution in the core.

In addition to the teachings of Couvreur et al. (1991), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

2.8 Expression of VMP-like Proteins

For the expression of VMP-like proteins, once a suitable (full-length if desired) clone or clones have been obtained, whether they be cDNA based or genomic, one may proceed to prepare an expression system for the recombinant preparation of VMP-like proteins. The engineering of DNA segment(s) for expression in a prokaryotic or eukaryotic system may be performed by techniques generally known to those of skill in recombinant expression. It is believed that virtually any expression system may be employed in the expression of VMP-like proteins.

VMP-like proteins may be successfully expressed in eukaryotic expression systems, however, it is also envisioned that bacterial expression systems may be preferred for the preparation of VMP-like proteins for all purposes. The cDNA for VMP-like proteins may be separately expressed in bacterial systems, with the encoded proteins being expressed as fusions with b-galactosidase, ubiquitin, *Schistosoma japonicum* glutathione S-transferase, green fluorescent protein and the like. It is believed that bacterial expression will ultimately have advantages over eukaryotic expression in terms of ease of use and quantity of materials obtained thereby.

It is proposed that transformation of host cells with DNA segments encoding VMP-like proteins will provide a convenient means for obtaining VMP-like peptides. Both cDNA and genomic sequences are suitable for eukaryotic expression, as the host cell will, of course, process the genomic transcripts to yield functional mRNA for translation into protein.

It is similarly believed that almost any eukaryotic expression system may be utilized for the expression of VMP-like proteins, e.g., baculovirus-based, glutamine synthase-based or dihydrofolate reductase-based systems could be employed. However, in preferred embodiments, it is contemplated that plasmid vectors incorporating an origin of replication and an efficient eukaryotic promoter, as exemplified by the eukaryotic vectors of the pCMV series, such as pCMV5, will be of most use.

For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter.

Where eukaryotic expression is contemplated, one will also typically desire to incorporate into the transcriptional unit which includes VMP-like protein, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

Translational enhancers may also be incorporated as part of the vector DNA. Thus the DNA constructs of the present invention should also preferable contain one or more 5' non-translated leader sequences which may serve to enhance expression of the gene products from the resulting mRNA transcripts. Such sequences may be derived from the promoter selected to express the gene or can be specifically modified to increase translation of the RNA. Such regions may also be obtained from viral RNAs, from suitable eukaryotic genes, or from a synthetic gene sequence (Griffiths, et al., 1993).

Such "enhancer" sequences may be desirable to increase or alter the translational efficiency of the resultant mRNA. The present invention is not limited to constructs where the enhancer is derived from the native 5'-nontranslated promoter sequence, but may also include non-translated leader sequences derived from other non-related promoters such as other enhancer transcriptional activators or genes.

It is contemplated that virtually any of the commonly employed host cells can be used in connection with the expression of VMPs in accordance herewith. Examples include cell lines typically employed for eukaryotic expression such as 239, AtT-20, HepG2, VERO, HeLa, CHO, WI 38, BHK, COS-7, RIN and MDCK cell lines.

It is contemplated that VMP-like protein may be "overexpressed", i.e., expressed in increased levels relative to its natural expression in borrelia cells, or even relative to the expression of other proteins in a recombinant host cell containing VMP-encoding DNA segments. Such overexpression may be assessed by a variety of methods, including radio-labeling and/or protein purification. However, simple and direct methods are preferred, for example, those involving SDS/PAGE and protein staining or Western blotting, followed by quantitative analyses, such as densitometric scanning of the resultant gel or blot. A specific increase in the level of the recombinant protein or peptide in comparison to the level in natural VMP-producing animal cells is indicative of overexpression, as is a relative abundance of the specific protein in relation to the other proteins produced by the host cell and, e.g., visible on a gel.

As used herein, the term "engineered" or "recombinant" cell is intended to refer to a cell into which a recombinant gene, such as a gene encoding a VMP peptide has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene.

It will be understood that recombinant VMPs may differ from naturally produced VMP in certain ways. In particular, the degree of post-translational modifications, such as, for example, lipidation, glycosylation and phosphorylation may be different between the recombinant VMP and the VMP polypeptide purified from a natural source, such as Borrelia.

After identifying an appropriate DNA molecule by any or a combination of means as described above, the DNA may then be inserted into any one of the many vectors currently known in the art and transferred to a prokaryotic or eukaryotic host cell where it will direct the expression and production of the so-called "recombinant" version of the protein. The recombinant host cell may be selected from a group consisting of S. mutans, E. coli, S. cerevisae. Bacillus sp., Lactococci sp., Enterococci sp., or Salmonella sp. In certain preferred embodiments, the recombinant host cell will have a recA phenotype.

Where the introduction of a recombinant version of one or more of the foregoing genes is required, it will be important to introduce the gene such that it is under the control of a promoter that effectively directs the expression of the gene in the cell type chosen for engineering. In general, one will desire to employ a promoter that allows constitutive (constant) expression of the gene of interest. The use of these-constitutive promoters will ensure a high constant level of expression of the introduced genes. The level of expression from the introduced genes of interest can vary in different clones, probably as a function of the site of insertion of the recombinant gene in the chromosomal DNA. Thus, the level of expression of a particular recombinant gene can be chosen by evaluating different clones derived from each transfection study; once that line is chosen, the constitutive promoter ensures that the desired level of expression is permanently maintained. It may also be possible to use promoters that are subject to regulation, such as those regulated by the presence of lactose analog or by the expression of bacteriophage T7 DNA polymerase.

2.9 Recombinant VMP-like Polypeptides

Recombinant versions of a protein or polypeptide are deemed as part of the present invention. Thus one may, using techniques familiar to those skilled in the art, express a recombinant version of the polypeptide in a recombinant cell to obtain the polypeptide from such cells. The techniques are based on cloning of a DNA molecule encoding the polypeptide from a DNA library, that is, on obtaining a specific DNA molecule distinct from other DNAs. One may, for example, clone a cDNA molecule, or clone genomic DNA. Techniques such as these would also be appropriate for the production of the VMP-like polypeptides in accordance with the present invention.

2.10 Enhanced Production of VMP-like Proteins

Potential problems with VMP-like proteins isolated from natural sources are low yields and extensive purification processes. An aspect of the present invention is the enhanced production of VMP-like proteins by recombinant methodologies in a bacterial host, employing DNA constructs to transform Gram-positive or Gram-negative bacterial cells. For example, the use of *Escherichia coli* expression systems is well known to those of skill in the art, as is the use of other bacterial species such as *Bacillus subtilis* or *Streptococcus sanguis*.

Further aspects of the invention include high expression vectors incorporating DNA encoding novel vls, combinatorial segments and its variants. It is contemplated that vectors providing enhanced expression of VMP in other systems such as *S. mutans* will also be obtainable. Where it is desirable, modifications of the physical properties of VMP may be sought to increase its solubility or expression in liquid culture The vls locus may be placed under control of a high expression promoter or the components of the expression system altered to enhance expression.

In further embodiments, the DNA encoding the VMP-like proteins of the present invention allows for the large scale production and isolation of VMP-like polypeptides. This can be accomplished by directing the expression of the VMP-like polypeptide by cloning the DNA encoding the VMP-like polypeptide into a suitable expression vector. Such an expression vector may then be transformed into a host cell that is able to produce the VMP-like proteins. The VMP-like protein may then be purified, e.g., by means provided for in this disclosure and utilized in a biologically active form. Non-biologically active recombinant VMP-like proteins may also have utility, e.g., as an immunogen to prepare anti-VM antibodies.

2.11 Gene Immunization

Adenovirus is particularly suitable for use as a gene transfer vector because of its mid-sized DNA genome, ease of manipulation, high titer, wide target-cell range, and high infectivity. The roughly 36 kB viral genome is bounded by 100–200 base pair (bp) inverted terminal repeats (ITR), in which are contained cis-acting elements necessary for viral DNA replication and packaging. The early (E) and late (L) regions of the genome that contain different transcription units are divided by the onset of viral DNA replication.

The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence which makes them preferred mRNAs for translation.

In order for adenovirus to be optimized for gene therapy, it is necessary to maximize the carrying capacity so that large segments of DNA can be included. It also is very desirable to reduce the toxicity and immunologic reaction associated with certain adenoviral products.

The large displacement of DNA is possible because the cis elements required for viral DNA replication all are localized in the inverted terminal repeats (ITR) (100–200 bp) at either end of the linear viral genome. Plasmids containing ITR's can replicate in the presence of a non-defective adenovirus (Hay et al., 1984). Therefore, inclusion of these elements in an adenoviral vector should permit replication.

In addition, the packaging signal for viral encapsidation is localized between 194–385 bp (0.5–1.1 map units) at the left end of the viral genome (Hearing et al., 1987). This signal mimics the protein recognition site in bacteriophage λ DNA where a specific sequence close to the left end, but outside the cohesive end sequence, mediates the binding to proteins that are required for insertion of the DNA into the head structure. E1 substitution vectors of Ad have demonstrated that a 450 bp (0–1.25 map units) fragment at the left end of the viral genome could direct packaging in 293 cells (Levrero et al., 1991).

It has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

2.12 VMP-like Variants

VMP-like related proteins and functional variants are also considered part of the invention. Thus it is expected that truncated and mutated versions of VMP-like protein (SEQ ID NO:2) will afford more convenient and effective forms of VMP for treatment regimens. Thus, any functional version of SEQ ID NO:2, such as truncated species or homologs, and mutated versions of VMP-like protein are considered as part of the invention.

Mutagenized recombinant VMPs may have increased potency and prolonged in vivo half-life, thereby offering more effective long-term treatments. Novel VMPs thus may be obtained by modifications to the vls gene, (such as by site-specific mutagenesis).

Additionally, the 15 silent vls cassettes of *B. burgdorferi* may be recombined in numerous combinations, providing for example a cocktail of peptide compositions for use as immunogens and to develop vaccines for use in Lyme disease and related conditions.

2.13 Pharmaceutical Compositions

Pharmaceutical compositions prepared in accordance with the present invention find use in preventing or ameliorating conditions associated with Borrelia infections, particularly Lyme disease. Such methods generally involve administering a pharmaceutical composition comprising an effective amount of a VMP-like antigen, such as SEQ ID NO:2 or various epitopes thereof. Other exemplary compositions may include an effective amount of either a VMP-like variant or a VMP-like encoding nucleic acid composition. Such compositions may also be used to generate an immune response in an animal in such cases where it may be desirable to block the effect of a naturally produced VMP-like protein.

Also included as part of the present invention therefore are novel compositions comprising nucleic acids which encode a VMP-like protein It will, of course, be understood that one or more than one gene may be used in the methods and compositions of the invention. The nucleic acid delivery methods may thus entail the administration of one, two, three, or more, homologous VMP-encoding genes. The maximum number of genes that may be applied is limited only by practical considerations, such as the effort involved in simultaneously preparing a large number of gene constructs or even the possibility of eliciting an adverse cytoloxic effect.

The particular combination of genes may be two or more distinct genes; or it may be such that a vls gene is combined with another gene and/or another protein, cofactor or other biomolecule; a cytokine gene may even be combined with a gene encoding a cell surface receptor capable of interacting with the polypeptide product of the first gene.

In using multiple genes, they may be combined on a single genetic construct under control of one or more promoters, or they may be prepared as separate constructs of the same or different types. Thus, an almost endless combination of different genes and genetic constructs may be employed. Certain gene combinations may be designed to, or their use may otherwise result in, achieving synergistic effects in affording protection against Borrelia and/or stimulation of an immune response. Any and all such combinations are intended to fall within the scope of the present invention. Indeed, many synergistic effects have been described in the scientific literature, so that one of ordinary skill in the art would readily be able to identify likely synergistic gene combinations, or even gene-protein combinations.

It will also be understood that, if desired, the nucleic acid segment or gene encoding a VMP-like protein could be administered in combination with further agents, such as, e.g., proteins or polypeptides or various pharmaceutically active agents. So long as the composition comprises a vls gene, there is virtually no limit to other components which may also be included, given that the additional agents do not cause a significant adverse effect upon contact with the target cells or host tissues. The nucleic acids may thus be delivered along with various other agents as required in the particular instance.

2.14 Kits

Therapeutic kits comprising VMP-like peptides or VMP-encoding nucleic acid segments comprise another aspect of the present invention. Such kits will generally contain, in suitable container means, a pharmaceutically acceptable formulation of a VMP-like peptide or a VMP-encoding nucleic acid composition. The kit may have a single container means that contains the VMP composition or it may have distinct container means for the VMP composition and other reagents which may be included within such kits.

The components of the kit may be provided as liquid solution(s), or as dried powder(s). When the components are provided in a liquid solution, the liquid solution is an aqueous solution, with a sterile aqueous solution being particularly preferred. When reagents or components are provided as a dry powder, the powder can be reconstituted by the addition of a suitable solvent It is envisioned that the solvent may also be provided in another container means.

Kits may also comprise reagents for detecting VMP-like polypeptides, such as required for immunoassay The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, a number of exemplary labels are known in the art and all such labels may be employed in connection with the present invention. The kits may contain antibody-label conjugates either in fully conjugated form, in the form of intermediates, or as separate moieties to be conjugated by the user of the kit.

The container means will generally include at least one vial, test tube, flask, bottle, syringe or other container means, into which the antigen or antibody may be placed, and preferably suitably aliquoted. Where a second binding ligand is provided, the kit will also generally contain a second vial or other container into which this ligand or antibody may be placed. The kits of the present invention will also typically include a means for containing the antibody, antigen, and reagent containers in close confinement for commercial sale. Such containers may include injection or blow-molded plastic containers into which the desired vials are retained.

2.15 VMP Antibodies

In another aspect, the present invention contemplates an antibody that is immunoreactive with a polypeptide of the invention. An antibody can be a polyclonal or a monoclonal antibody. In a preferred embodiment, an antibody is a monoclonal antibody. Means for preparing and characterizing antibodies are well known in the art (See, e.g., Howell and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

Antibodies, both polyclonal and monoclonal, specific for VMP-like polypeptides and particularly those represented by SEQ ID NO:2, variants and epitopes thereof, may be prepared using conventional immunization techniques, as will be generally known to those of skill in the art. A composition containing antigenic epitopes of VMP can be used to immunize one or more experimental animals, such as a rabbit or mouse, which will then proceed to produce specific antibodies against vls expression and silent regions. Polyclonal antisera may be obtained, after allowing time for antibody generation, simply by bleeding the animal and preparing serum samples from the whole blood.

To obtain monoclonal antibodies, one would also initially immunize an experimental animal, often preferably a mouse, with a VMP composition. One would then, after a period of time sufficient to allow antibody generation, obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones which can then be screened for production of antibody to the desired VMP peptide.

Following immunization, spleen cells are removed and fused, using a standard fusion protocol with plasmacytoma cells to produce hybridomas secreting monoclonal antibodies against VMP. Hybridomas which produce monoclonal antibodies to the selected antigens are identified using standard techniques, such as ELISA and Western blot methods. Hybridoma clones can then be cultured in liquid media and the culture supernatants purified to provide the VMP-specific monoclonal antibodies.

It is proposed that the monoclonal antibodies of the present invention will find useful application in standard immunochemical procedures, such as ELISA and Western blot methods, as well as other procedures which may utilize antibody specific to VMP epitopes.

Additionally, it is proposed that monoclonal antibodies specific to the particular polypeptide may be utilized in other useful applications. For example, their use in immunoabsorbent protocols may be useful in purifying native or recombinant VMP species or variants thereof.

In general, both poly- and monoclonal antibodies against VMP may be used in a variety of embodiments. For example, they may be employed in antibody cloning protocols to obtain cDNAs or genes encoding VMP or related proteins. They may also be used in inhibition studies to analyze the effects of VP in cells or animals. Anti-VMP antibodies will also be useful in immunolocalization studies to analyze the distribution of VMP peptides during various cellular events, for example, to determine the cellular or tissue-specific distribution of the VP peptide under different physiological conditions. A particularly useful application of such antibodies is in purifying native or recombinant VMP, for example, using an antibody affinity column. The operation of all such immunological techniques will be known to those of skill in the art in light of the present disclosure.

3.0 BRIEF DESCRIPTION OF THE DRAWINGS

FIG. 1A. Correlation of infectivity of *B. burgdorferi* B31 clones 5A1 through 5A10 with presence of a 28-kb linear plasmid (pBB28La). Plasmid profiles of B31 clones as determined by pulse-field gel electrophoresis and ethidium bromide staining. Low- (−) and high- (+) infectivity B31 clones have a virtually identical plasmid banding pattern by this method.

FIG. 1B. Correlation of infectivity of *B. burgdorferi* B31 clones 5A1 through 5A10 with presence of a 28-kb linear plasmid (pBB28La). Hybridization of a DNA blot of the gel shown in FIG. 1A with the pJRZ53 probe. The probe hybridized specifically with a 28-kb plasmid present in all 5 high-infectivity clones but in only 1 of 4 low-infectivity clones. Molecular sizes of the standards are indicated in kilobases, and an asterisk marks the location of pBB28La in the ethidium bromide-stained plasmid profile.

FIG. 2A. Structure of the vls locus of *B. burgdorferi* clone B31-5A3. Diagrammatic illustration of the overall arrangement of the vls locus in *B. burgdorferi* plasmid pBB28La. Distances from the left telomere are indicated in kb, and the locations of the subtractive hybridization clone pJRZ53 and the λDASH-Bb12 inserts are shown.

Figure 2B:
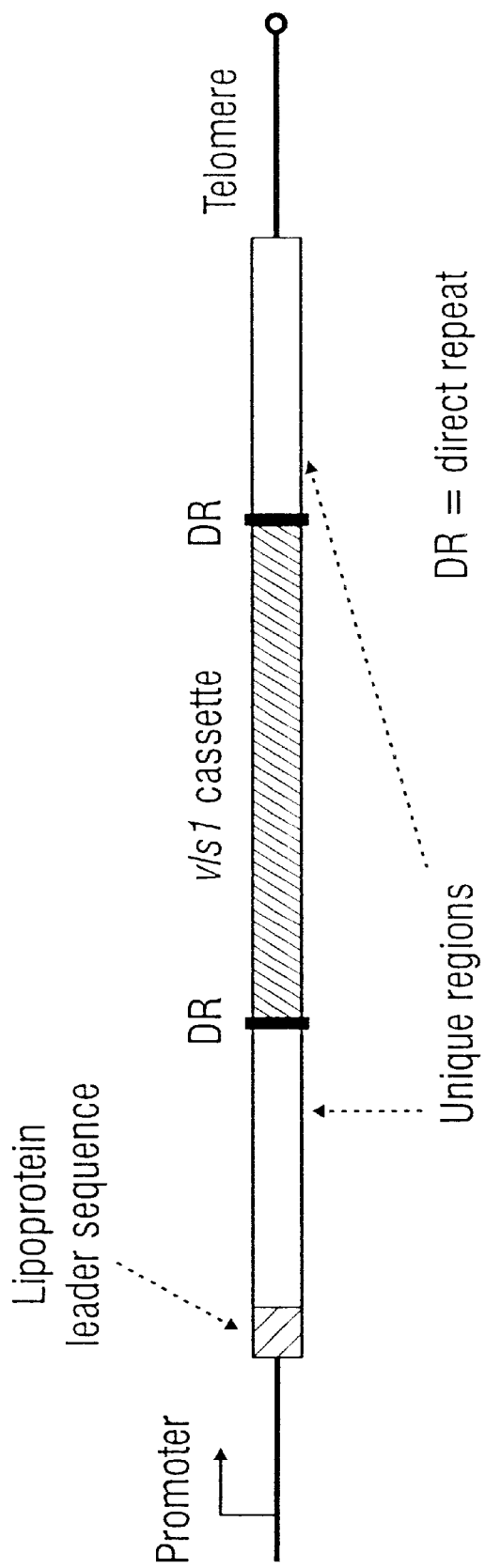

FIG. 2B. Structure of the vls locus of *B. burgdorferi* clone B31-5A3. Structure of vlsE.

FIG. 2C. Structure of the vls locus of *B. burgdorferi* clone B31-5A3. Structure of vlsE. Nucleotide and predicted amino acid sequences of the allele vlsE1 of the *B. burgdorferi* B31-5A3 vlsE gene. The predicted −10 and −35 promoter sequences, the putative ribosome binding site (RBS), and primers used for PCR™ and RT-PCR™ are marked. FIG. 2C shows the nucleotide and amino acid sequences of SEQ ID NO:1 and SEQ ID NO:2, respectively.

FIG. 3A. Sequence similarity of the predicted VlsE sequence (allele VlsE1) with the variable major proteins (Vmps) of *B. hermsii* and the predicted amino acid sequences of the silent vls cassettes. Alignment of the predicted amino acid sequence of VlsE (allele VlsE1) with that of Vmp17 (GenBank entry L04788; SEQ ID NO: 50). Identical amino acid residues are indicated by vertical lines (|) and similar residues are marked with colons (:) and periods (.). FIG. 3A upper sequence shows the amino acid sequences of SEQ ID NO:13, while the bottom sequence corresponds to SEQ ID NO:14.

FIG. 3B. Sequence similarity of the predicted VlsE sequence (allele VlsE1) with the variable major proteins (Vmps) of *B. hermsii* and the predicted amino acid sequences of the silent vls cassettes. Alignment of the deduced peptide sequences of 16 vls cassettes. Residues identical to the VlsE cassette region (Vls1) of *B. burgdorferi* are marked as dashes (−); similar amino acids are shown in lower case. Gaps and the predicted stop codons are indicated by dots (.) and asterisk (*), respectively. Variable regions VR-I though VR-VI are shaded. Vls1 corresponds to SEQ ID NO:15, Vls2 corresponds to SEQ ID NO:16, Vls3 corresponds to SEQ ID NO:17, Vls4 corresponds to SEQ ID NO:18, Vls5 corresponds to SEQ ID NO:19, Vls6 corresponds to SEQ ID NO:20, Vls7 corresponds to SEQ ID NO:21, Vls8 corresponds to SEQ ID NO:22, Vls9 corresponds to SEQ ID NO:23, Vls10 corresponds to SEQ ID NO:24, Vls11 corresponds to SEQ ID NO:25, Vls12 corresponds to SEQ ID NO:26, Vls13 corresponds to SEQ ID NO:27, Vls14 corresponds to SEQ ID NO:28, Vls15 corresponds to SEQ ID NO:29 and Vls16 corresponds to SEQ ID NO:30.

Figure 4A:
Figure 4B:

FIG. 4A. Surface localization of VlsE, as indicated by treatment of intact *B. burgdorferi* with proteinase K. Freshly cultured *B. burgdorferi* B31 clone 5A3 cells were incubated with (+) or without (−) proteinase K at room temperature for 10 min. The proteins of the washed organisms were then separated by SDS-PAGE. The protein blots were reacted with antiserum against the GST-Vls1 fusion protein;

FIG. 4B. Surface localization of VlsE, as indicated by treatment of intact *B. burgdorferi* with proteinase K. Freshly cultured *B. burgdorferi* B31 clone 5A3 cells were incubated with (+) or without (−) proteinase K at room temperature for 10 min. The proteins of the washed organisms were then separated by SDS-PAGE The protein blots were reacted with antiserum against *B. burgdorferi* B31 OspD.

Figure 4C:

FIG. 4C. Surface localization of VlsE, as indicated by treatment of intact *B. burgdorferi* with proteinase K. Freshly cultured *B. burgdorferi* B31 clone 5A3 cells were incubated with (+) or without (−) proteinase K at room temperature for 10 min. The proteins of the washed organisms were then separated by SDS-PAGE. The protein blots were reacted with monoclonal antibody H9724 against the *B. burgdorferi* flagellin (Fla).

FIG. 5A. Changes in deduced amino acid sequences of VlsE occurring during infection of C3H/HeN mice with *B. burgdorferi* B31-5A3. Flow chart of the overall experimental design.

Figure 5B:
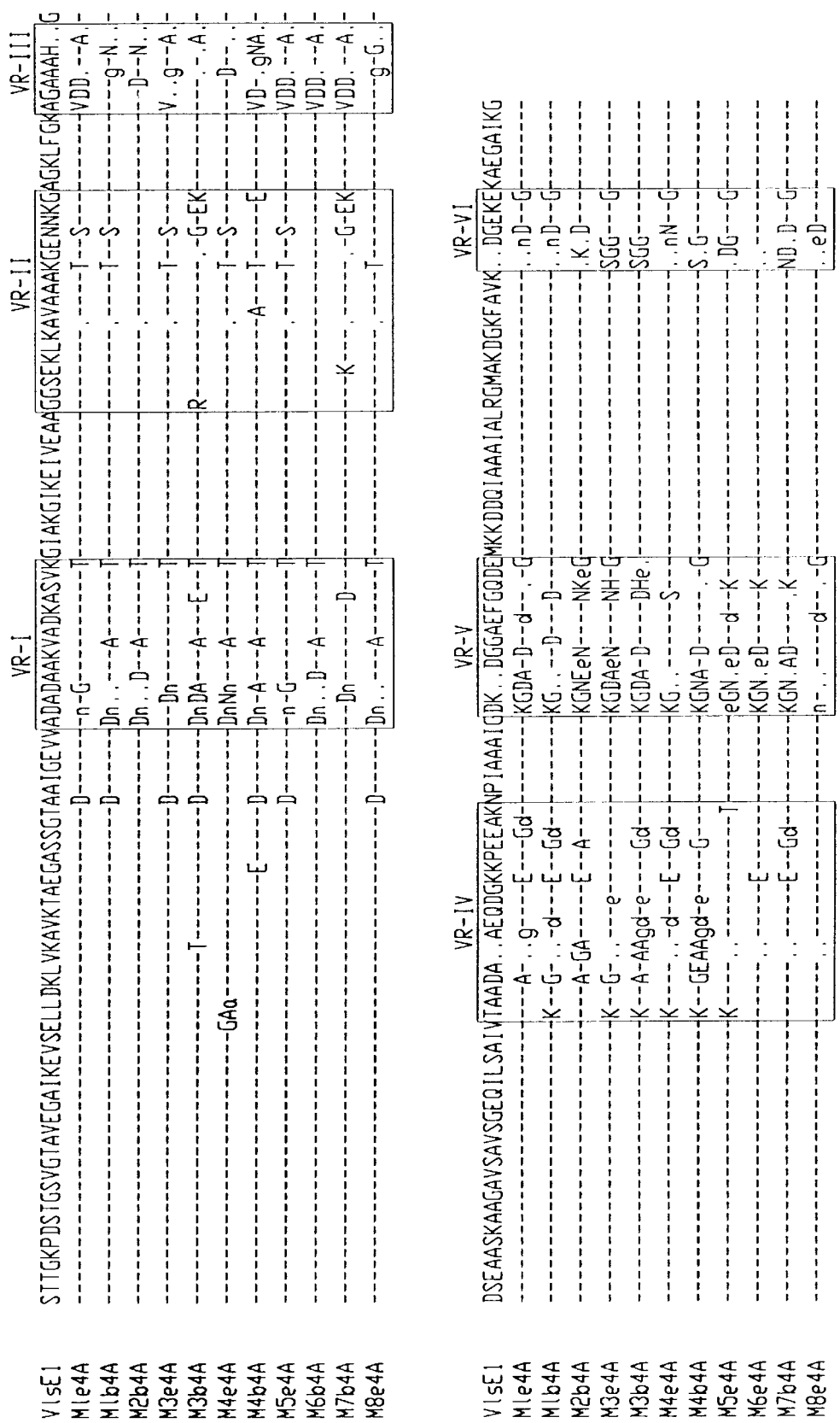

FIG. 5B. Changes in deduced amino acid sequences of VlsE occurring during infection of C3H/HeN mice with *B. burgdorferi* B31-5A3. Amino acid sequence alignment of the vlsE alleles in one clonal population from each of 11 different isolates. VlsE1 corresponds to SEQ ID NO:31, M1e4A corresponds to SEQ ID NO:32, M1b4A corresponds to SEQ ID NO:33, M2b4A corresponds to SEQ ID NO:34, M3e4A corresponds to SEQ ID NO:35, M3b4A corresponds to SEQ ID NO:36, M4e4A corresponds to SEQ ID NO:37, M4b4A corresponds to SEQ ID NO:38, M5e4A corresponds to SEQ ID NO:39, M6b4A corresponds to SEQ ID NO:40, M7b4A corresponds to SEQ ID NO:41 and M8e4A corresponds to SEQ ID NO:42.

Figure 5C:
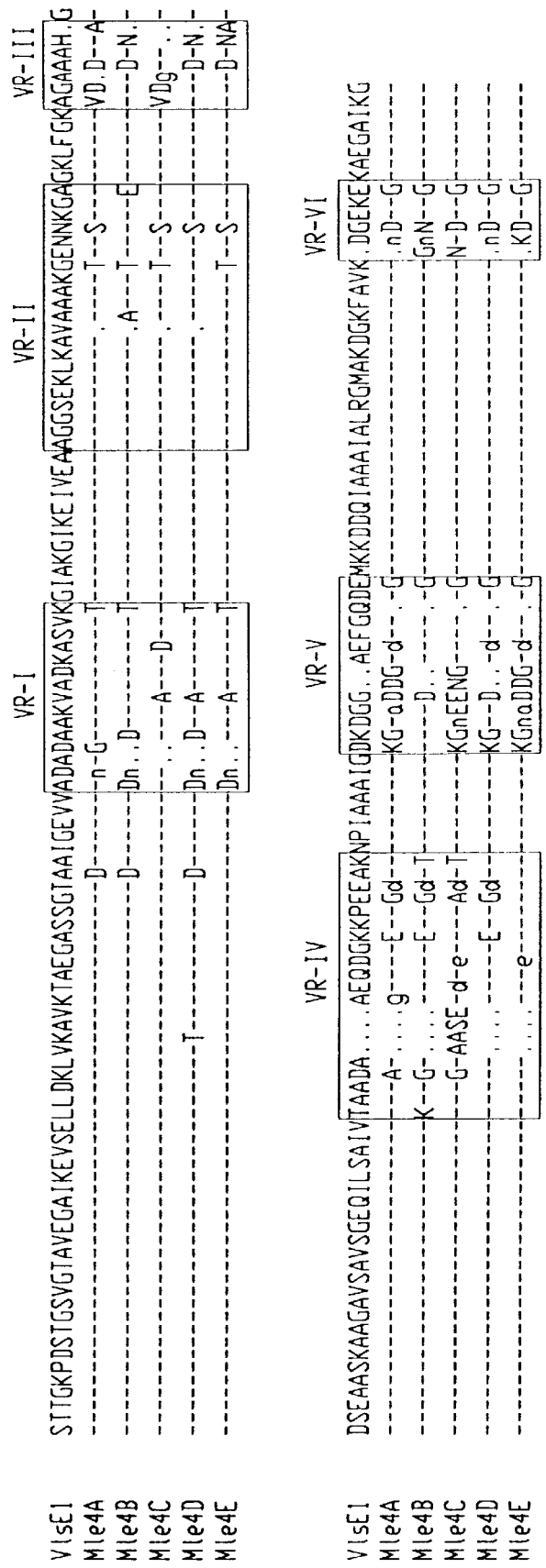

FIG. 5C. Changes in deduced amino acid sequences of VlsE occurring during infection of C3H/HeN mice with *B. burgdorferi* B31-5A3 Amino acid sequence alignment of the vlsE alleles in 5 clonal populations from a single ear isolate. In FIG. 5B and FIG. 5C, the deduced amino acid sequences of the mouse isolates were compared with those of the inoculating clone (VlsE1); similarity to this sequence is depicted as described in FIG. 3B. Amino acid residues (EGAIK) encoded by the 17-bp direct repeat are highlighted to indicate the boundaries of the vls cassette. VlsE1 corresponds to SEQ ID NO:43, M1e4A corresponds to SEQ ID NO:44, M1e4B corresponds to SEQ ID NO:45, M1e4C corresponds to SEQ ID NO:46, M1e4D corresponds to SEQ ID NO:47 and M1e4E corresponds to SEQ ID NO:48.

FIG. 6A. Altered VlsE antigenicity of *B. burgdorferi* clones (m1e4A through m8e4A) isolated from C3H/HeN mice 4 weeks post infection. The antigenic reactivties of 9 clones isolated from mice (lanes 109) were compared with those of the parental clone B31-5A3 used for mouse inoculation (lane 11) and the low-infectivity clone B31-5A2 (lane 10), which lacks the plasmid encoding VlsE. Two identical SDS-PAGE western blots were reacted with monoclonal antibody H9724 directed against the *B. burgdorferi* flagellin protein (Fla) as a positive control.

FIG. 6B. Altered VlsE antigenicity of *B. burgdorferi* clones (m1e4A through m8e4A) isolated from C3H/HeN mice 4 weeks post infection and antiserum against the GST-Vls1 fusion protein. Antiserum against the GST-Vls1 fusion protein. Prolonged exposures of the immunoblot against the GST-Vls1 futions protein indicated the presence of weakly reactive bands in all 9 mouse isolates. The relative locations of protein standards are indicated.

FIG. 6C. Reactivity of serum antibodies from a representative Mus musculus C3H/HeN mouse with VlsE. An immunoblot of *B. burgdorferi* proteins from the strains indicated and the GST-Vls1 fusion protein were reacted with serum from mouse 1 obtained 28 days after needle inoculation with $10^5$ *B. burgdorferi* B31, clone 5A3.

FIG. 6D. Reactivity of serum antibodies from a representative *Mus musculus* C3H/HeN mouse with VlsE. An immunoblot of *B. burgdorferi* proteins from the strains indicated and the GST-Vls1 fusion protein were reacted with serum from a Peromyscus leukopcus mouse infected with *B. burgdorferi* B31 via tick-bite. The protein bands corresponding to VlsE and the SGT-Vls1 fusion protein (as determined by reactivity with anti-GST-Vls1 antiserum; data not shown) are indicated by arrows. The relative locations of protein standards are shown in kilodaltons.

FIG. 6E. Reactivity of serum antibodies from a representative *Mus musculus* C3H/HeN mouse with VlsE. An immunoblot of *B. burgdorferi* [proteins from the strains indicated and the GST-Vls1 fusion protein were reacted with serum from an early stage Lyme disease patient. The protein bands corresponding to VlsE and the GST-Vls1 fusion protein (as determined by reactivity with anti-GST-Vls1 antiserum; data not shown) are indicated by arrows. The relative locations of protein standards are shown in kilodaltons.

Figure 7:
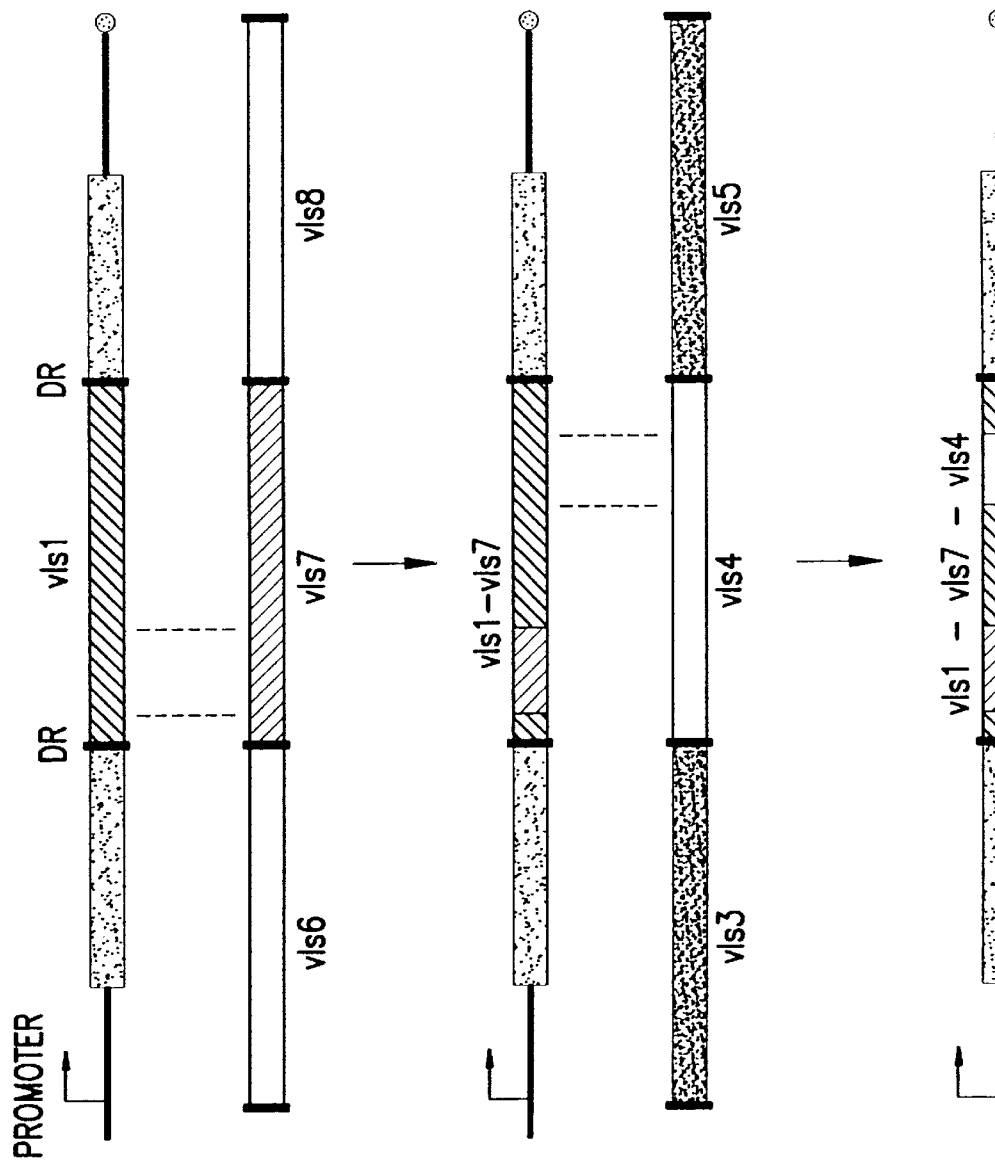

FIG. 7. Proposed model for genetic and antigenic variation at the vls locus. Recombination of segments of the silent vls cassettes vls7 and vls4 into the vls1 cassette of *B. burgdorferi* B31-5A3 vlsE gene is shown. A series of similar recombination events would generate unique vlsE alleles consisting of a mosaic of segments from several different silent vls cassettes.

4.0 DETAILED DESCRIPTION OF ILLUSTRATIVE EMBODIMENTS

The present work discloses the identification and characterization of an elaborate genetic system in the Lyme disease spirochete *Borrelia burgdorferi* that promotes extensive antigenic variation of a surface-exposed lipoprotein, VlsE. A 28-kilobase linear plasmid of *B. burgdorferi* B31 (pBB28La) was found to contain a vmp-like sequence (vls) locus that closely resembles the variable major protein (vmp) system for anti genic variation of relapsing fever organisms. Portions of several of the 15 non-expressed (silent) vls cassette sequences located upstream of vlsE recombined into the central vlsE cassette region during infection of C3H/HeN mice, resulting in antigenic variation of the expressed lipoprotein. The resulting combinatorial variation will potentially produce millions of unique antigenic variants and thereby contribute to immune evasion, long-term survival, and pathogenesis in the mammalian host.

An infectivity-associated 28-kb linear plasmid, pBB28La, in *B. burgdorferi* B31 by subtractive hybridization has been identified. DNA sequence analysis of cloned fragments from this plasmid revealed the vls locus consisting of 15 silent vls cassettes and an expressed vlsE gene. Subsequent infection studies demonstrated that promiscuous recombination occurs at the vlsE site in C3H/HeN mice. Although the vls locus has been characterized thoroughly only in one clonal population of *B. burgdorferi* B31, Southern hybridization results indicate that this locus is present in infectious strains of three well-defined Lyme disease Borreliae genospecies (*B. burgdorferi*, *B. afzelii*, and *B. garinii*), despite the overall genetic heterogeneity among these organisms (Casjens et al., 1995; Xu and Johnson, 1995).

The vls locus resembles the vmp system of *B. hermsii* in both sequence and genetic organization. There is some sequence homology between these two systems, particularly between the vlsE and large vmp genes. This is exemplified by direct sequence comparison between vlsE and vmp17, which have homology throughout their predicted amino acid sequences (FIG. 3A). The vlsE and silent vls cassettes also have a closer degree of homology to small vmps and *B. burgdorferi* ospC genes. Additionally, both the vls and vmp systems have a single expression site encoding a surface-localized lipoprotein, as well as multiple unexpressed sequences (Plasterk et al., 1985; Barbour et al., 1991a). Finally, the expression sites for both systems are located near one of the telomeres of their respective linear plasmids (Kitten and Barbour, 1990; Barbour et al., 1991b). These observations suggest that the vls locus may provide the Lyme disease Borreliae with the capability of antigenic variation analogous to the vmp system of *B. hermsii* (Barbour, 1993). The above similarities also indicate that the vlsE gene, silent vls cassettes, and large vmp genes of relapsing fever organisms, all evolved from a common ancestral gene. Their relatively high G+C compositions (e.g. 45% for vlsE and 37% for vmp17) when compared with Borrelia G+C content (~28%) are also consistent with this evolutionary relationship, and further suggest the possibility of lateral transfer from other organisms.

There are several differences between the vls and vmp systems. First, *B. hermsii* possesses at least two vmp-containing linear plasmids (Meier et al., 1985; Plasterk et al., 1985), whereas only one vls-containing linear plasmid was detected in Lyme disease Borreliae under hybridization conditions (FIGS. 1A and 1B). Second, the silent vmp genes are separated by intergenic noncoding regions and arranged in either orientation (Barbour et al., 1991a), but the silent vls cassettes are organized head-to-tail as a single open reading frame throughout almost the entire region (FIGS. 2A and 2B). Third, the silent vmp genes lack promoter sequences, but most encode complete or nearly complete open reading frames with their own ribosome-binding sites (Barbour et al., 1991a). On the other hand, the vls cassettes represent only the central third of the expression site. Lastly, each phase of *B. hermsii* infection is caused predominantly by organisms expressing a single vmp allele (Meier et al., 1985; Plasterk et al., 1985), whereas a high degree of vlsE allelic variation occurs among organisms isolated even from a small ear biopsy specimen during *B. burgdorferi* infection (FIGS. 5A, 5B and 5C).

The sequence changes at the vlsE site may result from genetic recombination with sequences from the silent vls cassettes. Despite considerable sequence variations within the vls region of different vlsE alleles, the sequence examined outside the 17-bp direct repeats remained unchanged (FIG. 5B and FIG. 5C). Within the vls region, the changes are not random but are clustered predominantly in six highly variable regions found in 15 silent vls cassettes (FIG. 3B). Nearly all of the sequence variations observed in the mouse isolates are identical to portions of the silent vls cassettes, although the combinations of the sequence variations made each of these alleles unique.

The inventors have shown that *B. burgdorferi* undergoes an unusual type of genetic variation (FIG. 7): (i) the vls cassettes contain conserved and variable regions; (ii) the conserved sequences facilitate recombination between the expressed and silent vls sequences, probably by a non-reciprocal gene conversion mechanism; (iii) the conserved 17-bp direct repeat sequences may be involved in alignment of the vls sequences during recombination or in binding of proposed site-specific recombinase(s); (iv) through multiple recombination events, portions of the expression site are replaced by segments from several silent vls cassettes, resulting in a vast array of potential vlsE alleles; and (v) the site-specific mechanism is activated in vivo, resulting in a high rate of recombination. Since both the vlsE and silent vls cassettes are located on the same linear plasmid, pBB28La, in *B. burgdorferi* (FIG. 2A), intraplasmic recombination is likely to be involved. However, it is also possible that interplasmic recombination of multiple copies of the pBB28La plasmid are present in each organism, as shown with the vmp-encoding plasmids of *B. hermsii* (Kitten and Barbour, 1992).

Genetic variation involved in multi-gene families has been described in several other pathogenic microorganisms (Borst and Geaves, 1987; Borst et al., 1995; Donelson, 1995). In the context of combinatorial recombination, the genetic variation at the vlsE site is similar to that of the pilin-encoding genes of N. Gonorrhoeae (Seifert and So, 1988). The gonococcal pilus is primarily composed of repeating subunits of an 18-kilodalton pilin protein and is required for adherence of the bacterium to a variety of human cells (Swanson and Koomey, 1989). While the complete pilin genes are expressed only at two expression sites (pilE1 and pilE2), multiple silent copies (pilS) containing portions of the pilin genes are found over a wide range on the gonococcal chromosome (Haas and Meyer, 1986). Through multiple combinatorial recombination events, a single gonococcal clone expressing one pilin stereotype can give rise to a large number of progeny that express antigenically distinctive pilin variants (Meyer et al., 1982; Hagblom et al., 1985; Segal et al., 1986). The recombination between the expression and silent loci occurs predominantly through a non-reciprocal gene conversion mechanism (Haas and Meyer, 1986; Koomey et al., 1987).

The coding sequences of the Neisseria pilin variants are divided into constant, semi-variable, and hypervariable regions (Haas and Meyer, 1986), which are analogous to the conserved and variable regions of the vls cassettes (FIG. 3B, FIG. 5B and FIG. 5C). The constant regions and a conserved DNA sequence (Sma/Cla repeat) located at the 3' end of all pilin loci are though to pair the regions involved in recombination events (Wainwright et al., 1994). In this context, the 17-bp direct repeats (FIG. 2C) and the conserved regions (FIG. 3B) of the vls cassettes may play a similar role in recombination events. The silent loci of gonococcal pilin genes contain different regions of the complete pilin genes (Haas and Meyer, 1986), whereas the silent vls cassettes of *B. burgdorferi* represent only the central cassette region of the vlsE gene (FIG. 3B).

Non-reciprocal recombinations also occurs between the expressed and the silent genes encoding variant surface glycoproteins (Vsgs) in African trypanosomes (Donelson, 1995). Based on similarities between the vls locus and the multi-gene families of the other pathogenic microorganisms, it is likely that a unidirectional gene conversion mechanism is also active in the vls locus. However, there is not as yet any data regarding the preservation of the silent vls cassettes, and the exact mechanism of vls recombination remains to be determined.

There is strong evidence that genetic variation at the vls locus generates antigenic variation. The prolific recombination at the vlsE site in C3H/HeN mice supports the possibility of antigenic variation in Lyme diseases caused by Borreliae. The decreased reactivity to antibody against the parental Vls1 cassette region among the clonal populations of mouse isolates demonstrates that genetic variation at the vlsE site resulted in changes in antigenicity of the VlsE variants (FIG. 6B). Finally, C3H/HeN mice infected with *B. burgdorferi* produced strong antibody responses against the parental VlsE protein, but consistent with the results obtained with the antibody against the GST-Vls1 fusion protein, the same antisera had decreased reactivities with some of the VlsE variants isolated from mice (FIG. 6C). Since VlsE is a surface-exposed lipoprotein, as indicated by proteinase K digestion (FIGS. 4A and 4B) and [$^3$H]-palmitate radiolabeling studies, this proposed antigenic variation may allow Lyme disease Borreliae to survive immune attack targeted against VlsE.

Variation of *B. burgdorferi* surface proteins such as VlsE may also affect the organism's virulence and its ability to adapt to different micro-environments during infection of the mammalian host. Recent studies of a *Borrelia turicatae* mouse infection model that resembles Lyme disease showed that one serotype expressing VmpB exhibited more severe arthritic manifestations, whereas another expressing VmpA had more severe central nervous system involvement (Cadavid et al., 1994). The numbers of Borreliae present in the joints and blood of serotype B-infected mice were much higher than those of mice infected with serotype A. consistent with a relationship between Vmp serotype and disease severity (Pennington et al. 1997). Antigenic variation of Neisseria pilin (Lambden et al., 1980; Rudel et al., 1992; Nassif et al., 1993; Jonsson et al., 1994) and Opa proteins (Kupsch et al., 1993) is known to affect adherence of the organisms to human leukocytes and epithelial cells.

The importance of the vls-containing plasmid, pBB28La, during infection is supported by the following evidence: (i) all high-infectivity clones and strains tested thus far contain the vls-containing plasmid pBB28La, and loss of this plasmid correlates with a decrease in infectivity (FIG. 1B); (ii) pBB28La was maintained in all animal isolates tested thus far; and (iii) the vls sequences are preserved among three Lyme disease genospecies despite their genetic heterogeneity (Casjens et al., 1995) and diversity in plasmid profiles (Xu and Johnson, 1995). On the other hand, *B. burgdorferi* clones with or without plasmid pBB28La showed similar growth rates in culture medium. In addition, pBB28La is readily lost during in vitro subcultures as early as passage 5. Therefore, presence of pBB28La appears to have little if any effect on in vitro growth, yet has a profound effect on the ability to infect mammalian host.

VlsE (or, potentially, other genes encoded by pBB28La) appears to have another important but undefined function which is unrelated to antigenic variation. Low-infectivity clones lacking the vls-encoding plasmid pBB28La do not propagate in severe combined immunodeficiency (SCID) mice, indicating that the required factor(s) provides an important function unrelated to evasion of the adaptive immune system. Also, in vivo selection against Bb clones lacking pBB28La appears to occur early in infection (within the first week), before the adaptive immune response would be expected to exert significant selection pressure. Therefore, it is likely that VlsE plays an important role in some aspect of infection (e.g. colonization, dissemination, adherence, extravasation, evasion of innate immune mechanisms, or nutrient acquisition), and that antigenic variation merely permits surface expression of this protein without leading to elimination of the bacteria by the host's immune response. Retention of this activity would require that the variation in amino acid sequences would not interfere with the active site(s) of the protein; this requirement may explain the existence of highly conserved regions at the N- and C-termini and within the vls cassette. Sequence variation as a mechanism of maintaining surface protein function in the face of a hostile immune response may be a strategy common to pathogenic microorganisms.

4.1 Antigenic Variation in *B. hermsii*

A complex antigenic variation mechanism has been characterized in *Borrelia hermsii*, a relative of *B. burgdorferi* that causes relapsing fever (Balmelii and Piffatetti, 1996; Barbour, 1993; Donelson, 1995). Surface-exposed lipoproteins called variable major proteins (Vmps) are encoded by homologous genes located in 28- to 32-kb linear plasmids with covalently closed telomeres (Barbour and Garon, 1987; Kitten and Barbour, 1990). The vmp genes have been subdivided into two groups: small and large (Restrepo et al., 1992). Large vmp genes such as vmp7 and vmp17 and small vmp genes such as vmp1 and vmp3 are approximately 1 kb and 0.6 kb in size, respectively. Each organism contains both small and large vmp genes in a unexpressed (silent) form in the so-called storage plasmids (Plasterk et al., 1985). Only one vmp gene located near one of the telomeres of a different plasmid (called the expression plasmid) is expressed in each organism (Kitten and Barbour, 1990; Barbour et al., 1991a). Antigenic variation occurs when the expressed vmp is replaced completely or partially by one of the silent vmp genes at the telomeric expression site through interplasmic recombination (Meier et al., 1985; Plasterk et al., 1985; Barbour et al., 1991b), intraplasmic recombination (Restrepo et al., 1994), and post-switch rearrangement (Restrepo and Barbour, 1994). The antigenic switch occurs spontaneously at a frequency of $10^{-3}$ to $10^{-4}$ per generation (Stoenner et al., 1982).

4.2 Identification of vls

A genetic locus (called vmp-like sequence or vls) has been identified and characterized in *B. burgdorferi* that surprisingly resembles the vmp system of *B. hermsii*. A vls expression site (vlsE) and 15 additional silent vls cassettes were identified on a 28-kb linear plasmid (designated pBB28La). The presence of pBB28La correlates with the high-infectivity phenotype in *B. burgdorferi* sensu lato strains tested. vlsE, located near a telomere of pBB28La, encodes a surface-exposed lipoprotein. Examination of ear and blood isolates from C3H/HeN mice infected 4 weeks previously with B31 clone 5A3 demonstrated the occurrence of promiscuous recombination at the vlsE site, such that each of *B. burgdorferi* clones examined was unique and appeared to have undergone multiple recombination events with portions of the silent vls cassettes. The resultant VlsE variants exhibited a decreased reactivity to antiserum directed against the parental Vls1 cassette region. This elaborate genetic system permits combinatorial antigenic variation of vlsE in the mammalian host, thereby contributing to evasion of the immune response and long-term survival in the mammalian host.

The present invention illustrates the rapid occurrence of promiscuous recombination at the vls expression site (vlsE), resulting in a combinatorial form of genetic and antigenic variation at the vlsE site. Antigenic variation at the vls site has been detected using an in vivo selection approach.

The sequence variation appears to lead to significant antigenic variation. Rabbit antiserum raised against a vls1-GST fusion protein reacted strongly with the original *B. burgdorferi* clone (B31 5A3), but did not react with several of the clones reisolated from mice 4 weeks post infection.

*B. burgdorferi* induces a site-specific recombination mechanism during infection of the mammalian host. The vlsE cassette sequence in each of the mouse isolates is unique. At the nucleotide level each vlsE cassette is comprised of regions identical to several of the silent vls cassettes. This promiscuous recombination of silent vls cassette segments causes a combinatorial diversity at the vlsE expression site, similar to the diversity possible in the immunoglobulin and T cell-receptor variable regions. In contrast, antigenic variation in relapsing fever organisms usually involves replacement of the entire gene at the expression site with one of the 'silent' VMP genes Moreover, a single VMP serotype is predominant during each relapse.

This mechanism of genetic switching appears to be different from any other antigenic variation mechanism described in bacteria or protozoa and has important implications in Lyme disease. By combining different regions of the silent vls cassettes, it is possible for many different VlsE 'serotypes' to coexist in the same patient. It may be impossible for the host to mount a protective response against any one of these clonal populations, because of the small number of each type. Even mounting a response against one serotype would not protect against rapidly evolving, new serotypes. The fact that *B. burgdorferi* has evolved such an elaborate mechanism for varying the sequence of VlsE indicates the importance of the protein in pathogenesis and/or immune evasion.

The present invention discloses a repetitive DNA sequence ~500 bp in length which is present in multiple, nonidentical copies in a 28 kb linear plasmid of infectious *Borrelia burgdorferi*, the causative agent of Lyme disease. These DNA sequences encode polypeptides which have sequence similarity to the Variable Major Proteins (VMPs) of relapsing fever Borreliae (such as *B. hermsii*). VMPs are highly antigenic surface proteins which the relapsing fever Borreliae are able to change through a genetic recombination mechanism, thereby evading the immune response. Antibodies against a particular VMP are protective, resulting in rapid clearance of bacteria of the corresponding serotype. In *B. burgdorferi*, VMP-like sequences (vls) are present on a 28 kb linear plasmid, and this plasmid appears to encode virulence factor(s) required for infectivity. The sequence of a 16 kb region of this plasmid contains at least 20 copies of the VMP-like sequence.

The inventors have identified genes and gene products that appear to be important in the infectivity and pathogenesis of *B. burgdorferi*. In previous studies (Norris et al., 1995), it was shown that clonal populations of *B. burgdorferi* isolated after 5 to 15 in vitro passages varied significantly in their infectivity in the C3H/HeN mouse model. So-called high-infectivity and low-infectivity clones differed by 500-fold in their median infectious dose ($1.8 \times 10^2$ vs. $1 \times 10^5$), yet exhibited no obvious differences in terms of protein content (as determined by two dimensional gel electrophoresis and silver staining) or plasmid content (determined by agarose gel electrophoresis and ethidium bromide staining). However, by using subtractive hybridization between DNA of high- and low-infectivity organisms, specific sequences that differed between the two types have been identified. These sequences have been characterized as VMP-like sequences (vls), now identified for the first time in *B. burgdorferi*.

In initial studies, high-passage (HP) and low-passage (LP) uncloned populations of *B. burgdorferi* strain B31 were used as a source of DNA for subtractive hybridization. HP B31 was cultured in vitro for ~1,000 passages and found to be noninfectious, whereas LP B31 passages in vitro ~5 times remains infectious in the C3H/HeN mouse model. The plasmid DNA of each strain was purified. The DNA of HP B31 was randomly sheared by ultrasonication, whereas the DNA of LP B31 was digested to completion with the restriction enzyme Sau3AI. The DNA of the two strains was denatured by heating to 100° C., mixed at a ratio of 50:1 HP DNA to LP DNA, and allowed to hybridize with the sheared HP DNA; as a result, the Sau3AI restriction sites were not regenerated. Unique segments of the LP DNA tend to hybridize with the complementary LP DNA strand, and the Sau3AI "sticky ends" are regenerated. A portion of the hybridized mixture was ligated into pBluescript II SK- (Stratagene) that had been treated previously with BamHI and alkaline phosphatase. The ligated preparation was used to transform *E. coli* XL-1 Blue cells, and transformants were selected by plating the bacteria on Luria broth (LB) agar plates containing ampicillin and isopropyl thiogalactopyranoside (IPTG) and 5-bromo-4-chloro-3-indolyl-D-galactoside (X-gal). Any resulting white colonies (*E. coli* containing a plasmid with a DNA insert) were selected for further study and sequence analysis.

One of the resulting recombinant plasmids, designated pJRZ53, contained DNA encoding a single, contiguous open reading frame (ORF) 562 bp in length. The deduced amino acid sequence of this ORF had significant homology with Vmp proteins of *B. hermsii*, most notably Vmp17, Vmp21, Vmp7, and Vmp25 (27.2 to 20.3% identity, 50.0 to 56.8% similarity). Hybridization of pJRZ53 with Southern blots of *B. burgdorferi* plasmids showed that this VMP-like DNA sequence was localized on a 28 kb linear plasmid.

Additional DNA recombinants containing sequences hybridizing with pJRZ53 were derived from a PstI library of *B. burgdorferi* B31 plasmid DNA. *B. burgdorferi* B31 plasmid DNA was treated with several restriction enzymes to determine the best combination for cloning a larger fragment containing the pJYZ53 sequence. Surprisingly, numerous bands hybridizing with the pJRZ53 probe were present in DNA digested with PstI, RsaI, Sau3AI and other enzymes. This result demonstrated that multiple sequences resembling the pJRZ53 insert were present in the 28 kb plasmid.

Several additional recombinant clones were obtained by treating *B. burgdorferi* plasmid DNA with PstI, ligating the fragments into pBluescript II SK-, transforming *E. coli* with the resulting recombinants, and screening the library for hybridization with the pHRZ53. Sequence determinations of these recombinant clones confirmed the presence of multiple sequences that were highly homologous but nonidentical to the pHRZ53 sequence. This homology at the DNA and protein levels is exemplified by the comparison of the two contiguous repeats found in pHRZ53-31, an independently derived 1143 bp PstI clone that overlaps the pJRZ53 sequence. Alignment of the 5' and 3' regions of pJRZ53-31 shows highly homologous repeats in the DNA sequence of recombinant clone pJRZ53-31. The DNA sequence from the 5' (nt 1-578) and 3' (nt 579-1143) regions were aligned using the GCG program GAP There is 93% identity between the 5' and 3' regions. The deduced amino acid sequences of the DNA regions were aligned using the GCG program GAP. The overall sequence similarity and identity are 92% and 85%, respectively.

Subsequent studies used clonal populations of *B. burgdorferi* obtained by subsurface colony formation of passage 5 organisms on agar plates (Norris et al., 1995). These clones were characterized in terms of infectivity, and were subdivided into high-infectivity and low-infectivity phenotypes. pJRZ53 hybridized with a 28 kb band in 6/9 B31 clones and 7/10 Sh2-2-82 clones. All 12 highly infectious clones contained the plasmid, whereas 6 of 7 low infectivity clones lacked the plasmid (Table 2). There was correlation of the presence of a 28 kb plasmid containing the pJRZ53 sequence with infectivity of *B. burgdorferi* clonal populations. Genomic DNA preparations from 10 Sh2-2-82 clones and 9 B31 clones (Norris et al., 1995) were subjected to pulsed field gel electrophoresis and transferred to nylon membranes. The 562 bp pJRZ53 insert labeled with $^{32}$P was hybridized to the Southern blots. Controls consisted of uncloned populations of high-passage, noninfectious B31 (−) and low-passage, infectious B31 (+). All high infectivity clones (+) possessed a 28 kb plasmid that hybridized with pJRZ53, whereas only 1/7 low-infectivity clones (−) had the plasmid.

Thus there is a strong correlation between the presence of the 28 kb plasmid and infectivity. Plasmid profiles in the same gels used for Southern blot hybridization did not reveal any difference in ethidium bromide staining in the region of the 28 kb plasmid, due to the presence of several other comigrating plasmids. The one low infectivity clone that contained the plasmid may lack a functional gene or genes encoding other virulence factors.

TABLE 2

Correlation Between Infectivity and the Presence of the 28 kb Linear Plasmid Hybridizing with the pJRZ53 Sequence

| Clonal Populations | Number of clones containing the 28 kb plasmid/total |
| --- | --- |
| B31, high infectivity | 5/5 |
| B31, low infectivity | 1/4 |
| Sh2, high infectivity | 7/7 |
| Sh2, low infectivity | 0/3 |

A map of the 28 kb linear plasmid (designated pBb28L) showed a 16 kb fragment of pBb28L of the bacterial clone B31-5A3 had been cloned into the vector lambda Dash II (Stratagene, LaJolla, Calif.). Briefly, a preparation of plasmid DNA was treated with S1 nuclease to disrupt the covalently closed ends (telomeres) of the linear plasmids. After treatment with Klenow fragment of DNA polymerase, an oligonucleotide linker containing an EcoRI site was ligated onto the ends. The preparation was then treated with EcoRI (to cleave the DNA both at the linker and at a previously mapped internal EcoRI site) and ligated into the EcoRI site of lambda Dash II. Clones containing the pJRZ53 sequence were identified by hybridization, and included two overlapping clones 12 kb and 16 kb in length. Partial sequence analysis of the sequence of the 16 kb fragment revealed the presence of at least 17 VMP-like sequences within this region.

Over 9,500 bp of DNA sequence from the *B. burgdorferi* DNA insert in Lambda DashII Clone 12-1 have been obtained. This sequence was determined through automated sequence analysis (using T3, T7, and internal primers) of DashII 12-1 itself, as well as of portions of 12-1 cloned into pBluescript using fragments obtained by random DNaseI-mediated cleavage or by digestion with PstI or RsaI. Sequences were assembled using the GCG program Gelassemble and have an average redundancy of ~4 fold. The high degree of sequence identity among different regions required careful verification of sequence differences and manual alignment of sequences in some instances.

The sequences obtained indicate the presence of at least one open reading frame representing an expression site (vlsE1) and at least 16 additional nonidentical, apparently 'silent' (nonexpressed) vls cassettes. A consensus ribosome binding site (RBS, underlined) is located 8 nucleotides (nt) upstream of the predicted translational start site at nt 75–77. The predicted product, VlsE1, has a molecular weight of 35,881 kDa. The first 19 amino acids of the predicted N-terminus contain a possible signal peptide sequence, with a motif of a charged N-terminus, a hydrophobic region, and a potential signal peptidase II cleavage site (FINC, double-underlined) resembling those found in other Borrelial lipoproteins. The predicted polypeptide size after cleavage at this site is 33,957 kDa, and the predicted isoelectric point is 7.3. Except for the signal peptide, the predicted protein is largely hydrophilic. The putative stop codon is located at nt 1143–1145, only 82 nt from the telomeric end of pBb28L.

Expression of vlsE1 in the high infectivity *B. burgdorferi* B31 Clone 3 was verified by Northern blot analysis and reverse transcriptase polymerase chain reaction (RT-PCR™). Hybridization of radiolabelled pJRZ53 insert to blots of RNA separated by agarose electrophoresis indicated the presence of a transcript containing a homologous sequence. For RT-PCR™, primers corresponding to nt 835–857 (plus strand) and nt 1010–1032 (minus strand) of the sequence in FIG. 2C were constructed. The minus strand primer was used in combination with AMV reverse transcriptase and RNA isolated from B31 clone 3 to produce a cDNA product. The cDNA was then amplified by standard PCR™ using the plus and minus primers, resulting in a 198 bp product detectable by ethidium bromide staining of agarose gels. The PCR™ product was ligated into the pCRII vector (Invitrogen), and three independently-derived clones yielded sequences identical to that shown in SEQ ID NO:1 and SEQ ID NO:3. Control preparations consisted of reactions identical except for the omission of reverse transcriptase; no product was detected. This result demonstrated that vlsE1 is transcribed in *B. burgdorferi* B31 Clone 3 organisms.

The DNA sequence of a proposed 'storage site' contains at least 15 contiguous copies of the vls sequence of SEQ ID NO:1 and SEQ ID NO:3. The beginning and end of each vls 'cassette' was selected to match the repetitive sequence (vls1) in vlsE1. The vls cassettes identified thus far range from 474 to 582 nt in length; length variation is primarily due to short insertions or deletions in multiples of three nucleotides, indicating selective preservation of the open reading frames. Longer deletions are seen in vls7, vls8, and vls10. vls14 and vls16 each contain one frameshift, and vls11 contains one stop codon. Otherwise, the 7766 bp sequence of SEQ ID NO:1 and SEQ ID NO:3 represents one contiguous open reading frame.

The vls cassettes exhibit a remarkable degree of sequence conservation at both the DNA and encoded amino acid levels, see FIGS. Nucleotide sequences of *B. burgdorferi* B31 vls were aligned using the GCG program PILEUP. vls1 corresponds to nt 420–1003 in the sequence of FIG. 4 and FIG. 5. When compared to vls1 using GCG program GAP, the vls sequences have 90.0% to 96.1% nucleotide sequence identity (FIG. 6), and 76.9% to 91.4% predicted amino acid sequence identity (FIG. 7). None of the vls copies identified thus far have complete sequence identity, but all are closely related.

Table 3 shows the vls segments identified and indicates the positions at which the segments may be found as part of SEQ ID NO:1 and SEQ ID NO:3. Repeat recombinant segments are identified as "repeats".

TABLE 3

| CASSETTE (vls) | POSITION IN SEQ ID NO: 3 | REPEAT position in SEQ ID NO: 3 |
| --- | --- | --- |
| vls 2 | <205>-711 (truncated at 5' end) | 711–727 |
| vls 3 | 712–1293 | 1293–1309 |
| vls 4 | 1294–1869 | 1869–1885 |
| vls 5 | 1870–2439 | 2439–2456 |
| vls 6 | 2440–3009 | 3009–3025 |
| vls 7 | 3010–3483 | 3483–3499 |
| vls 8 | 3484–3990 | 3990–4006 |
| vls 9 | 3991–4548 | 4548–4557 |
| vls 10 | 4549–5058 | 5058–5074 |
| vls 11 | 5059–5652 | 5652–5668 |
| vls 12 | 4653–6219 | 6219–6253 |
| vls 13 | 6220–6789 | 6789–6805 |
| vls 14 | 6846–7373 | 7373–7389 |
| vls 15 | 7274–7946 | 7946–7962 |
| vls 16 | 7947–8000 | |

The degree of sequence similarity between the VMP-like sequences and *B. hermsii* VMP proteins were exemplified by an alignment of the predicted translation product of vlsE1 with some of the most similar VMP sequences (vmp 17, vmp 21, vmp7). Regions of similarity are interspersed among areas of low sequence identity. The G+C contents of the *B. burgdorferi* VMP-like sequences are quite high (e.g., 49.9% for pJRZ53-31) as compared to the genomic *B. burgdorferi* G+C content (27 to 30%) or that of *B. hermsii* VMP genes (e.g., 37% for vmp17). The sequence similarity at the protein level may be due to divergent or convergent evolution. It is also possible that the VMP-like sequences were acquired from another organism, given the different G+C content.

Alignment of either the DNA sequences or the deduced amino acid sequences of the open reading frames reveals the presence of both conserved and variable regions of the repetitive sequence. The conserved sequences may represent 'framework' regions important in the overall structure of the polypeptides, whereas the variable sequences may produce different epitopes. It is contemplated that protective antibodies can be produced against either the conserved or variable portions of the putative amino acid sequences.

The expressed copy of vls (vlsE1) has been identified and sequenced. A segment of the vlsE gene corresponding to the cassette region has been subcloned into the pGEX-2T expression vector, and the resulting GST-vls1 fusion protein product produced and purified. Antibodies against the recombinant protein have been used for identification of the native protein in SDS-PAGE and two dimensional gel electrophoresis patterns of *B. burgdorferi* proteins by immunoblotting. Infected patients and animals produced antibodies against the protein which were detected by immunoblot analysis using the recombinant protein as antigen (FIGS. 6C, 6D and 6E). In addition, the purified recombinant protein may be used for immunization of mice and other animals to determine whether antibodies or cellular responses against the protein are protective against infection with *B. burgdorferi* and other Lyme disease Borreliae. Such animal studies would determine the feasibility of vaccination of humans and animals with Vls protein sequences or DNA sequences for immunoprophylaxis.

4.3 ELISAs

ELISAs may be used in conjunction with the invention. In an ELISA assay, proteins or peptides incorporating Borrelia VMP-like antigenic sequences are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of powdered milk. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

Following formation of specific immunocomplexes between the test sample and the bound antigen, and subsequent washing, the occurrence and even amount of immunocomplex formation may be determined by subjecting same to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a urease, alkaline phosphatase or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

4.4 Epitopic Core Sequences

The present invention is also directed to protein or peptide compositions, free from total cells and other peptides, which comprise a purified protein or peptide which incorporates an epitope that is immunologically cross-reactive with one or more anti-Borrelia VMP-like antibodies.

As used herein, the term "incorporating an epitope(s) that is immunologically cross-reactive with one or more anti-VMP-like antibodies" is intended to refer to a peptide or protein antigen which includes a primary, secondary or tertiary structure similar to an epitope located within a Borrelia VMP-like polypeptide. The level of similarity will generally be to such a degree that monoclonal or polyclonal antibodies directed against the Borrelia VMP-like polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of Borrelia VMP-like epitopes, and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of about 5 to about 25 amino acids in length, and more preferably about 8 to about 20 amino acids in length. It is proposed that shorter antigenic Borrelia VMP-like-derived peptide sequences will provide advantages in certain circumstances, for example, in the preparation of vaccines or in immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to Borrelia VMP-like and Borrelia VMP-like-related sequences. It is proposed that these regions represent those which are most likely to promote T-cell or B-cell stimulation in an animal, and, hence, elicit specific antibody production in such an animal.

An epitopic core sequence, as used herein, is a relatively short stretch of amino acids that is "complementary" to, and therefore will bind, antigen binding sites on transferring-binding protein antibodies. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence expected by the present disclosure would generally be on the order of about 5 amino acids in length, with sequences on the order of 8 or 25 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson and Wolf, 1988; Wolf et al., 1988). Computerized peptide sequence analysis programs (e.g., DNAStar® software, DNAStar, Inc., Madison, Wis.) may also be useful in designing synthetic Borrelia VMP-like peptides and peptide analogs in accordance with the present disclosure.

Syntheses of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquoted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

4.5 Immunoprecipitation

The antibodies of the present invention are particularly useful for the isolation of antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Nonionic salts are preferred, since other agents such as bile salts, precipitate at acid pH or in the presence of bivalent cations.

In an alternative embodiment the antibodies of the present invention are useful for the close juxtaposition of two antigens. This is particularly useful for increasing the localized concentration of antigens, e.g., enzyme-substrate pairs.

4.6 Western Blots

The compositions of the present invention will find great use in immunoblot or western blot analysis. The anti-Borrelia VMP-like antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Immunologically-based detection methods for use in conjunction with Western blotting include enzymatically-, radiolabel-, or fluorescently-tagged secondary antibodies against the toxin moiety are considered to be of particular use in this regard.

4.7 Vaccines

The present invention contemplates vaccines for use in both active and passive immunization embodiments. Immunogenic compositions, proposed to be suitable for use as a vaccine, may be prepared most readily directly from immunogenic Borrelia VMP-like peptides prepared in a manner disclosed herein. Preferably the antigenic material is extensively dialyzed to remove undesired small molecular weight molecules and/or lyophilized for more ready formulation into a desired vehicle.

The preparation of vaccines which contain Borrelia VMP-like peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables. Either as liquid solutions or suspensions: solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

Vaccines may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1 to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10 to about 95% of active ingredient, preferably about 25 to about 70%.

The Borrelia VMP-like-derived peptides of the present invention may be formulated into the vaccine as neutral or salt forms. Pharmaceutically-acceptable salts, include the acid addition salts (formed with the free amino groups of the peptide) and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e g., the capacity of the individual's immune system to synthesize antibodies, and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine includes use of agents such as aluminum hydroxide or phosphate (alum), commonly used as about 0.05 to about 0.1% solution in phosphate buffered saline, admixture with synthetic polymers of sugars (Carbopol®) used as an about 0.25% solution, aggregation of the protein in the vaccine by heat treatment with temperatures ranging between about 70° to about 101° C. for a 30-second to 2-minute period, respectively. Aggregation by reactivating with pepsin treated (Fab) antibodies to albumin, mixture with bacterial cells such as *C. parvum* or endotoxins or lipopolysaccharide components of Gram-negative bacteria, emulsion in physiologically acceptable oil vehicles such as mannide mono-oleate (Aracel A) or emulsion with a 20% solution of a perfluorocarbon (Fluosol-DA®) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays.

4.8 DNA Segments

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding a Borrelia VMP-like peptide in its natural environment. Such promoters may include promoters normally associated with other genes, and/or promoters isolated from any viral, prokaryotic (e.g., bacterial), eukaryotic (e.g., fungal, yeast, plant, or animal) cell, and particularly those of mammalian cells. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter/expression systems contemplated for use in high-level expression include, but are not limited to, the Pichia expression vector system (Pharmacia LKB Biotechnology), a baculovirus system for expression in insect cells, or any suitable yeast or bacterial expression system.

In connection with expression embodiments to prepare recombinant proteins and peptides it is contemplated that longer DNA segments will most often be used, with DNA segments encoding the entire peptide sequence being most preferred. However, it will be appreciated that the use of shorter DNA segments to direct the expression of Borrelia VMP-like peptides or epitopic core regions, such as may be used to generate anti-Borrelia VMP-like antibodies, also falls within the scope of the invention. DNA segments that encode Borrelia VMP-like peptide antigens from about 10 to about 100 amino acids in length, or more preferably, from about 20 to about 80 amino acids in length, or even more preferably, from about 30 to about 70 amino acids in length are contemplated to be particularly useful.

In addition to their use in directing the expression of Borrelia VMP-like peptides of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least an about 14-nucleotide long contiguous sequence that has the same sequence as, or is complementary to, an about 14-nucleotide long contiguous DNA segment of SEQ ID NO:1 and SEQ ID NO:3 will find particular utility. Longer contiguous identical or complementary sequences, e g, those of about 20, 30, 40, 50, 100, 200, (including all intermediate lengths) and even those up to and including about 1227-bp (full-length) sequences will also be of use in certain embodiments.

The ability of such nucleic acid probes to specifically hybridize to Borrelia VMP-like-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of about 14, 15–20, 30, 40, 50, or even of about 100 to about 200 nucleotides or so, identical or complementary to the DNA sequence of SEQ ID NO:1 and SEQ ID NO:3, are particularly contemplated as hybridization probes for use in, e.g., Southern and Northern blotting Smaller fragments will generally find use in hybridization embodiments, wherein the length of the contiguous complementary region may be varied, such as between about 10–14 and up to about 100 nucleotides, but larger contiguous complementary stretches may be used, according to the length complementary sequences one wishes to detect.

The use of a hybridization probe of about 14 nucleotides in length allows the formation of a duplex molecule that is both stable and selective. Molecules having contiguous complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of about 15 to about 20 contiguous nucleotides, or even longer where desired.

Of course, fragments may also be obtained by other techniques such as, eg., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as PCR™, by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., conditions of high stringency where one will select relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating Borrelia VMP-like-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy et al., 1994; Segal, 1976; Prokop, 1991; and Kuby, 1994, are particularly relevant.

Of course, for some applications, for example, where one desires to prepare mutants employing a mutant primer strand hybridized to an underlying template or where one seeks to isolate Borrelia VMP-like-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

4.9 Biological Functional Equivalents

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to the following codon table:

TABLE 4

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3), proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

4.10 Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 1 to 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

4.11 Monoclonal Antibodies

Means for preparing and characterizing antibodies are well known in the art (See, e.g., Harlow and Lane, 1988; incorporated herein by reference).

The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*) incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No. 4,196,265, incorporated herein by reference. Typically, this technique involves immunizing a suitable animal with a selected immunogen composition, eg., a purified or partially purified LCRF protein, polypeptide or peptide. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes form the immunized animal are then fused with cells of an immortal myeloma cell, generally one of the-same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserme blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations mAbs produced by either means may be further purified, if desired, using filtration, centrifugation and various chromatographic methods such as HPLC or affinity chromatography.

4.12 Pharmaceutical Compositions

The pharmaceutical compositions disclosed herein may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The composition can be formulated in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

5.0 EXAMPLES

The following examples report the evaluation of Bb clones obtained from biopsies and blood samples from mice infected with infectious *B. burgdorferi,* an in vivo selection approach for detection of antigenic variation at the vls site and identification and characterization of the vls locus.

5.1 Example 1

Experimental Procedures 5.1.1 Bacterial Strains

*B. burgdorferi* strains B31 (ATCC 35210), Sh-2-82, and N40 were originally isolated from Ixodes scapularis ticks in the state of New York (Burgdorfer et al., 1982; Schwan et al., 1988b; Barthold et al., 1990). These strains have been shown to be infectious in laboratory animals (Barthold et al., 1990; Norris et al., 1995). The high-passage B31 strain (ATCC 35210) had undergone in vitro passages for several years and had lost infectivity (Moody et al., 1990). Nine B31 and 10 Sh-2-82 passage 5 clones had been characterized according to infectivity and described previously by Norris et al. (1995). An additional nine high- and low-infectivity B31 clones were obtained from P. A. Rosa and T. G. Schwan of the Rocky Mountain Laboratories, Hamilton, Mont. Infectious *B. afzelii* ACA-1 and *B. garinii* IP-90 clones were obtained by subsurface plating of organisms following isolation from experimentally infected C3H/HeN mice (A.G.B.). Spirochetes were cultured in BSK II medium as described (Norris et al., 1995). The *E. coli* strains XL1-blue MRF' (Stratagene, La Jolla, Calif.) and BL-21 (DE3) (Novagen, Madison, Wis.) were used for DNA cloning and fusion protein expression, respectively.

5.1.2 Subtractive Hybridization

Subtractive hybridization was performed according to the procedure of Seal et al. (1992). *B. burgdorferi* total DNA was isolated from late log-phase cultures (~$10^{10}$ cells) as described previously (Walker et al., 1995). Total DNA of the high-passage *B. burgdorferi* B31 was subjected to ultrasonic disruption, and the resulting 0.5- to 1-kb fragments were utilized as driver DNA. The driver DNA (50 $\mu$g) was then mixed with 1 $\mu$g of total DNA from the low-passage B31 digested to completion with Sau 3 AI (target DNA). The target-drive DNA mixture was denatured and reannealled under the conditions described (Seal et al., 1992) The resultant DNA mixture was ligated into BamHI-digested pBluescript II SK (−) vector (Stratagene). The ligation mixture was used to transform *E. coli* XL-1 blud MRF' competent cells (Stratagene) and the transformants were plated on Luria-Bertani (LB) agar containing 100 μg/ml ampicillin, 0.5 mM isopropyl thiogalactopyranoside, and 20 μg/ml 5-bromo-4-chloro-3-indolyl-D-galactoside. LB broth cultures inoculated with white colonies were blotted to Hybond-N+ nylon membranes (Amersham, Arlington Heights, Ill.) with a Bio-Dot apparatus (Bio-Rad, Hercules, Calif.) and screened by hybridization with [$^{32}$P]-labeled driver and target DNA. The clones that hybridized only to target probe but not to driver probe were partially sequenced using vector sequence-based T3 and T7 primers.

5.1.3 DNA Electrophoresis and Southern Hybridization

Total *B. burgdorferi* DNA was prepared in agarose inserts and separated in 1% Fastlane agarose gels (FMC, Rockland, Me.) by pulsed-field electrophoresis as described previously (Norris et al., 1995). Restriction enzyme-digested DNA fragments were separated by standard agarose gel electrophoresis (Sambrook et al., 1989). DNA bands were visualized by ethidium bromide staining. For Southern hybridization, DNA was blotted to Hybone-N+ nylon membranes by the alkaline transfer method (Sambrook et al., 1989). The blots were hybridized with [$^{32}$P]-labeled probes at 65° C. in the presence of 1M NaCl overnight as described previously (Walker et al., 1995). The blots were washed sequentially as follows: once in 2×SSC at 65° C. for 15 min, twice in 1×SSC at 65° C. for 15 min, and twice in 0.1×SSC at room temperature for 10 min. Autoradiography was performed using X-OMAT film (Kodak, Rochester, N.Y.) with enhancing screens.

5.1.4 DNA Cloning and Sequence Analysis

The total plasmid DNA of B31-5A3 was prepared and treated with mung bean nuclease to open the covalently linked telomeres of the linear plasmids as described by Hinnebusch et al. (1990). The resulting plasmid DNA was filled in with the Klenow fragment of DNA polymerase, and an EcoRI linker (5'-CCGGAATTCCGG-3'; SEQ ID NO: 9) was ligated onto the plasmid ends using T4 ligase. The preparation was then digested with EcoRI and ligated into EcoRI-treated λDASH II vector (Stratagene). The recombinant phages were propagated and screened by plaque hybridization with the pJRZ53 probe according to the vector manufacturer's instructions. Lambda phage DNA was purified by CsC1 gradient purification method (Sambrook etal., 1989).

For random cloning of the λDASH-Bb12 insert, the purified bacteriophage DNA was treated with DNase I in the presence of Mn++ and cloned into Eco RV-digested pBluescript II SK (−) as described previously (Demolis et al., 1995). The insert DNA of λDASH-Bb12 was excised from agarose gels, purified using a Qiaex II gel extraction kit (Qiagen, Chatsworth, Calif.), radiolabeled, and used as a probe to screen *E. coli* XL1-blue MRF' transformants by Southern hybridization. Positive clones were sequenced as described below using T3 and T7 primers. In some instances, unsequenced regions were filled in by primer walking. The sequenced fragments were assembled using by the GELASSEMBLE program of GCG (Program Manual for the Wisconsin Package, Version 8, Genetics Computer Group, Madison Wis.). High stringency settings were applied to discriminate identical sequences from highly homologous sequences.

All plasmid and PCR™ templates were purified by Wizard columns (Promega, Madison, Wis.) and desalted through desalting columns (Amicon, Beverly, Mass.). DNA sequences were determined with an ABI377 automatic DNA sequence (Perkin-Elmer/ABI, Foster City, Calif.) in the DNA Core Laboratory of Department of Microbiology and Molecular Genetics at University of Texas Medical School at Houston. The GAP and PILEUP programs of GCG were used to determine sequence homology (percent similarity and identity) and to perform multiple sequence alignments, respectively. Graphical output of alignments was prepared in part through the use of the BOXSHADE program (originally programmed by K. Hofmann at Bioinformatics Group, Isrec, Switzerland and M. D. Baron at the Institute of Animal Health, Pirbright, U.K. and compiled in Pascal version for Sun Solaris/Pascal by P. A. Stockwell at University of Otago, Dunedin, New Zealand). Searches for sequence similarity were performed at the National Center for Biotechnology Information using the BLAST programs (Altschul et al., 1990).

5.1.5 PCR™ Techniques

All PCR™ amplifications were performed using the thermalase PCR™ kit (Amresco, Solon, Ohio) in a Minicycler from MJ Research (Watertown, Mass.). For primer pairs containing 5'-end nested sequences F4120 (SEQ ID NO:4) and R4121(SEQ ID NO:5), a two-step program was used as follows: 96° C. for 3 min, 5 cycles of denaturation at 95° C. for 40 sec, annealing at 56° C. for 40 sec, and extension at 72° C. for 2 min, followed by 30 cycles at a higher annealing temperature at 65° C. For primer pairs without nested sequences F4064 (SEQ ID NO:6) and R4066 (SEQ ID NO:7), 35 amplification cycles of denaturation at 95° C. for 40 sec, annealing at 60° C. for 40 sec, and extension at 72° C. for 2 min were used. The final cycles of both programs were followed by extension at 72° C. for 10 min.

For RT-PCR™, total RNA was extracted from late log-phase cultures of *B. burgdorferi* B31-5A3 with a RNA purification kit (Amresco). The resulting RNA preparation was used to produce cDNA with the R4066 primer (5'-CTTTGCGAACGCAGACTCAGCA-3'; SEQ ID NO: 10) (FIG. 2C), primer R4066, and 1 μl of the RT reaction were used for PCR™ reaction as described above to produce an 198-bp fragment. The PCR™ product was then cloned into the pCR-II vector (Invitrogen, San Diego, Calif.) according to the supplier's manual, and the resulting clones were sequenced.

5.1.6 GST Fusion Protein Expression

A 614-bp fragment containing the vls1 cassette was amplified by PCR™ using (+) strand primer F4120 (5'-GCGGATCCAGTACGACGGGGAAACCAG-3'; SEQ ID NO: 11) and (−) strand primer R4121 (5'-GCGGATCCCCTTCTCTTTCTCACCATCC-3'; SEQ ID NO: 12) (FIG. 2C). For cloning purposes, the inventors' added a 8-bp sequence (underlined) at the 5'-ends of both primers to create BamHI sites. The resultant PCR™ products containing the entire vls1 cassette region was cloned into the BamHI site of the pGEX-2T expression vector (Pharmacia, Piscataway, N.J.) to produce a GST fusion protein (Designated GST-Vls1) in *E. coli* strain BL-21(DE3) according to the supplier's instructions. The insert sequence of the recombinant plasmid was verified prior to use for protein expression. The fusion protein was purified by glutathione-Sepharose 4B column (Pharmacia) according to the manufacturer's instructions.

5.1.7 Antibodies and Immunoblotting (Western Blotting)

Antisera against the GST-Vls1 fusion protein and GST as a control were prepared in rabbits by immunization of rabbits with 20 μg protein in complete Freunds adjuvant and boosting with the same amount of protein in incomplete Freunds adjuvant at 3-week intervals (Sambrook et al., 1989). Nonspecific reactivity of the antiserum was removed by absorption with cell lysate of a low-infectivity B31 clone 5A2 lacking pBB28La plasmid (FIG. 1B) as described previously (Carroll and Gherardini, 1996). Antiserum against recombinant OspD was prepared in a similar manner, and monoclonal antibody H9724 reactive with *B. burgdorferi* flagellum protein (Fla) was obtained as a hybridoma culture supernatant by D. D. Thomas (University of Texas Health Science Center at San Antonio).

Late log-phase *B. burgdorferi* cultures were harvested by centrifugation and washed in phosphate-buffered-saline (PBS, 135 mM NaCl, 9 mM $Na_2HPO_4$, 6 mM $KH_2PO_4$, pH 7.2). The organisms were resuspended at a concentration of $10^{10}$ cells/ml in PBS. Proteins of approximately $10^7$ organisms were subjected to sodium dodecyl sulfate-polyacrylamide gel electrophoresis (SDS-PAGE), electro-transferred to PVDF membranes (Millipore, Bedford, Mass.), and detected with antibody using a ECL western blot kit from Amersham according to the supplier's instructions.

5.1.8 Surface Proteolysis

Proteinase K digestion of *B. burgdorferi* B31-5A3 was performed as described previously (Norris et al., 1992). Proteins of the treated organisms were separated by SDS-PAGE, electro-transferred to PVDF nitrocellulose, and reacted with antisera against GST-Vls1 or OspD or with monoclonal antibody H9724. Reactions were visualized using the ECL western blot kit.

5.1.9 Mouse Infections

The original stock of B31-5A3 (Norris et al., 1995) was cultured in BSK II broth for 7 days, and the culture was diluted to a concentration of $10^6$ cells/ml in BSK II broth. One hundred microliters of the diluted culture ($10^5$ organisms) were used to inoculate each of eight 3-week-old female C3H/HeN mice by intradermal injection at the base of the tail. Each mouse was implanted with an identification microchip for follow-up samplings during the course of infection. Four weeks after infection, the organisms were isolated by inoculating 50 μl of blood or a full-thickness biopsy (~2 mm in diameter) of the ear into 6 ml of BSK II broth. All 5 ear cultures and 6 of 8 blood cultures were positive. Clonal populations of *B. burgdorferi* isolates from C3H/HeN mice were obtained by subsurface plating (Norris et al., 1995). The first passages of these cultures were frozen in BSK II medium with 20% glycerol at −70° C. as stocks for further study. The vls cassette region at the expression site was amplified by PCR™ using primers F4120 and R4066 (FIG. 2C) and sequenced using the same set of primers. Samples of the frozen stocks (~3 μl) were scraped from the surface, thawed, and added directly into PCR™ tubes as the DNA template source to minimize possible variation during in vitro cultivation. Serum sample were also collected from each mouse before infection and 4 weeks after initial infection and stored at −70° C. for immunoblot analysis.

5.2 Example 2

Antigenic Variation at vls Site

Bb clones isolated from ear biopsies and blood samples obtained 4 weeks post inoculation of C3H/HEN mice with the infectious B31 clone 5A3 were evaluated. A flow diagram is provided in FIG. 8. Ear punch biopsies ~2 mm in diameter were obtained from 5 of 8 mice. The cultures were named according to their source (ie. m1e4 refers to mouse 1, ear culture, 4 weeks). Clonal populations were obtained by plating on passage of culture BSKY agar plates, and 12 colonies of each isolate were selected, cultured briefly in 2 ml BSKY medium, and frozen. Individual clones were designated m1e4A, m1e4B, etc. Samples of these clones were subjected to amplification of the vls cassette present in the vlsE expression site by using primers in the "constant" regions on either side of the cassette. The resulting PCR™ products were sequenced directly.

Surprisingly, antigenic variation did not occur by substitution of the entire vls cassette at the expression site (e.g. vls1) with a single, intact "silent" vls cassette (e.g. vls2 through vls16) (see FIG. 9). Examination of 5 clones from the ear of mouse 1 (FIG. 10) indicated that the vlsE sequences of each clone differed from 1) the original sequence (vls1), 2) one another; and, 3) each of the silent vls cassettes. These results were verified by examination of one clone from each ear or blood isolate from the eight mice (FIG. 11). Each one of the mouse isolate sequences appeared to be comprised of a mosaic of segments from several different silent vls cassettes (between 7 and 11 in preliminary analyses). Sequence variability was restricted to the vls cassette region delimited by the ' sequences, and in all cases the open reading frame was preserved. The vlsE cassette regions of controls consisting of five clonal populations from the inoculating culture were identical to the original vls1 sequence, as were the sequences obtained from cultures passed 2 to 4 times in vitro (one week per passage). Therefore the rearrangement process appears to be activated in vivo, and does not occur at a rapid rate in vitro.

5.3 Example 3

Identification of the 28-kb Linear Plasmid, pBB28La

*B. burgdorferi* strains generally exhibit loss of infectivity following 10 to 17 in vitro passages (Johnson et al., 1984; Schwan et al., 1988a; Norris et al., 1995), coinciding with the loss of plasmids (Barbour, 1988; Xu et al., 1996). It was hypothesized that the decreased infectivity occurring during in vitro passage of Lyme disease Borreliae is due to loss of genetic content, specifically plasmids encoding virulence factors. Therefore, the inventors' expected to identify some of these virulence factors by directly comparing the plasmid content of the organisms differing in infectivity.

One of the complications involved in studying *B. burgdorferi* plasmids is that many plasmids are in the 20 kb to 40 kb size range (Xu and Johnson, 1995), making it difficult to resolve plasmids with similar sizes by standard electrophoretic techniques. In addition, mutagenic techniques and other genetic manipulation tools are in an early stage of development in *B. burgdorferi* (Samuels et al., 1994; Rosa et al., 1996), thereby limiting the ability to examine the importance of these plasmids in pathogenesis by direct genetic approaches.

To overcome these limitations, the inventors' utilized a simple subtractive hybridization technique to enrich and eventually identify sequences present only in high-infectivity organisms.

Total DNA from a high-infectivity (low-passage) B31 strain was digested to completion with Sau 3AI (target DNA). The target DNA was mixed with a 50-fold excess of total DNA from a low-infectivity (high passage) B31 derivative that had been sheared by ultrasonication (driver DNA). The DNA mixture was denatured and allowed to reanneal. DNA fragments in the resultant DNA preparation in which the Sau 3 AI sites were regenerated were ligated into the BamHI site of pBluescript SK (−). A total of 63 clones were isolated and screened by Southern hybridization using the target DNA and driver DNA as probes, respectively. Eight of these clones hybridized with target DNA but not to driver DNA.

The inserts of the eight clones were partially sequenced using the vector-based primers, and the sequences were subjected to database searches for sequence similarity. One of the clones, designated pJRZ53, contained a 562-base pair (bp) Sau 3 AI fragment with a single, contiguous open reading frame. The predicted amino acid sequence of this open reading frame was compared to Vmps of *B. hermsii*, and showed 27.2% identity and 56.8% similarity to Vmp17. Based on this sequence similarity, the pJRZ53 insert was called a vmp-like sequence (vls). The pJRZ53 insert exhibited a lower degree of amino acid sequence similarity with *B. burgdorferi* B31 outer surface protein C (OspC) (26.6% identity and 44.5% similarity).

To identify the genomic location of the vls sequence, the pJRZ53 insert was hybridized with Southern blots of total B31 DNA separated by pulsed-field electrophoresis. A DNA band migrating at 28 kb hybridized to the probe (see FIG. 1B) and was determined to be a linear plasmid by two-dimensional agarose gel electrophoresis and restriction mapping. This vls-containing plasmid of *B. burgdorferi* B31 was designated pBB28La.

5.4 Example 4

Correlation Between pBB28La and Infectivity

This example illustrates the determination whether or not the vls-encoded function was required for infection. Previous studies (Norris et al., 1995), had indicated that clones of low-passage *B. burgdorferi* strains B31 and Sh-2-82 exhibited two distinct infective phenotypes when tested in C3H/HeN mice. A representative high-infective clone had a median infectious dose ($ID_{50}$) of $1.8 \times 10^2$ organisms, whereas the low-infective clone tested showed a much higher $ID_{50}$ ($\geq 1 \times 10^5$ organisms).

It was reasoned that if the vls-encoded function is important for virulence, all clones with the high-infective phenotype should contain the vls-containing plasmid, and loss of this plasmid would result in low-infective phenotype. To test this hypothesis, the pJRZ53 probe was hybridized with total DNA from both high- and low-infective *B. burgdorferi* clones. All nine B31 clones tested had a plasmid banding pattern almost identical to each other when visualized by ethidium bromide staining (FIG. 1A).

However, hybridization of pJRZ53 with the blot made from the same gel revealed that all five high-infective B31 clones possessed the vls-containing pBB28La plasmid, whereas only 1 or 4 low-infective clones (B31-5A10) had this plasmid (FIG. 1B). It appears that the low-infective B31-5A10 clone is lacking another plasmid that correlates with infection. Nine additional low-passage B31 clones obtained from P. A. Rosa and T. G. Schwan (Rocky Mountain Laboratories, Hamilton, Mont.) exhibited a similar pattern; all six of the high-infective clones contained pBB28La, whereas only 1 of 3 low-infective clones contained the plasmid, based on hybridization with the pJRZ53 probe. These results indicated a strong correlation of pBB28La with the high-infective phenotype in clonal populations of *B. burgdorferi* B31 .

To verify the correlation found in strain B31, ten previously characterized clones of strain Sh-2-82 (Norris et al., 1995) were examined. A pBB28La homolog was detected in seven high-infective clones but not in three low-infective clones of strain Sh-2-82. Similar studies revealed the presence of a single vls-containing plasmid in infectious *B. afzelii* ACA-1 and *B. garinii* IP-90 strains. In contrast to the multiple vmp-containing linear plasmids in *B. hermsii*, only one vls-containing plasmid was found in each of the Lyme disease isolates tested under the hybridization conditions employed. These vls-containing plasmids migrated consistently at ~28 kb in agarose gels in the strains examined.

Out of a total of 32 clones or strains examined, all 22 clones or strains with the high-infective phenotype contained pBB28La, and only 2 of 10 low-infective clones possessed this plasmid (Table 2). The Southern hybridization studies indicated that the vls-containing plasmid is associated with infectivity and therefore may encode essential virulence factor(s).

5.5 Example 5

Cloning and Sequencing of the vls Locus

A particular clonal population of *B. burgdorferi* B31 (clone B31-5A3) was utilized in order to minimize clonal variation. B31-5A3 has a high-infective phenotype (Norris et al., 1995) and possesses the pBB28La plasmid (FIG. 1B, lane 3). pJRZ53 was shown to hybridize with a single 14-kb fragment generated by digestion of B31-5A3 plasmid DNA with EcoRI However, treatment of the B31-5A3 plasmid DNA with PstI, Sau 3 AI, or RsaI each yielded multiple fragments ranging in size from ~400 bp to 4,000 bp that hybridized with the probe, denoting the presence of multiple copies of the vls sequence.

The 14-kb EcoRI fragment was cloned into λDASHII to permit a detailed analysis of this region. The 14-kb fragment was predicted to have a covalently-closed telomere at one end. Therefore, a technique developed by Hinnebusch et al. (1992) was utilized to open the telomeric loop with mung bean nuclease and attach an EcoRI linker, thereby permitting ligation into the cloning vector. A lambda clone, designated λDASH-Bb12, was isolated that contained the 14-kb *B. burgdorferi* DNA fragment, as confirmed by restriction and hybridization. An internal EcoRI site was found to divide the λDASH-Bb12 insert into two smaller 4- and 10-kb fragments; an independently-derived clone containing the 10-kb fragment was also isolated during screening of the library. To verify that the 4-kb and 10-kb EcoRI fragments were physically linked in the native *B. burgdorferi* plasmid, the region containing the internal EcoRI site was amplified using *B. burgdorferi* B31-5A3 DNA as the template. The resulting PCR™ product had a sequence identical to that of the corresponding region of λDASH-Bb12, indicating that the 4- and 10-kb EcoRI fragments are contiguous in pBB28La. Restriction digestion of *B. burgdorferi* plasmid DNA at this EcoRI site was not efficient, whereas complete cleavage was obtained consistently at the same site in the λDASH construct. Similar incomplete digestion has been observed with certain restriction sites in *B. burgdorferi* chromosomal DNA (Casjens et al., 1995) and may be related to DNA modification (Hughes and Johnson, 1990).

A random cloning, "shotgun" strategy was utilized to sequence nearly 10 kb of the λDASH-Bb12 insert. A total of 80 random clones were sequenced using vector-based primers. Additional sequencing reactions were carried out to fill the gaps between the sequenced regions by primer-walking. The resulting assembled sequences had an average of 5-fold coverage. A short segment (~200 bp) 1227 bp from the right telomeric end has been refractory to sequencing by a number of techniques. In contrast to the overall low guanosine-cytosine (G+C) content of the *B. burgdorferi* genome (~28%), the vls locus has a G+C content of 50%.

5.6 Example 6

Organization of the vls Locus

The sequence data revealed an extensive vls locus within the 10-kb EcoRI fragment consisting of an expression site (designated vlsE) and 15 vls cassettes that are highly homologous to the central portion of vlsE (SEQ ID NO:1 and SEQ ID NO:3). The presence of the EcoRI linker sequence between the insert DNA and the vector sequence defined the location of the right telomeric end. VlsE is located 82 bp from the right telomere of pBB28La. It possesses two unique sequences at each of the 5' and 3' regions and a 570-bp vls cassette in the middle which was designated as the vls1 cassette (FIG. 2B). The vls1 cassette is flanked at either end by the 17-bp direct repeat sequence 5'-GAGGGGGCTATTAAGGA-3' (SEQ ID NO:8) encoding the amino acids EGAIK. An array of 15 vls cassettes begins approximately 500 bp upstream of vlsE on the same plasmid (FIG. 2A). The vls1 cassette and the other vls cassettes (vls2 through vls16) share 90.0% to 96.1% nucleotide sequence identity and 76.9% to 91.4% predicted amino acid sequence identity. The 17-bp direct repeat is conserved in nearly all of the upstream vls cassette sequences.

The vlsE gene of *B. burgdorferi* B31-5A3 is predicted to encode a 356 amino acid protein with a molecular mass of 35,986 daltons (FIG. 2C). A consensus ribosome binding site and consensus −35 and −10 sigma −70-like promoter sequences are located upstream of the predicted translational start site. VlsE contains a putative lipoprotein leader sequence with an apparent signal peptidase II cleavage site (FINC) (Wu and Tokunaga, 1986) which resembles those of other Borrelial lipoproteins, including OspC (Fuchs et al., 1992). Cleavage of the 18 amino acid signal peptide would result in a mature polypeptide with a calculated molecular mass of 33,956 daltons and an isoelectric point (pI) of 7.3. Except for the putative leader peptide, VlsE is predominantly hydrophilic.

VlsE shows 37.4% identity and 57.8% similarity homology at the amino acid level and 58.8% identity at the nucleotide level to vmp17 of *B. hermsii* (FIG. 3A). VlsE shares a lower level of homology to *B. burgdorferi* ospC at both the nucleotide (41.6% identity) and amino acid (26.3% identity and 47.5% similarity) levels. The particular vlsE allele contained in *B. burgdorferi* B31 clone 5A3 has been designated vlsE1, to distinguish it from variant vlsE alleles.

An additional 15 vls cassettes (474 to 594 bp in length) were identified ~500 bp upstream of vlsE (FIG. 2A and FIG. 3B, SEQ ID NO:1 and SEQ ID NO:3). These cassettes are oriented in the opposite direction to vlsE and are arranged in a head-to-tail fashion in a nearly contiguous open reading frame interrupted only by a stop codon in cassette vls1 and two frame shifts in cassettes vls14 and vls16. None of these vls cassettes have recognizable ribosome binding sites or promoter sequences; therefore they are thought to be non-expressed or 'silent'. The ends of the vls cassettes were defined by alignment with the vls1 cassette (FIG. 3B). In general, the vls cassettes have the same 17-bp direct repeat at either end; one exception is the joint region between vls9 and vls10, where only 10 identical nucleotides were identified. The first vls cassette (vls2) lacks the first 126 bp of the vls cassette sequence, but contains a 55-bp sequence which is identical to the 5' region of vlsE, coding for the last 11 amino acids of the leader peptide and the first 7 amino acids of the putative mature VlsE. The vls7 cassette contains a 105-bp deletion relative to vls1 in the 5' region. The vls8 and vls10 cassettes are lacking the first 54 nucleotides of the cassette. The last cassette in this array, vls16, is truncated at the 3' end and is followed by an apparent noncoding region. The 562-bp insert of pJRZ53 was localized to the joining region between vls8 and vls9 by sequence comparison.

The vls cassettes contain six highly conserved regions which are interspersed by six variable regions (VR) at both the nucleotide and amino acid levels. FIG. 3B shows an alignment of the predicted amino acid sequences for all 16 vls cassettes identified. Except for occasional codon changes and the deletions mentioned previously, the conserved regions are almost identical in all cassettes. On the other hand, the vls cassettes are distinguished from each other by considerable sequence variations limited predominantly to the six variable regions (VR-I through VR-VI). The variable regions range from 21 bp (VR-VI) to 63 bp (VR-IV) in length. With exception of an insertion of a TAG stop codon in vls11 and TG insertions in vls14 and vls16 resulting in frameshifts, all deletions and insertions are nucleotide triplets, indicating preservation of the open frame. The sequence variations at most polymorphic positions result in conservative amino acid changes, suggesting that certain amino acids are required at these positions for function. Even within the six variable regions, there is a clear sequence conservation. For example, the variable sequences in VR-I are interspersed by stretches of identical sequences ranging from 6 to 9 bp, as reflected in the predicted amino acid sequences (FIG. 3B).

5.7 Example 7

Expression of vlsE

To determine whether vlsE is transcribed, reverse transcriptase-polymerase chain reaction (RT-PCR™) was utilized to amplify a 3' region of vlsE (191 bp) from total RNA of in vitro cultured B31-5A3. After the reverse transcriptase reaction, PCR™ amplification, and agarose electrophoresis, a band of the expected size was observed by ethidium bromide staining. The RT-PCR™ product was cloned into the pCRII vector and the recombinant plasmids were sequenced. Three independently derived recombinant plasmids contained DNA sequences identical to the corresponding region of vlsE, demonstrating that vlsE is transcribed in vitro. No RT-PCR™ products were observed in the agarose gel if reverse transcriptase was omitted from the reaction, confirming that the RT-PCR™ products were derived from the mRNA of B31-5A3.

To identify the protein product of vlsE, an internal 614-bp fragment containing vls1 was amplified by polymerase chain reaction (PCR™) and cloned into the pGEX-2T expression vector to produce a glutathione-S-transferase (GST)-Vls1 fusion protein in *E. coli*. Rabbit antiserum against the GST-Vls1 fusion protein was used to probe protein blots of *B. burgdorferi* B31-5A2 and B31-5A3 clones. The low-infectivity clone B31-5A2 was used as a negative control for immunoblot analysis, because it lacks pBB28La (FIG. 1B, lane 2). The antiserum detected a protein with an $M_r$ of approximately 45,000 daltons in the high-infectivity clone B31-5A3 but not in the low-infectivity clone B31-5A2 (FIG. 6, lanes 10 and 11). Neither the preimmune serum nor antiserum against GST alone reacted with this protein. The size of the protein identified by immunoblot analysis is larger than the predicted molecular mass of 33,956 daltons.

Attachment of a lipid moiety to the N-terminus of VlsE by signal peptidase II may contribute to the altered electrophoretic mobility.

5.8 Example 8

Surface Localization of VlsE

The presence of a putative lipoprotein leader peptide and the overall hydrophilic nature of VlsE raised the possibility that it is attached to the bacterial membrane via a lipid anchor. To test this possibility, B. burgdorferi B31-5A3 was incubated in the presence of [$^3$H]-palmitate as described previously (Norris et al., 1992). VlsE was radiolabelled by [$^3$H]-palamitate along with other B. burgdorferi lipoproteins, suggesting that VlsE is a lipoprotein.

Exposure of viable B. burgdorferi 5A3 to proteinase K produced results consistent with the surface localization of VlsE. VlsE was degraded by proteinase K in as little as 10 min (FIG. 4A), even though the organisms appeared intact by dark-field microscopy. Consistent with previous study (Norris et al., 1992), B. burgdorferi OspD protein was also removed by proteinase K treatment (FIG. 4B). In contrast, the Fla subunit of the periplasmic flagella was not affected by proteinase K (FIG. 4C), providing further evidence that the outer membranes of the organisms remained intact during the proteinase K treatment.

5.9 Example 9

Genetic Variation at the vlsE Site

The similarity of the vls locus to the vmp system of B. hermsii prompted the question whether genetic recombination between the expressed and silent vls cassettes could be demonstrated in the mammalian host. The overall experimental design is illustrated in FIG. 5A. B. burgdorferi B31-5A3, inoculated directly from a frozen stock, was cultured for seven days and used to intradermally inject a group of eight female C3H/HeN mice ($10^5$ organisms per mouse). B. burgdorferi was re-isolated four weeks after the initial infection. To retain the infected mice for multiple samplings at different periods of infection, only ear punch biopsy and blood specimens were taken to culture the organisms. A total of five ear and six blood isolates were examined. To examine possible genetic heterogeneity within the mouse isolates, 16 B. burgdorferi clones of each isolate were obtained by colony formation on agarose plates and preserved by freezing. One clone from each of the isolates was used as a source of template DNA to amplify the expressed vls cassette sequence using primers F4120 and R4066 specific for the 5' and 3' unique regions of vlsE, respectively (FIG. 2C). The first passage frozen stock was used to provide DNA template for PCR™ amplification to avoid possible variation during in vitro culture. The PCR™ products were sequenced directly using the same set of primers. The B. burgdorferi clones and associated sequences derived from the 4-week isolates were designated by a combination of mouse number (m1 to m8), tissue source (e for ear and b for blood), week post infection (4), and a clone designation (A to P) for the 16 clones from each isolate.

When compared with the parental vlsE of the clone B31-5A3 (allele vlsE1) inoculation, multiple base substitutions, deletions and insertions were found within the vls cassette region of vlsE, making each allele unique. These changes resulted in numerous differences in the predicted amino acid sequences (FIG. 5B). As found in the silent vls cassettes (FIG. 3B), these mutations were primarily confined within the six variable regions. The variable sequences at almost all positions in the 11 vlsE alleles could be found in the corresponding regions of the silent vls cassettes. For example, the mle4A and m5e4A alleles have VR-I and VR-II identical to vls4, whereas the VR-I and VR-III regions of m6b4A are identical to the same regions of vls10 (FIG. 5B). These results indicated that changes in the original vls1 cassette have originated from the silent vls cassettes via genetic recombination. In contrast, the sequences on either side of the vls cassette remained unchanged in the 11 alleles examined (FIG. 5B).

Based on the gene conversion mechanism in vmp systems, it was initially hypothesized that if genetic recombination occurred at the vlsE site, the expressed vls cassette (vls1 in this case) would be replaced completely by a single silent cassette flanked by the 17-bp direct repeat. However, careful examination revealed that none of the 11 vlsE alleles examined were identical to any of the silent vls cassettes identified to date. Rather, each allele appeared to be a mosaic of segments from several different silent vls cassettes. For instance, although mle4A shares common sequence with vls4 throughout VR-I and VR-II, its VR-III and VR-VI are the same as vls 10 and vls2, respectively. Interestingly, the VR-IV and VR-V regions of mle4A appear to be hybrids of portions of vls10 and vls5 and vls3 and vls5, respectively. Similar patterns can also be found in the rest of these vlsE alleles. These observations suggested that segments, but not entire regions, of the silent vls cassettes were recombined into the expression site. Comparison to the silent cassette sequences at the nucleotide level suggested that 6 to 11 separate recombination events occurred in each of the clones isolated from mice 4 weeks post inoculation. This type of combinatorial reactions could potentially result in millions of different vlsE alleles.

To determine whether the clonal populations from a single mouse also exhibited similar sequence variations, four additional clones of the blood and ear isolates from mouse 1 were chosen to determine the DNA sequence at the vlsE site. The five clones (m1b4A-E) of the blood isolate had sequences identical to each other, although they showed considerable sequence differences from the parental vlsE as represented by m1b4A (FIG. 5B). In contrast, the sequences from the five clones-of the ear isolate differed substantially both from the parental vls1 cassette and from each other (FIG. 5C). Consistent with the 11 vlsE alleles from different isolates, the sequence variations from the same ear isolate were also concentrated in six variable regions (FIG. 5C). Each of these clones again contained a unique combination of sequences identical to portions of several silent vls cassettes. For example, mle4C contained VR-I of vls12, VR-II of vls4, VR-III of vls8, and VR-IV and VR-VI of vls11. The homogeneous nature of B. burgdorferi clones derived from the blood isolate of mouse 1 may be due to the presence of relatively few organisms in the blood as compared to ear biopsies, resulting essentially in cloning by limiting dilution. Alternatively, selection imposed by the host immune response in different tissue environments may affect diversity of vlsE variants.

The sequence variations in the clonal populations of the mouse isolates may also arise from background heterogeneity of the stock culture of the clone B31-5A3 occurring during in vitro culture, because the original clone was cultured 7 days prior to the inoculation of C3H/HeN mice. To test this possibility, the stock culture of B31-5A3 was inoculated into BSK II medium and cultured sequentially in two in vitro passages of 7 days (14 days total). PCR™ products amplified from the vlsE cassette region were obtained using a sample of this culture as template and either sequenced directly or cloned into the PCR™ II vector and sequenced. Two sets of PCR™ products and four independently derived recombinant plasmids containing the PCR™ products all had sequences identical to the initial vlsE sequence. These results indicated that the sequence variations did not occur at high frequency at the vlsE site prior to the inoculation of mice.

5.10 Example 10

Changes in Antigenicity of the VlsE Variants

The promiscuous genetic recombination at the vlsE site and the putative surface location of VlsE suggested that sequence variations in the vlsE alleles result in changes in antigenicity. Nine clonal populations carrying unique vlsE alleles (see FIG. 5B) were subjected to immnunoblot analysis. Although a similar amount of total proteins were loaded into the gel as indicated by reactivity to antibody against *B. burgdorferi* flagellin protein (FIG. 6A), these VlsE variants exhibited a dramatic decrease in reactivity to the antiserum against the GST-Vls1 fusion protein (FIG. 6B). The mouse isolates containing m1b4A and m3b4A alleles had bands which were weakly reactive with the antiserum (FIG. 6, lanes 2 and 5). The other clones examined exhibited faint bands that were visible only with a longer chemiluminescent exposures of the membrane. These reactive bands migrated at lower $M_r$s than VlsE expressed by the parental clone B31-5A3, indicative of changes in either size or conformation. No reactive bands were observed in clone B31-5A2, which lacks the pBB28La plasmid. The decreased reactivity of mouse isolates with antiserum against the parental Vls1 cassette region indicated that the sequence differences in these VlsE variants (FIG. 5B) resulted in changes in important cassette region epitopes and hence antigenic variation.

5.11 Example 11

In Vivo Expression of Vls E and Induction of Antibodies in Infected Humans and Animals Sera from the mice in experiments outlined in FIG. 5A were tested for reactivity with VlsE as a means of determining whether this protein is expressed in vivo. Serum obtained from mouse 1 on 28 days post inoculation with B31-5A3 was reacted with immunoblots of 5A3 (expressing VlsE), 5A2 (lacking vlsE), the GST-Vls1 fusion protein, GST as a control, and two clones isolated from mouse 1 on day 28 (M1e4A and M1b4A). The results shown in FIG. 6C indicated that the C3H/HeN mice infected with *B. burgdorferi* mounted a strong antibody response to VlsE. Although the prebleed serum of mouse 1 had no detectable reactivity, the serum sample collected from the same mouse 4 weeks after initial infection with *B. burgdorferi* B31-5A3 reacted strongly with the GST-Vls1 fusion but not with GST alone, indicating expression of VlsE in the mammalian host. The same serum also had a strong reactivity with the VlsE protein of *B. burgdorferi* B31-5A3, whereas no detectable VlsE band was observed with *B. burgdorferi* B31-5A2. In contrast, the VlsE variant M1e4A exhibited decreased reactivity when reacted with the same mouse serum as shown in FIG. 6C.

Since the C3H/HeN mice were infected with a large number ($10^5$) of the organisms (see FIG. 5A), it was possible that the antibody response against VlsE had resulted from the initial inoculum. To test this possibility, sera from white-footed mice (*Peromyscus leucopus*) infected with *B. burgdorferi* B31 via tick bite and from human Lyme disease patients were used to react with the similar immunoblots. The representative results depicted in FIG. 6D showed that tick-infected Peromyscus mice also had strong reactivity to the VlsE protein of *B. burgdorferi* B31-5A3 and GST-Vls1 fusion protein but not with GST alone. These results were further confirmed with sera from Lyme disease patients (FIG. 6E). A representative serum sample from a clinically diagnosed patient with early Lyme disease symptoms contained highly reactive antibody against the VlsE protein of B31-5A3 and GST-Vls1 fusion protein (FIG. 6E). Similar to the serum from the C3H/HeN mouse (FIG. 6C), the sera from the *Peromyscus leucopcus* mouse (FIG. 6D) and the Lyme disease patient (FIG. 6E) had little reactivity to the VlsE variant M1e4A. These results indicate that VlsE is expressed and is highly immunogenic in the mammalian host, but that genetic variation may generate unique VlsE variants which are no longer fully recognized by the immune response against the parental VlsE. They also indicate that antibodies generated against VlsE may be useful in immunodiagnosis of Lyme disease.

These results indicated that VlsE is expressed and is highly immunogenic in the mammalian host, but that genetic variation can generate unique VlsE variants which are no longer fully recognized by the immune response against the parental VlsE. Additional experiments have shown that some sera from Lyme disease patients also have reactivity with the GST-Vls1 fusion protein and VlsE of *B. burgdorferi* B31-5A3, but not with some of the VlsE variants, thus further supporting the expression and antigenic variation of VlsE in vivo.

TABLE 5

Correlation of pBB28La with Infectivity

| | Strains containing pBB28La/total strains tested | |
|---|---|---|
| Strain | High-infectivity phenotype | Low-infectivity phenotype |
| *B. burgdorferi* B31 | 12/12 | 2/7 |
| *B. burgdorferi* Sh2-82 | 7/7 | 0/3 |
| *B. burgdorferi* N40 | 1/1 | ND[a] |
| *B. afzelii* ACA-1 | 1/1 | ND |
| *B. garinii* IP-90 | 1/1 | ND |
| Total | 22/22 | 2/10 |

[a]Not determined 6.0 References

The following literature citations as well as those cited above are incorporated in pertinent part by reference herein for the reasons cited in the above text.

| | |
|---|---|
| 5,436,000 | Flagella-less Borrelia |
| 5,434,077 | *Borrelia burgdorferi* strain 257 |
| 5,403,718 | Methods and antibodies for the immune capture and detection of *Borrelia burgdorferi* |
| 5,385,826 | Diagnostic assay for Lyme disease |
| 5,324,630 | Methods and compositions for diagnosing Lyme disease |
| 5,283,175 | Genus-specific oligomers of Borrelia and methods of using same |
| 5,279,938 | Sensitive diagnostic test for Lyme disease |
| 5,246,844 | Virulence associated proteins in *Borrelia burgdorferi* |
| 5,217,872 | Method for detection of *Borrelia burgdorferi* antigens |
| 5,187,065 | Method and materials for detecting Lyme disease |

-continued

| 5,178,859 | Vaccine against Lyme disease |
| 5,155,022 | Assay for Lyme disease |

Altschul, Gish, Miller, Myers, Lipman, "Basic local alignment search tool," *J. Mol. Biol.*, 215:403–410, 1990.

Balmelii and Piffatetti, "Analysis of the genetic polymorphism of *Borrelia burgdorferi* sensu lato by multilocus enzyme electrophoresis," *Int. J. Syst. Bacteriol.*, 46:167–172, 1996.

Barbour, "Plasmid analysis of *Borrelia burgdorferi*, the Lyme disease agent," *J. Clin. Microbiol.*, 42:475–478, 1988.

Barbour, "Plasmid analysis of *Borrelia burgdorferi*, the Lyme disease agent," *J. Clin. Microbiol.*, 26:475–478, 1988.

Barbour, "Linear DNA of Borrelia species and antigenic variation," *Trends Microbiol.*, 1:236–239, 1993.

Barbour and Garon, "Linear plasmids of the bacterium *Borrelia burdorferi* have covalently closed ends," *Science*, 237:409–411, 1987.

Barbour, Burman, Carter, Kitten, Bergstrom, "Variable antigen genes of the relapsing fever agent *Borrelia hermsii* are activated by promoter addition," *Mol. Microbiol.*, 5:489–493, 1991a.

Barbour, Carter, Burman, Freitag, Garon, Bergstrom, "Tandem insertion sequence-like elements define the expression site for variable antigen genes of *Borrelia hermsii*," *Infect. Immun.*, 59:390–397, 1991b.

Barbour et al., "Structural analysis of the variable major proteins of *Borrelia hermsii*," *J. Exp. Med.*, 158:2127–2140, 1983.

Barbour et al., "Variable major proteins of *Borrelia hermsii*," *J. Exp. Med.*, 156:1312–1324, 1982.

Barstad et al., "Variable major proteins of *Borrelia hermsii*. Epitope mapping and partial sequence analysis of CNBr peptides," *J. Exp. Med.*, 161:1302–1314, 1985.

Barthold, "Antigenic stability of *Borelia burgdorferi* during chronic infections of immunocompetent mice," *Infect. Immun.*, 61:4955–4961, 1993.

Barthold, Moody, Beck, "Suspectibility of laboratory rats to isolates of *Borrelia burgdorferi* from different geographic areas," *Am. J. Trop. Med. Hyg.*, 42:596–600, 1990.

Borst and Geaves, "Programmed gene rearrangements altering gene expression," *Science*, 235:658–667, 1987.

Borst, Bitter, McCulloch, Leeuwen, Rudenko, "Antigenic variation in malaria," *Cell*, 82:104, 1995.

Burgdorfer, Barbour, Hayes, Benach, Grunwaldt, Davis, "Lyme disease, a tick-borne spirochetosis?," *Science*, 216: 1317–1319, 1982.

Carroll and Gheradini, "Membrane protein variations associated with in vitro passage of *Borrelia burgdorferi*," *Infect. Immun.*, 64:392–398, 1996.

Carter et al., "A family of surface-exposed proteins of 20 kilodaltons in the genus Borrelia." *Infect. Immun.*, 62:2792–2799, 1994.

Casjens, Delange III, Ley, Rosa, Huang, "Linear chromosomes of Lyme disease agent spirochetes: genetic diversity and conservation of gene order," *J. Bacteriol.*, 177:2769–2780, 1995.

Demolis, Mallet, Bussereau, Jacquet, "Improved strategy for large-scale DNA sequencing using DNase I cleavage for generating radom subclones," *Biotechniques*, 18:453–457, 1995.

Donelson, "Mechanisms of antigenic variation in *Borrelia hermsii* and African trypanosomes," *J. Biol. Chem.*, 270:7783–7786, 1995.

Fuchs, Jauris, Lottspeich, Preacmursic, Wilskie, Soutschek, "Molecular analysis and expression of a *Borrelia burgdorferi* gene encoding a 22 kDa protein (pC) in *E. coli*," *Mol. Microbiol*, 6:503–509, 1992.

Haas and Meyer, "The repertoire of silent pilus genes in Neisseria gonorrhoeae: evidence for gene conversion," *Cell*, 44:107–115, 1986.

Hagblom, Segal, Billyard, So, "Intragenic recombination leads to pilus antigenic variation in Neisseria gonorrhoeae," *Nature*, 315:156–158, 1985.

Hinnebusch, Bergstrom, Barbour, "Cloning and sequence analysis of linear plasmid telomeres of the bacterium *Borrelia burgdorferi*," *Mol. Microbiol.*, 4:811–820, 1990.

Hughes and Johnson, "Methylated DNA in Borrelia species," *J. Bacteriol*, 172:6602–6604, 1990.

Johnson et al., "Infection of Syrian hamsters with Lyme disease spirochetes," *J. Clin. Microbiol.*, 20:1099–1101, 1984.

Jonsson, Ilver, Falk, Pepose, Normark, "Sequence changes in the pilus subunit lead to tropism variation of Neisseria gonorrhoeae to human tissue," *Mol. Microbiol.*, 13:403–416, 1994.

Kitten and Barbour, "Juxtaposition of expressed variable antigen genes with a conserved telomere in the bacterium *Borrelia hermsii*," *Proc. Natl. Acad. Sci. USA*, 87:6077–6081, 1990.

Kitten and Barbour, "The relapsing fever agent *Borrelia hermsii* has multiple copies of its chromosome and linear plasmids," *Genetics*, 132:311–324, 1992.

Koomey, Gotschlich, Robbins, Bergstrom, Swanson, "Effects of recA mutations on pilus antigenic variation and phase transitions in Neisseria gonorrhoeae," *Genetics*, 117:391–398, 1987.

Kupsch, Knepper, Kuroki, Heuer, Meyer, "Variable opacity (Opa) outer membrane proteins account for the cell tropisms displayed by Neisseria gonorrhoeae for human leukocytes and epithelial cells," *EMBO. J.*, 12:641–650, 1993.

Lambden, Robertson, Watt, "Biological properties of two distinct pilus types produced by isogenic variants of Neisseria gonorrhoeae P9," *J. Bacteriol.*, 141:393–396, 1980.

Livey, Gibbs, Schuster, Domer, "Evidence for lateral transfer and recombination in OspC variation in Lyme disease Borrelia," *Mol. Microbiol.*, 18:257–269, 1995.

Marconi, Konkel, Garon, "Variability of osp genes and gene products among species of Lyme disease spirochetes," *Infect. Immun.*, 61:2611–2617, 1993.

Marconi, Samuels, Landry, Garon, "Analysis of the distribution and molecular heterogeneity of the ospD gene among the Lyme disease spriochetes: evidence for lateral gene exchange," *J. Bacteriol.*, 176:4572–4582, 1994.

Margolis et al., "Homology between *Borelia burgdorferi* OspC and members of the family of *Borrelia hermsii* variable major proteins," *Gene*, 143:105–110, 1994.

Meier, Simon, Barbour, "Antigenic variation is associated with DNA rearrangements in a relapsing fever Borrelia," *Cell*, 41:403–409, 1985.

Meyer, Mlawer, So, "Pilus expression in Neisseria gonorrhoeae involves chromosomal rearrangement," *Cell*, 30:45–52, 1982.

Moody et al., "Lyme borreliosis in laboratory animals: effect of host species and in vitro passage of *Borrelia burgdorferi*," *Am. J. Trop. Med. Hyg.*, 43:87–92, 1990.

Nassif, Lowry, Stenberg, O'Gaora, Ganji, So, "Antigenic variation of pilin regulates adhesion of Neisseria meningitidis to human epithelial cells," *Mol. Microbiol.*, 8:719–725, 1993.

Norris, Carter, Howell, Barbour, "Low-passage-associated proteins of *Borrelia burgdorferi* B31: characterization and molecular cloning of OspD, a surface-exposed, plasmid-encoded lipoprotein," *Infect. Immun.*, 60:4662–4672, 1992.

Norris et al., "High- and low-infectivity phenotypes of clonal populations of in vitro-cultured *Borrelia burgdorferi*," *Infect. Immun.*, 63:2206–2212, 1995.

Norris et al., "Low-passage-associated proteins of *Borelia burgdorferi* B31: characterization and molecular cloning of OspD, a surface exposed, plasmid-encoded lipoprotein," *Infect. Immun.*, 60:4662–4672, 1992.

Persing, Mathiesen, Podzorski, Barthold, "Genetic stability of *Borrelia burgdorferi* recovered from chronically infected immunocompetent mice," *Infect. Immun.*, 62:3521–3527, 1994.

Plasterk et al., "Transposition of structural genes to an expression sequence on a linear plasmid causes antigenie variation in the bacterium *Borrelia hermsii*," *Nature*, 318:257–263, 1985.

Restrepo and Barbour; "Antigen diversity in the bacterium *B. hermsii* through 'somatic' mutations in rearranged vmp genes," *Cell*, 78:867–876, 1994.

Restrepo, Carter, Barbour, "Activation of a vmp pseudogene in *Borrelia hermsii*: an alternate mechanism of antigenic variation during relapsing fever," *Mol. Microbiol.*, 13:287–299, 1994.

Restrepo, Kitten, Carter, Infante, Barbour, "Subtelomeric expression regions of *Borrelia hermsii* linear plasmids are highly polymorphic," *Mol. Microbiol.*, 6:3299–3311, 1992.

Robertson and Meyer, "Genetic variation in pathogenic bacteria," *Trends Genet.*, 8:422–427, 1992.

Rosa, Samuels, Hogan, Stevenson, Casjens, Tilly, "Directed insertion of a selectable marker into a circular plasmid of *Borrelia burgdorferi*," *J. Bacterial.*, 178:5946–5953, 1996.

Rosa, Schwan, Hogen, "Recombination between genes encoding major surface proteins A and B of *Borrelia burgdorferi*," *Mol. Microbiol.*, 6:3031–3040, 1992.

Rudel, Van Putten, Gibbs, Haas, Meyer, "Interaction of two variable proteins (PilE and PilC) required for pilus-mediated adherence of Neisseria gonorrhoeae to human epithelial cells," *Mol. Microbiol.*, 6:3439–3450, 1992.

Sadziene, Rosa, Thompson, Hogan, Barbour, "Antibody-resistant mutations of *Borrelia burgdorferi*: in vitro selection and characterization," *J. Exp. Med.*, 176:799–809, 1992.

Sambrook, Fritsch, Maniatis, "Molecular cloning: a laboratory manual," (Cold Spring Harbor, N.Y.: Cold Spring Harbor Laboratory Press), 1989.

Samuels, Mach, Garon, "Genetic transformation of the Lyme disease agent *Borrelia burgdorferi* with coumarin-resistant gyrB," *J. Bacteriol.*, 176:6045–6049, 1994.

Schutzer, "Lyme disease: Molecular and immunologic approaches. In: *Current communications in cell and molecular biology*," J. Inglis and J. A. Witkowski, eds. (Cold Spring Harbor, N.Y.: Cold Spring Harbor Laboratory Press).

Schwann et al., "Changes in infectivity and plasmid profile of the Lyme disease spirochete, *Borrelia burgdorferi*, as a result of in vitro cultivation," *Infect. Immun.*, 56:1831–1836, 1988a.

Schwann, Burgdorfer, Schrumpg, Karstens, "The urinary bladder, a consistent source of *Borelia burgdorferi* in experimentally infected white-footed mice (*Peromyscus leucopcus*)," *J. Clin. Microbiol.* 26:893–895, 1988b.

Schwann, Karstens, Schrumpf, Simpson, "Changes in antigenic reactivity of *Borrelia burgdorferi*, the Lyme disease spirochete, during persistent infection of mice," *Can. J. Microbiol.*, 37:450–454, 1991.

Seal, Jackson, Daniels, "Isolation of a Pseudomonas solanacearum-specific DNA probe by subtraction hybridization and construction of species-specific oligonucleotide primers for sensitive detection by the polymerase chain reaction," *Appl. Environ. Microbiol*, 58:3751–3758, 1992.

Segal, Hagblom, Seifert, So, "Antigenic variation of gonococcal pilus involves assembly of separated silent gene segments," *Proc. Natl. Acad. Sci. USA*, 83:2177–2181, 1986.

Seifert and So, "Genetic mechanisms of bacterial antigenic variation," *Microbiol. Rev.*, 52:327–336, 1988.

Steere, "Lyme disease," *N. Engl. J. Med.*, 321:586–596, 1989.

Stevenson, Bockenstedt, Barthold, "Expression and gene sequence of outer surface protein C of *Borelia burgdorferi* reisolated from chronically infected mice," *Infect. Immun.*, 62:3568–3571, 1994.

Stoenner, Dodd, Larsen, "Antigenic variation of *Borrelia hermsii*," *J. Exp. Med.*, 156:1297–1311, 1982.

Swanson and Koomey, "Mechanisms for variation of pili and outer membrane protein II in Neisseria gonorrhoeae," D. E. Berg and M. M. Howe, Eds. (Washington, D.C.: American Society for Microbiology).

Thiessen et al., "Evolution of the *Borelia burgdorferi* outer surface protein OspC," *J. Bacteriol.*, 177:3036–3044, 1995.

Wainwright, Pritchard, Seifert, "A conserved DNA sequence is required for efficient gonococcal pilin antigenic variation," *Mol. Microbiol.*, 13:75–87, 1994.

Walker, Howell, You, Hoffmaster, Heath, Weinstock, Norris, "Physical map of the genome of *Treponema pallidum* subsp. Pallidum (Nichols)," *J. Bacteriol.*, 177:1797–1804, 1995.

Wilske, Barbour, Bergstrom, Burman, Restrepo, Rosa, Schwan, Soutschek, Wallich, "Antigenic variation and strain heterogeneity in Borrelia spp," *Res. Microbiol*, 143:583–596, 1992.

Wu and Tokunaga, "Biogenesis of lipoproteins in bacteria," *Curr. Top. Microbiol. Immunol.*, 125:127–157, 1986.

Xu, Kodner, Coleman, Johnson, "Correlation of plasmids with infectivity of *Borrelia burgdorferi* senso stricto type strain B31," *Infect. Immun.*, 64:3870–3876, 1996.

Xu and Johnson, "Analysis and comparison of plasmid profile of *Borelia burgdorferi* sensu lato strains," *J. Clin. Microbiol.*, 33:2679–2685, 1995.

What is claimed is:

1. A method of assaying for Borrelia infection comprising:
    (a) obtaining a sample from a subject;
    (b) obtaining an antibody that binds immunologically to an epitope of SEQ ID NO: 15 or a polypeptide consisting of an epitope of SEQ ID NO: 15;
    (c) admixing the sample and the antibody that binds immunologically to an epitope of SEQ ID NO: 15 or the polypeptide consisting of an epitope of SEQ ID NO: 15; and
    (d) determining whether inummologic binding occurs between the antibody that binds immunologically to an epitope of SEQ ID NO: 15 and a polypeptide in the sample or the polypeptide consisting of an epitope of SEQ ID NO: 15 and an antibody in the sample;
wherein immunologic binding is indicative of Borrelia infection.

2. The method of claim 1, wherein the Borrelia infection is further defined as Lyme disease.

3. The method of claim 1, wherein the sample is blood.

4. The method of claim 1, wherein the sample is urine.

5. The method of claim 1, wherein the assay is an immunoassay.

6. The method of claim 5, wherein the immunoassay is an enzyme immunoassay.

7. The method of claim 6, wherein the enzyme immunoassay comprises an ELISA.

8. The method of claim 5, wherein the immunoassay assay comprises western blotting.

9. The method of claim 5, wherein the immunoassay comprises immunoprecipitation.

10. The method of claim 5, wherein the immunoassay comprises a radioimmunoassay.

11. The method of claim 1, wherein the subject is an animal.

12. The method of claim 11, wherein the animal is a human.

13. The method of claim 11, wherein the animal is a dog, deer, or mouse.

14. The method of claim 1 further defined as determining whether there is immunologic binding between an antibody that binds immunologically to an epitope of SEQ ID NO: 15 and a polypeptide in the sample.

15. The method of claim 1 further defined as determining whether there is immunologic binding between a polypeptide consisting of an epitope of SEQ ID NO: 15 and an antibody in the sample.

16. The method of claim 15, wherein the polypeptide consists of amino acid sequence SEQ ID NO: 15.

17. The method of claim 15, wherein determining immunological binding comprises an ELISA.

18. The method of claim 15, wherein determining immunological binding comprises western blotting.

19. The method of claim 15, wherein determining immunological binding comprises immunoprecipitation.

20. The method of claim 15, wherein determining immunological binding comprises radioimmunoassay.

21. A kit for use in diagnosing Lyme disease in a subject comprising:
    (a) a suitable container; and
    (b) a first container including an antibody that binds immunologically to an epitope of SEQ ID 15 or a polypeptide consisting of an epitope of SEQ ID NO: 15.

22. The kit of claim 21, wherein the antibody is a monoclonal antibody.

23. The kit of claim 21, wherein the antibody is a polyclonal antibody.

24. The kit of claim 21, wherein the antibody is labeled.

25. The kit of claim 21, wherein the polypeptide is labeled.

26. The kit of claim 21, wherein the kit comprises an antibody that binds immunologically to an epitope of SEQ ID NO: 15.

27. The kit of claim 21, wherein the kit comprises a polypeptide consisting of an epitope of SEQ ID NO: 15.

28. The method of claim 15, wherein the polypeptide consisting of an epitope of SEQ ID NO: 15 is 5 to 25 amino acids in length.

29. The method of claim 28, wherein the polypeptide consisting of an epitope of SEQ ID NO: 15 is 8 to 20 amino acids in length.

30. The kit of claim 22, wherein the polypeptide consisting of an epitope of SEQ ID NO: 15 is 5 to 25 amino acids in length.

31. The kit of claim 30, wherein the polypeptide consisting of an epitope of SEQ ID NO: 15 is 8 to 20 amino acids in length.

* * * * *

UNITED STATES PATENT AND TRADEMARK OFFICE
CERTIFICATE OF CORRECTION

PATENT NO. : 6,740,744 B2
DATED : May 25, 2004
INVENTOR(S) : Steven J. Norris et al.

It is certified that error appears in the above-identified patent and that said Letters Patent is hereby corrected as shown below:

Column 126,
Line 56, please delete "22" and insert -- 27 -- therefor.

Signed and Sealed this

Fifth Day of October, 2004

JON W. DUDAS
*Director of the United States Patent and Trademark Office*

UNITED STATES PATENT AND TRADEMARK OFFICE
CERTIFICATE OF CORRECTION

PATENT NO. : 6,740,744 B2
DATED : May 25, 2004
INVENTOR(S) : Steven J. Norris et al.

It is certified that error appears in the above-identified patent and that said Letters Patent is hereby corrected as shown below:

Column 1,
Line 10, add -- The government owns rights in the present invention pursuant to grant number AI037277 from the National Institutes of Health. --.

Signed and Sealed this

Twenty-seventh Day of December, 2005

JON W. DUDAS
*Director of the United States Patent and Trademark Office*

UNITED STATES PATENT AND TRADEMARK OFFICE
CERTIFICATE OF CORRECTION

PATENT NO.       : 6,740,744 B2  
APPLICATION NO.  : 10/143024  
DATED            : May 25, 2004  
INVENTOR(S)      : Norris et al.

It is certified that error appears in the above-identified patent and that said Letters Patent is hereby corrected as shown below:

In column 49, line 65, delete "FIG. 8" and insert --FIG. 5A-- therefor.

In column 50, line 13, delete "FIG. 9" and insert --FIG. 3B-- therefor.

In column 50, line 14, delete "FIG. 10" and insert --FIG. 5C-- therefor.

In column 50, line 19, delete "FIG. 11" and insert --FIG. 5B-- therefor.

Signed and Sealed this

Twentieth Day of February, 2007

JON W. DUDAS  
*Director of the United States Patent and Trademark Office*

SEQUENCE LISTING

<160> NUMBER OF SEQ ID NOS: 50

<210> SEQ ID NO 1
<211> LENGTH: 1227
<212> TYPE: DNA
<213> ORGANISM: Borrelia burgdorferi
<220> FEATURE:
<221> NAME/KEY: CDS
<222> LOCATION: (75)..(1142)

<400> SEQUENCE: 1

```
acctacactt g

```
aaa aat ccg att gct gct gct att ggg gat aaa gat ggg ggt gcg gag    878
Lys Asn Pro Ile Ala Ala Ala Ile Gly Asp Lys Asp Gly Gly Ala Glu
        255                 260                 265 ttt ggt cag gat gag atg aag aag gat gat cag att gct gct gct att    926
Phe Gly Gln Asp Glu Met Lys Lys Asp Asp Gln Ile Ala Ala Ala Ile
    270                 275                 280 gct ttg agg ggg atg gct aag gat gga aag ttt gct gtg aag gat ggt    974
Ala Leu Arg Gly Met Ala Lys Asp Gly Lys Phe Ala Val Lys Asp Gly
285                 290                 295                 300 gag aaa gag aag gct gag ggg gct att aag gga gct gct gag tct gca   1022
Glu Lys Glu Lys Ala Glu Gly Ala Ile Lys Gly Ala Ala Glu Ser Ala
                305                 310                 315 gtt cgc aaa gtt tta ggg gct att act ggg cta ata gga gac gcc gtg   1070
Val Arg Lys Val Leu Gly Ala Ile Thr Gly Leu Ile Gly Asp Ala Val
                320                 325                 330 agt tcc ggg cta agg aaa gtc ggt gat tca gtg aag gct gct agt aaa   1118
Ser Ser Gly Leu Arg Lys Val Gly Asp Ser Val Lys Ala Ala Ser Lys
                335                 340                 345 gaa aca cct cct gcc ttg aat aag tgatttaatt aagtgtatgg acacgactat  1172
Glu Thr Pro Pro Ala Leu Asn Lys
    350                 355 gccctcatga ttgaggaaat agtcgagaga tatatatact aaaagataat aaata      1227
```

<210> SEQ ID NO 2
<211> LENGTH: 356
<212> TYPE: PRT
<213> ORGANISM: Borrelia burgdorferi

<400> SEQUENCE: 2

```
Met Lys Lys Ile Ser Ser Ala Ser Leu Leu Thr Thr Phe Phe Val Phe
  1               5                  10                  15

Ile Asn Cys Lys Ser Gln Val Ala Asp Lys Asp Pro Thr Asn Lys
                 20                  25                  30

Phe Tyr Gln Ser Val Ile Gln Leu Gly Asn Gly Phe Leu Asp Val Phe
             35                  40                  45

Thr Ser Phe Gly Gly Leu Val Ala Glu Ala Phe Gly Phe Lys Ser Asp
         50                  55                  60

Pro Lys Lys Ser Asp Val Lys Thr Tyr Phe Thr Val Ala Ala Lys
 65                  70                  75                  80

Leu Glu Lys Thr Lys Thr Asp Leu Asn Ser Leu Pro Lys Glu Lys Ser
                 85                  90                  95

Asp Ile Ser Ser Thr Thr Gly Lys Pro Asp Ser Thr Gly Ser Val Gly
            100                 105                 110

Thr Ala Val Glu Gly Ala Ile Lys Glu Val Ser Glu Leu Leu Asp Lys
        115                 120                 125

Leu Val Lys Ala Val Lys Thr Ala Glu Gly Ala Ser Ser Gly Thr Ala
    130                 135                 140

Ala Ile Gly Glu Val Val Ala Asp Ala Asp Ala Lys Val Ala Asp
145                 150                 155                 160

Lys Ala Ser Val Lys Gly Ile Ala Lys Gly Ile Lys Glu Ile Val
                165                 170                 175

Ala Ala Gly Gly Ser Glu Lys Leu Lys Ala Val Ala Ala Lys Gly
            180                 185                 190

Glu Asn Asn Lys Gly Ala Gly Lys Leu Phe Gly Lys Ala Gly Ala Ala
        195                 200                 205
```

```
Ala His Gly Asp Ser Glu Ala Ala Ser Lys Ala Ala Gly Ala Val Ser
    210                 215                 220

Ala Val Ser Gly Glu Gln Ile Leu Ser Ala Ile Val Thr Ala Ala Asp
225                 230                 235                 240

Ala Ala Glu Gln Asp Gly Lys Lys Pro Glu Ala Lys Asn Pro Ile
            245                 250                 255

Ala Ala Ala Ile Gly Asp Lys Asp Gly Ala Glu Phe Gly Gln Asp
                260                 265                 270

Glu Met Lys Lys Asp Asp Gln Ile Ala Ala Ala Ile Ala Leu Arg Gly
        275                 280                 285

Met Ala Lys Asp Gly Lys Phe Ala Val Lys Asp Gly Glu Lys Glu Lys
    290                 295                 300

Ala Glu Gly Ala Ile Lys Gly Ala Ala Glu Ser Ala Val Arg Lys Val
305                 310                 315                 320

Leu Gly Ala Ile Thr Gly Leu Ile Gly Asp Ala Val Ser Ser Gly Leu
                325                 330                 335

Arg Lys Val Gly Asp Ser Val Lys Ala Ala Ser Lys Glu Thr Pro Pro
            340                 345                 350

Ala Leu Asn Lys
        355

<210> SEQ ID NO 3
<211> LENGTH: 7766
<212> TYPE: DNA
<213> ORGANISM: Borrelia burgdorferi
<220> FEATURE:
<221> NAME/KEY: modified_base
<222> LOCATION: (127)
<223> OTHER INFORMATION: R = A OR G

<400> SEQUENCE: 3
gctggtgctg gtaatgctgg ggacagtgag gctgctagca aggcggctgg tgctgttagt      60
gctgttagtg gggagcagat attaagtgcg attgttaagg ctgctggtga ggctgcgcag     120
gatggaraga agcctgggga ggctaaaaat ccgattgctg ctgctattgg aagggtaat     180 gaggatggtg cggagtttaa ggatgagatg aagaaggatg atcagattgc tgctgctatt     240
gctttgaggg ggatggctaa ggatggaaag tttgctgtga agaatgatga aaagggaag     300 gctgaggggg ctattaaggg agctggcgag ttgttggata agctggtaaa agctgtaaag     360
acagctgagg gggcttcaag tggtactgct gcaattggag aagttgtggc tgatgataat     420
gctgcgaagg ttgctgataa ggcgagtgtg aaggggattg ctaagggat aaaggagatt     480 gttgaagctg ctgggggggag taaaaagctg aaagttgctg ctgctaaaga gggcaatgaa     540
aaggcaggga agttgtttgg aaagttgat gctgctcatg ctggggacag tgaggctgct     600 agcaaggcg ctggtgctgt tagtgctgtt agtggggagc agatattaag tgcgattgtt     660
aaggctgctg gtgcggctgc tggtgatcag gagggaaaga agcctgggga tgctaaaaat     720
ccgattgctg ctgctattgg aagggtgat gcggagaatg gtgcggagtt taatcatgat     780
gggatgaaga aggatgatca gattgctgct gctattgctt tgaggggat ggctaaggat     840 ggaaagtttg ctgtgaagag tggtggtggt gagaaaggga aggctgaggg ggctattaag     900
ggagctgctg agttgttgga taagctggta aaagctgtaa agacagctga ggggcttca     960 agtggtactg atgcaattgg agaagttgtg ctaatgctg gtgctgcaaa ggttgctgat    1020
aaggcgagtg tgacggggat tgctaagggg ataaaggaga ttgttgaagc tgctgggggg    1080
agtgaaaagc tgaaagttgc tgctgctaca ggggagagta ataaagggc agggaagttg    1140
```

```
tttgggaagg ctggtgctgg tgctaatgct ggggacagtg aggctgctag caaggcggct    1200
ggtgctgtta gtgctgttag tggggagcag atattaagtg cgattgttaa ggctgctgat    1260
gcggctgatc aggagggaaa gaagcctggg gatgctacaa atccgattgc tgctgctatt    1320
gggaagggta atgaggagaa tggtgcggag tttaaggatg agatgaagaa ggatgatcag    1380
attgctgctg ctattgcttt gagggggatg gctaaggatg gaaagtttgc tgtgaaggat    1440
ggtggtgaga aagggaaggc tgaggggget attaagggag ctgctgagtt gttggataag    1500
ctggtaaaag ctgtaaagac agctgagggg gcttcaagtg gtactgatgc aattggagaa    1560
gttgtggata tgctgcgaa ggctgctgat aaggcgagtg tgacggggat tgctaagggg    1620
ataaaggaga ttgttgaagc tgctgggggg agtgaaaagc tgaaagttgc tgctgctaca    1680
ggggagaata ataaagaggc agggaagttg tttgggaagg ctggtgctga tgctaatggg    1740
gacagtgagg ctgctagcaa ggcggctggt gctgttagtc tgttagtgg ggagcagata    1800 ttaagtgcga ttgttaaggc tgcggctgct ggtgcggctg atcaggatgg agagaagcct    1860
ggggatgcta aaaatccgat tgctgctgct attgggaagg taatgcgga tgatggtgcg    1920 gattttggtg atgggatgaa gaaggatgat cagattgctg ctgctattgc tttgaggggg    1980
atggctaagg atgaaagtt tgctgtgaag aaggatgaga agggaaggc tgaggggct    2040 attaagggag ctagcgagtt gttggataag ctggtaaaag ctgtaaagac agctgagggg    2100
gcttcaagtg gtactgctgc aattggagaa gttgtggata tgctgcgaa ggctgctgat    2160 aaggatagtg tgacggggat tgctaagggg ataaaggaga ttgttgaagc tgcagggggg    2220
agtgaaaagc tgaaagttgc tgctgctaaa ggggagaata ataaaggggc agggaagttg    2280
tttgggaagg ctggtgctaa tgctcatggg gacagtgagg ctgctagcaa ggcggctggt    2340
gctgttagtc tgttagtgg ggaacagata ttaagtgcga ttgttaaggc tgctggtgag    2400
gctgctggtg atcaggaggg aaagaagcct gaggaggcta aaaatccgat tgctgctgct    2460
attggggata aagatgggga tgcggagttt aatcaggatg ggatgaagaa ggatgatcag    2520
attgctgctg ctattgcttt gagggggatg gctaaggatg gaaagtttgc tgtgaaggat    2580
ggtggtgaga aagagaaggc tgaggggget attaagggag ttagcgagtt gttggataag    2640
ctggtaaaag ctgtaaagac agctgagggg gcttcaagtg gtactgctgc aattggagaa    2700
gttgtggctg atgctgctaa ggttgctgat aaggcgagtg tgacggggat tgctaagggg    2760
ataaaggaga ttgttgaagc tgctggggac agtgaggctg ctagcaaggc agctggtgct    2820
gttagtgctg ttagtgggga gcagatatta agtgcgattg ttaaggctgc ggctgctggt    2880
gcggctgagc aggatggaga gaagcctgca gaggctaaaa atccgattgc tgctgctatt    2940
gggaagggtg atggggatgc ggattttggt gaggatggga tgaagaagga tgatcagatt    3000
gctgctgcta ttgcttttgag ggggatggct aaggatggaa agtttgctgt gaagaatgat    3060
gagaaaggga aggctgaggg ggctattaag ggagctgctg caattggaga agttgtggat    3120
aatgctggtg ctgcgaaggc tgctgataag gatagtgtga aggggattgc taagggata    3180 aaggagattg ttgaagctgc tggggggagt gaaaagctga agctgctgc tgctgaaggg    3240 gagaataata aaaggcagg gaagttgttt gggaaagttg atggtgctgc tggggacagt    3300
gaggctgcta gcaaggcggc tggtgctgtt agtgctgtta gtggggagca gatattaagt    3360
gcgattgtta aggctgctgg tgaggctgag caggatggag agaagcctga ggatgctaaa    3420
aatccgattg ctgctgctat tgggaagggt aatgggatg gtgcggagtt tgatcaggat    3480
```

```
gagatgaaga aggatgatca gattgctgct gctattgctt tgaggggat ggctaaggat      3540 ggaaagtttg ctgtgaaggg taataatgag aaagagaagg ctgaggggc tattaaagaa      3600 gttagcgagt tgttggataa gctggtaaca gctgtaaaga cagctgaggg ggcttcaagt      3660
ggtactgatg caattggaga agttgtggat aatgatgcta aggttgctga taaggcgagt      3720
gtgacgggga ttgctaaggg gataaaggag attgttgaag ctgctagggg gagtgaaaag      3780
ctgaaagttg ctgctgctaa agagggcaat gaaaaggcag ggaagttgtt tgggaaggct      3840
ggtgctaatg ctcatgggga cagtgaggct gctagcaagg cggctggtgc tgttagtgct      3900
gttagtgggg agcagatatt aagtgcgatt gttaaggctg cggatgcggc tgagcaggat      3960
ggaaagaagc ctgcagatgc tacaaatccg attgctgctg ctattgggaa taaagatgag      4020
gatgcggatt ttggtgatgg gatgaagaag gatgatcaga ttgctgctgc tattgctttg      4080 aggggatgg ctaaggatgg aaagtttgct gtgaagggta ataatgagaa agggaaggct      4140 gaggggctt caagtggtac tgatgcaatt ggagaagttg tggataatga tgcgaaggct      4200
gctgataagg cgagtgtgac ggggattgct aaggggataa aggagattgt tgaagctgct      4260
ggggggagtg aaaagctgaa agctgttgct gctgctacaa gggagaataa taaagaggca      4320
gggaagttgt ttgggaaagt tgatgatgct catgctgggg acagtgaggc tgctagcaag      4380
gcggctggtg ctgttagtgc tgttagtggg gagcagatat taagtgcgat tgttacggct      4440
gcggctgctg gtgagcagga tggagagaag cctgcagagg ctacaaatcc gattgctgct      4500
gctattggga agggtaatga ggatggtgcg gattttggta aggatgagat gaagaaggat      4560
gatcagattg ctgctgctat tgctttgagg gggatggcta aggatggaaa gtttgctgtg      4620
aagagtaatg atggtgagaa agggaaggct gagggggcta ttaaggaagt tagcgagttg      4680
ttggataagc tggtaaaagc tgtaaagaca gctgaggggg cttcaagcgg tactgatgca      4740
attggagaag ttgtggctaa tgctggtgct gcgaaggctg ctgataaggc gagtgtgacg      4800
gggattgcta aggggataaa ggagattgtt gaagctgctg ggggagtaa aaagctgaaa      4860 gctgctgctg ctgaagggga gaataataaa aggcagggga gttgtttgg gaaggctggt      4920 gctggtgctg gtgctaatgg ggacagtgag gctgctagca aggcggctgg tgctgttagt      4980
gctggttagt gtgggagca gatattaagt gcgattgtta cggctgctgg tgcggctgct      5040
agtgaggctg atcaggaggg aaagaagcct gcagatgcta caaatccgat tgctgctgct      5100
attgggaagg tgatgcgga aatggtgcg gattttggtg atgggatgaa gaaggatgat      5160
cagattgctg ctgctattgc tttgagggg atggctaagg atggaaagtt tgctgtgaag      5220
aatgatgatg agaaagggaa ggctgagggg gctattaagg gagctagcga gttgttggat      5280
aagctggtaa cagctgtaaa gacagctgag ggggcttcaa gtggtactga tgcaattgga      5340
gaagttgtgg ctgatgctgc gaaggctgct gataaggata gtgtgaaggg gattgctaag      5400
gggataaagg agattgttga agctgctggg gggagtgaaa agctgaaagt tgctgctgct      5460
aaagagggca atgaaaaggc agggaagttg tttgggaagg ttggtgatgc tgctcatgct      5520
ggggacagtg aggctgctag caaggcggct ggtgctgtta gtgctgttag tggggagcag      5580
atattaagtg cgattgttac ggctgctggt gcggctgagc aggagggaaa gaagcctgca      5640
gaggctaaaa atccgattgc tgctgctatt gggaaggta tgagaatgg tgcggagttt      5700 aaggatgaga tgaagaagga tgatcagatt gctgctgcta ttgctttgag gggatggct      5760 aaggatggaa agtttgctgt gaagaaggat aataatgaga agggaaggc tgaggggct      5820 attaaggaag ttagcgagtt gttggataag ctggtaacag ctgtaaagac agctgaggag      5880
```

```
gcttcaagtg gtactgctgc aattggagaa gttgtggctg atgatgctgc tgcgaaggct    5940
gctgataagg agagtgtgaa ggggattgct aagggataa aggagattgt tgaagctgct    6000 gggggagta aaagctgaa agttgctgct gctacagggg agaataataa aaaggcaggg     6060
aagttgtttg ggaaagttga tgctggtaat gctgggaca gtgaggctgc tagcaaggcg     6120
gctggtgctg ttagtgggga gcagatatta agtgcgattg ttaaggctgc tggtgcggct     6180
gctggtgatc aggagggaaa gaagcctggg gatgctaaaa atccgattgc tgctgctatt     6240 gggaaggtg atgcggagaa tggtgcggag tttgatcatg agatgaagaa ggatgatcag     6300
attgctgctg ctattgcttt gagggggatg gctaaggatg gaaagtttgc tgtgaagagt     6360
ggtgatgaga agggaaggc tgagggggct attaaggag ctagcgagtt gttggataag     6420
ctggtaaaag ctgtgtaaag acagctgagg gggcttcaag tggtactgat gcaattggag     6480
aagttgtggc taatgatgct gctgcgaagg ttgctgataa ggagagtgtg acggggattg     6540 ctaagggat aaaggagatt gttgaagctg ctgggggag tgaaaagctg aagttgctg       6600 ctgctacaag ggagaataat aaaaaggcag ggaagttgtt tgggaaagct ggtgatgctg     6660
ctaatgggga cagtgaggct gctagcaagg cggctggtgc tgttagtgct gttagtgggg     6720
agcagatatt aagtgcgatt gttacggctg cagctgctgg tgcggctgag caggagggaa     6780
agaagcctga ggaggctaaa atccgattg ctgctgctat tgggaaggt aatgcggatg      6840 atggtgcgga gtttaataag gaggggatga agaaggatga tcagattgct gctgctattg     6900
ctttgagggg gatggctaag gatggaaagt tgctgtgaa gagtggtggt gagaaggga      6960 aggctgaggg ggctattaaa gaagttagcg agttgttgga taagctggta acaactgtaa    7020
agacagctga gggggcttca atggtactg atgcaattgg aaaagttgtg gataataata    7080
atgctgcgaa ggctgctgat aaggcgagtg tgacggggat tgctaagggg ataaaggaga    7140
ttgttgaagc tgctgggggg agtagtgaaa agctgaaagc tgttgctgct gctaaggggg    7200
agagcaatga aaaggcaggg aagttgtttg ggaaggctgg tgctgctgct ggggacagtg    7260
aggctgctag caaggcggct ggtgctgtta gtgctgttag tggggagcag atattaagtg    7320
cgattgttaa ggctgctggt gcggctgatc aggagggaaa gaagcctgag gatgctaaaa    7380
atccgattgc tgctgctatt ggggataaag atggggtgc ggagttaaat catgagatga    7440
agaaggatga tcagattgct gctgctattg ctttgagggg gatggctaag gatgaaagt     7500 ttgctgtgaa gagtggtggt ggtgagaaag agaaggctga gggggctatt aaagaagtta    7560
gcgagttgtt ggataagctg gtaaaagctg tgtaaagaca gctgaggggg cttcaagtgg    7620
tactgatgca attggagaag ttgtggctga taatagtgct gcgaaggctg ctgatgaggc    7680
gagtgtgacg gggattgcta agggaataaa ggagattgtt gaagctgctg ggggagtga    7740 aaagctgaaa gttgctgctg ctgcag                                        7766

<210> SEQ ID NO 4
<211> LENGTH: 16
<212> TYPE: DNA
<213> ORGANISM: Borrelia burgdorferi

<400> SEQUENCE: 4
agtacgggga aaccag                                                     16

<210> SEQ ID NO 5
<211> LENGTH: 22
<212> TYPE: DNA
```

<213> ORGANISM: Borrelia burgdorferi

<400> SEQUENCE: 5
ctttgcgaac gcagactcag ca                                              22

<210> SEQ ID NO 6
<211> LENGTH: 21
<212> TYPE: DNA
<213> ORGANISM: Borrelia burgdorferi

<400> SEQUENCE: 6
agtggggaga tattaagtgc g                                               21

<210> SEQ ID NO 7
<211> LENGTH: 22
<212> TYPE: DNA
<213> ORGANISM: Borrelia burgdorferi

<400> SEQUENCE: 7
ctttgcgaac gcagactcag ca                                              22

<210> SEQ ID NO 8
<211> LENGTH: 17
<212> TYPE: DNA
<213> ORGANISM: Borrelia burgdorferi

<400> SEQUENCE: 8 gaggggcta ttaagga                                                     17

<210> SEQ ID NO 9
<211> LENGTH: 12
<212> TYPE: DNA
<213> ORGANISM: Borrelia burgdorferi

<400> SEQUENCE: 9
ccggaattcc gg                                                         12

<210> SEQ ID NO 10
<211> LENGTH: 22
<212> TYPE: DNA
<213> ORGANISM: Borrelia burgdorferi

<400> SEQUENCE: 10
ctttgcgaac gcagactcag ca                                              22

<210> SEQ ID NO 11
<211> LENGTH: 27
<212> TYPE: DNA
<213> ORGANISM: Borrelia burgdorferi

<400> SEQUENCE: 11
gcggatccag tacgacgggg aaaccag                                         27

<210> SEQ ID NO 12
<211> LENGTH: 28
<212> TYPE: DNA
<213> ORGANISM: Borrelia burgdorferi

<400> SEQUENCE: 12
gcggatcccc ttctctttct caccatcc                                        28

<210> SEQ ID NO 13
<211> LENGTH: 356

```
<212> TYPE: PRT
<213> ORGANISM: Borrelia burgdorferi

<400> SEQUENCE: 13

Met Lys Lys Ile Ser Ser Ala Ser Leu Leu Thr Thr Phe Phe Val Phe
 1               5                  10                  15

Ile Asn Cys Lys Ser Gln Val Ala Asp Lys Asp Pro Thr Asn Lys
            20                  25                  30

Phe Tyr Gln Ser Val Ile Gln Leu Gly Asn Gly Phe Leu Asp Val Phe
        35                  40                  45

Thr Ser Phe Gly Gly Leu Val Ala Glu Ala Phe Gly Phe Lys Ser Asp
    50                  55                  60

Pro Lys Lys Ser Asp Val Lys Thr Tyr Phe Thr Thr Val Ala Ala Lys
65                  70                  75                  80

Leu Glu Lys Thr Lys Thr Asp Leu Asn Ser Leu Pro Lys Glu Lys Ser
                85                  90                  95

Asp Ile Ser Ser Thr Thr Gly Lys Pro Asp Ser Thr Gly Ser Val Gly
            100                 105                 110

Thr Ala Val Glu Gly Ala Ile Lys Glu Val Ser Glu Leu Leu Asp Lys
        115                 120                 125

Leu Val Lys Ala Val Lys Thr Ala Glu Gly Ala Ser Ser Gly Thr Ala
    130                 135                 140

Ala Ile Gly Glu Val Val Ala Asp Ala Asp Ala Ala Lys Val Ala Asp
145                 150                 155                 160

Lys Ala Ser Val Lys Gly Ile Ala Lys Gly Ile Lys Glu Ile Val Glu
                165                 170                 175

Ala Ala Gly Gly Ser Glu Lys Leu Lys Ala Val Ala Ala Lys Gly
            180                 185                 190

Glu Asn Asn Lys Gly Ala Gly Lys Leu Phe Gly Lys Ala Gly Ala Ala
        195                 200                 205

Ala His Gly Asp Ser Glu Ala Ala Ser Lys Ala Ala Gly Ala Val Ser
    210                 215                 220

Ala Val Ser Gly Glu Gln Ile Leu Ser Ala Ile Val Thr Ala Ala Asp
225                 230                 235                 240

Ala Ala Glu Gln Asp Gly Lys Lys Pro Glu Glu Ala Lys Asn Pro Ile
                245                 250                 255

Ala Ala Ala Ile Gly Asp Lys Asp Gly Gly Ala Glu Phe Gly Gln Asp
            260                 265                 270

Glu Met Lys Lys Asp Asp Gln Ile Ala Ala Ile Ala Leu Arg Gly
        275                 280                 285

Met Ala Lys Asp Gly Lys Phe Ala Val Lys Asp Gly Glu Lys Glu Lys
    290                 295                 300

Ala Glu Gly Ala Ile Lys Gly Ala Ala Glu Ser Ala Val Arg Lys Val
305                 310                 315                 320

Leu Gly Ala Ile Thr Gly Leu Ile Gly Asp Ala Val Ser Ser Gly Leu
                325                 330                 335

Arg Lys Val Gly Asp Ser Val Lys Ala Ala Ser Lys Glu Thr Pro Pro
            340                 345                 350

Ala Leu Asn Lys
        355

<210> SEQ ID NO 14
<211> LENGTH: 339
<212> TYPE: PRT
<213> ORGANISM: Borrelia burgdorferi
```

<400> SEQUENCE: 14

```
Met Arg Lys Arg Ile Ser Ala Ile Ile Met Thr Leu Phe Met Val Leu
  1               5                  10                  15

Val Ser Cys Asn Ser Gly Gly Val Ala Glu Asp Pro Lys Thr Val Tyr
                 20                  25                  30

Leu Thr Ser Ile Ala Asn Leu Gly Lys Gly Phe Leu Asp Val Phe Val
             35                  40                  45

Thr Phe Gly Asp Met Val Thr Gly Ala Phe Gly Ile Lys Ala Asp Thr
         50                  55                  60

Lys Lys Ser Asp Ile Gly Lys Tyr Phe Thr Asp Ile Glu Ser Thr Met
 65                  70                  75                  80

Thr Ser Val Lys Lys Leu Gln Asp Glu Val Ala Lys Asn Gly Asn
                 85                  90                  95

Tyr Pro Lys Val Lys Thr Ala Val Asp Glu Phe Val Ala Ile Leu Gly
                100                 105                 110

Lys Ile Glu Lys Gly Ala Lys Glu Ala Ser Lys Gly Ala Thr Gly Asp
            115                 120                 125

Val Ile Ile Gly Asn Thr Val Lys Asn Gly Asp Ala Val Pro Gly Glu
        130                 135                 140

Ala Thr Ser Val Asn Ser Leu Val Lys Gly Ile Lys Glu Ile Val Gly
145                 150                 155                 160

Val Val Leu Lys Glu Gly Lys Ala Asp Ala Asp Ala Thr Lys Asp Asp
                165                 170                 175

Ser Lys Lys Asp Ile Gly Lys Leu Phe Thr Ala Thr Thr Asp Ala Asn
                180                 185                 190

Arg Ala Asp Asn Ala Ala Ala Gln Ala Ala Ala Ala Ser Ile Gly Ala
            195                 200                 205

Val Thr Gly Ala Asp Ile Leu Gln Ala Ile Val Gln Ser Lys Glu Asn
        210                 215                 220

Pro Val Ala Asn Ser Thr Asp Gly Ile Glu Lys Ala Thr Asp Ala Ala
225                 230                 235                 240

Glu Ile Ala Val Ala Pro Ala Lys Asp Asn Lys Lys Glu Ile Lys Asp
                245                 250                 255

Gly Ala Lys Lys Asp Ala Val Ile Ala Ala Gly Ile Ala Leu Arg Ala
                260                 265                 270

Met Ala Lys Asn Gly Thr Phe Ser Ile Lys Asn Asn Glu Asp Ala Ala
                275                 280                 285

Val Thr Thr Ile Asn Ser Ala Ala Ser Ala Val Asn Lys Ile Leu
        290                 295                 300

Ser Thr Leu Ile Ile Ala Ile Arg Asn Thr Val Asp Ser Gly Leu Lys
305                 310                 315                 320

Thr Ile Asn Glu Ala Leu Ala Thr Val Lys Gln Glu Asp Lys Ser Val
                325                 330                 335

Glu Ala Thr
```

<210> SEQ ID NO 15
<211> LENGTH: 190
<212> TYPE: PRT
<213> ORGANISM: Borrelia burgdorferi

<400> SEQUENCE: 15

```
Glu Gly Ala Ile Lys Glu Val Ser Glu Leu Leu Asp Lys Leu Val Lys
  1               5                  10                  15
```

```
Ala Val Lys Thr Ala Glu Gly Ala Ser Ser Gly Thr Ala Ala Ile Gly
            20                  25                  30

Glu Val Val Ala Asp Ala Asp Ala Ala Lys Val Ala Asp Lys Ala Ser
            35                  40                  45

Val Lys Gly Ile Ala Lys Gly Ile Lys Glu Ile Val Glu Ala Ala Gly
            50                  55                  60

Gly Ser Glu Lys Leu Lys Ala Val Ala Ala Lys Gly Glu Asn Asn
 65                  70                  75                  80

Lys Gly Ala Gly Lys Leu Phe Gly Lys Ala Gly Ala Ala His Gly
                85                  90                  95

Asp Ser Glu Ala Ala Ser Lys Ala Ala Gly Ala Val Ser Ala Val Ser
                100                 105                 110

Gly Glu Gln Ile Leu Ser Ala Ile Val Thr Ala Ala Asp Ala Ala Glu
                115                 120                 125

Gln Asp Gly Lys Lys Pro Glu Glu Ala Lys Asn Pro Ile Ala Ala Ala
    130                 135                 140

Ile Gly Asp Lys Asp Gly Gly Ala Glu Phe Gly Gln Asp Glu Met Lys
145                 150                 155                 160

Lys Asp Asp Gln Ile Ala Ala Ile Ala Leu Arg Gly Met Ala Lys
                165                 170                 175

Asp Gly Lys Phe Ala Val Lys Asp Gly Glu Lys Glu Lys Ala
                180                 185                 190

<210> SEQ ID NO 16
<211> LENGTH: 169
<212> TYPE: PRT
<213> ORGANISM: Borrelia burgdorferi

<400> SEQUENCE: 16

Met Thr Asn Pro Ser Thr Ala Thr Leu Leu Thr Thr Phe Phe Val Phe
 1               5                  10                  15

Ile Asn Cys Lys Ser Gln Val Ala Asp Lys Ala Ser Val Thr Gly Ile
                20                  25                  30

Ala Lys Gly Ile Lys Glu Ile Val Glu Ala Ala Gly Gly Ser Glu Lys
                35                  40                  45

Leu Lys Val Ala Ala Glu Gly Glu Asn Asn Glu Lys Ala Gly Lys
 50                  55                  60

Leu Phe Gly Lys Ala Gly Ala Gly Asn Ala Gly Asp Ser Glu Ala Ala
 65                  70                  75                  80

Ser Lys Ala Ala Gly Ala Val Ser Ala Val Ser Gly Glu Gln Ile Leu
                85                  90                  95

Ser Ala Ile Val Lys Ala Gly Glu Ala Ala Gln Asp Gly Lys Lys
                100                 105                 110

Pro Gly Glu Ala Lys Asn Pro Ile Ala Ala Ile Gly Lys Gly Asn
    115                 120                 125

Glu Asp Gly Ala Glu Phe Lys Asp Glu Met Lys Lys Asp Asp Gln Ile
    130                 135                 140

Ala Ala Ile Ala Leu Arg Gly Met Ala Lys Asp Gly Lys Phe Ala
145                 150                 155                 160

Val Lys Asn Asp Glu Lys Gly Lys Ala
                165

<210> SEQ ID NO 17
<211> LENGTH: 195
<212> TYPE: PRT
<213> ORGANISM: Borrelia burgdorferi
```

<400> SEQUENCE: 17

| | | | | | | | | | | | | | | | |
|---|---|---|---|---|---|---|---|---|---|---|---|---|---|---|---|
| Glu | Gly | Ala | Ile | Lys | Gly | Ala | Gly | Glu | Leu | Leu | Asp | Lys | Leu | Val | Lys |
| 1 | | | | 5 | | | | | 10 | | | | | 15 | |
| Ala | Val | Lys | Thr | Ala | Glu | Gly | Ala | Ser | Ser | Gly | Thr | Ala | Ala | Ile | Gly |
| | | | 20 | | | | | 25 | | | | | 30 | | |
| Glu | Val | Val | Ala | Asp | Asp | Asn | Ala | Ala | Lys | Val | Ala | Asp | Lys | Ala | Ser |
| | | 35 | | | | | 40 | | | | | 45 | | | |
| Val | Lys | Gly | Ile | Ala | Lys | Gly | Ile | Lys | Glu | Ile | Val | Glu | Ala | Ala | Gly |
| | 50 | | | | | 55 | | | | | 60 | | | | |
| Gly | Ser | Lys | Lys | Leu | Lys | Val | Ala | Ala | Lys | Gly | Glu | Gly | Asn | Glu | |
| 65 | | | | | 70 | | | | | 75 | | | | | 80 |
| Lys | Ala | Gly | Lys | Leu | Phe | Gly | Lys | Val | Asp | Ala | Ala | His | Ala | Gly | Asp |
| | | | | 85 | | | | | 90 | | | | | 95 | |
| Ser | Glu | Ala | Ala | Ser | Lys | Ala | Ala | Gly | Ala | Val | Ser | Ala | Val | Ser | Gly |
| | | | 100 | | | | | 105 | | | | | 110 | | |
| Glu | Gln | Ile | Leu | Ser | Ala | Ile | Val | Lys | Ala | Ala | Gly | Ala | Ala | Ala | Gly |
| | | | 115 | | | | | 120 | | | | | 125 | | |
| Asp | Gln | Glu | Gly | Lys | Lys | Pro | Gly | Asp | Ala | Lys | Asn | Pro | Ile | Ala | Ala |
| | 130 | | | | | 135 | | | | | 140 | | | | |
| Ala | Ile | Gly | Lys | Gly | Asp | Ala | Glu | Asn | Gly | Ala | Glu | Phe | Asn | His | Asp |
| 145 | | | | | 150 | | | | | 155 | | | | | 160 |
| Gly | Met | Lys | Lys | Asp | Asp | Gln | Ile | Ala | Ala | Ala | Ile | Ala | Leu | Arg | Gly |
| | | | | 165 | | | | | 170 | | | | | 175 | |
| Met | Ala | Lys | Asp | Gly | Lys | Phe | Ala | Val | Lys | Ser | Gly | Gly | Gly | Glu | Lys |
| | | | 180 | | | | | 185 | | | | | 190 | | |
| Gly | Lys | Ala | | | | | | | | | | | | | |
| | | 195 | | | | | | | | | | | | | |

<210> SEQ ID NO 18
<211> LENGTH: 179
<212> TYPE: PRT
<213> ORGANISM: Borrelia burgdorferi

<400> SEQUENCE: 18

| | | | | | | | | | | | | | | | |
|---|---|---|---|---|---|---|---|---|---|---|---|---|---|---|---|
| Glu | Gly | Ala | Ile | Lys | Gly | Ala | Ala | Glu | Leu | Leu | Asp | Lys | Leu | Val | Lys |
| 1 | | | | 5 | | | | | 10 | | | | | 15 | |
| Ala | Val | Lys | Thr | Ala | Glu | Gly | Ala | Ser | Ser | Gly | Thr | Asp | Ala | Ile | Gly |
| | | | 20 | | | | | 25 | | | | | 30 | | |
| Glu | Val | Val | Ala | Asn | Ala | Gly | Ala | Ala | Lys | Val | Ala | Asp | Lys | Ala | Ser |
| | | 35 | | | | | 40 | | | | | 45 | | | |
| Val | Thr | Gly | Ile | Ala | Lys | Gly | Ile | Lys | Glu | Ile | Val | Glu | Ala | Ala | Gly |
| | 50 | | | | | 55 | | | | | 60 | | | | |
| Gly | Ser | Glu | Lys | Leu | Lys | Val | Ala | Ala | Ala | Thr | Gly | Glu | Ser | Gly | Ala |
| 65 | | | | | 70 | | | | | 75 | | | | | 80 |
| Asn | Ala | Gly | Asp | Ser | Glu | Ala | Ala | Ser | Lys | Ala | Ala | Gly | Ala | Val | Ser |
| | | | | 85 | | | | | 90 | | | | | 95 | |
| Ala | Val | Ser | Gly | Glu | Gln | Ile | Leu | Ser | Ala | Ile | Val | Lys | Ala | Ala | Asp |
| | | | 100 | | | | | 105 | | | | | 110 | | |
| Ala | Ala | Asp | Gln | Glu | Gly | Lys | Lys | Pro | Gly | Asp | Ala | Thr | Asn | Pro | Ile |
| | | | 115 | | | | | 120 | | | | | 125 | | |
| Ala | Ala | Ala | Ile | Gly | Lys | Gly | Asn | Glu | Glu | Asn | Gly | Ala | Glu | Phe | Lys |
| | 130 | | | | | 135 | | | | | 140 | | | | |
| Asp | Glu | Met | Lys | Lys | Asp | Asp | Gln | Ile | Ala | Ala | Ala | Ile | Ala | Leu | Arg |
| 145 | | | | | 150 | | | | | 155 | | | | | 160 |

```
Gly Met Ala Lys Asp Gly Lys Phe Ala Val Lys Asp Gly Gly Glu Lys
                165                 170                 175

Gly Lys Ala
```

<210> SEQ ID NO 19
<211> LENGTH: 190
<212> TYPE: PRT
<213> ORGANISM: Borrelia burgdorferi

<400> SEQUENCE: 19

```
Glu Gly Ala Ile Lys Gly Ala Ala Glu Leu Leu Asp Lys Leu Val Lys
  1               5                  10                  15

Ala Val Lys Thr Ala Glu Gly Ala Ser Ser Gly Thr Asp Ala Ile Gly
             20                  25                  30

Glu Val Val Asp Asn Ala Ala Lys Ala Ala Asp Lys Ala Ser Val Thr
         35                  40                  45

Gly Ile Ala Lys Gly Ile Lys Glu Ile Val Glu Ala Ala Gly Gly Ser
     50                  55                  60

Glu Lys Leu Lys Val Ala Ala Thr Gly Glu Asn Asn Lys Glu Ala
 65                  70                  75                  80

Gly Lys Leu Phe Gly Lys Ala Gly Ala Asp Ala Asn Gly Asp Ser Glu
                 85                  90                  95

Ala Ala Ser Lys Ala Ala Gly Ala Val Ser Ala Val Ser Gly Glu Gln
                100                 105                 110

Ile Leu Ser Ala Ile Val Lys Ala Ala Ala Gly Ala Ala Asp Gln
            115                 120                 125

Asp Gly Glu Lys Pro Gly Asp Ala Lys Asn Pro Ile Ala Ala Ala Ile
        130                 135                 140

Gly Lys Gly Asn Ala Asp Asp Gly Ala Asp Phe Gly Asp Gly Met Lys
145                 150                 155                 160

Lys Asp Asp Gln Ile Ala Ala Ile Ala Leu Arg Gly Met Ala Lys
                165                 170                 175

Asp Gly Lys Phe Ala Val Lys Lys Asp Glu Lys Gly Lys Ala
                180                 185                 190
```

<210> SEQ ID NO 20
<211> LENGTH: 189
<212> TYPE: PRT
<213> ORGANISM: Borrelia burgdorferi

<400> SEQUENCE: 20

```
Glu Gly Ala Ile Lys Gly Ala Ser Glu Leu Leu Asp Lys Leu Val Lys
  1               5                  10                  15

Ala Val Lys Thr Ala Glu Gly Ala Ser Ser Gly Thr Ala Ala Ile Gly
             20                  25                  30

Glu Val Val Asp Asn Ala Ala Lys Ala Ala Asp Lys Asp Ser Val Thr
         35                  40                  45

Gly Ile Ala Lys Gly Ile Lys Glu Ile Val Glu Ala Ala Gly Gly Ser
     50                  55                  60

Glu Lys Leu Lys Val Ala Ala Lys Gly Glu Asn Asn Lys Gly Ala
 65                  70                  75                  80

Gly Lys Leu Phe Gly Lys Ala Gly Ala Asn Ala His Gly Asp Ser Glu
                 85                  90                  95

Ala Ala Ser Lys Ala Ala Gly Ala Val Ser Ala Val Ser Gly Glu Gln
                100                 105                 110
```

-continued

```
Ile Leu Ser Ala Ile Val Lys Ala Ala Gly Ala Ala Gly Asp Gln
        115                 120                 125

Glu Gly Lys Lys Pro Glu Ala Lys Asn Pro Ile Ala Ala Ile
130                 135                 140

Gly Lys Asp Gly Asp Ala Glu Asn Gly Gln Gly Met Lys Lys Asp
145                 150                 155                 160

Asp Gln Ile Ala Ala Ile Ala Leu Arg Gly Met Ala Lys Asp Gly
                165                 170                 175

Lys Phe Ala Val Lys Asp Gly Glu Lys Glu Lys Ala
            180                 185
```

<210> SEQ ID NO 21
<211> LENGTH: 158
<212> TYPE: PRT
<213> ORGANISM: Borrelia burgdorferi

<400> SEQUENCE: 21

```
Glu Gly Ala Ile Lys Gly Val Ser Glu Leu Leu Asp Lys Leu Val Lys
1               5                   10                  15

Ala Val Lys Thr Ala Glu Gly Ala Ser Ser Gly Thr Ala Ala Ile Gly
            20                  25                  30

Glu Val Val Ala Asp Ala Ala Lys Val Ala Asp Lys Ala Ser Val Thr
        35                  40                  45

Gly Ile Ala Lys Gly Ile Lys Glu Ile Val Glu Ala Ala Gly Asp Ser
    50                  55                  60

Glu Ala Ala Ser Lys Ala Ala Gly Ala Val Ser Ala Val Ser Gly Glu
65                  70                  75                  80

Gln Ile Leu Ser Ala Ile Val Lys Ala Ala Ala Ala Gly Ala Ala Glu
                85                  90                  95

Gln Asp Gly Glu Lys Pro Ala Glu Ala Lys Asn Pro Ile Ala Ala Ala
            100                 105                 110

Ile Gly Lys Gly Asp Gly Asp Ala Asp Phe Gly Glu Asp Gly Met Lys
        115                 120                 125

Lys Asp Asp Gln Ile Ala Ala Ile Ala Leu Arg Gly Met Ala Lys
    130                 135                 140

Asp Gly Lys Phe Ala Val Lys Asn Asp Glu Lys Gly Lys Ala
145                 150                 155
```

<210> SEQ ID NO 22
<211> LENGTH: 169
<212> TYPE: PRT
<213> ORGANISM: Borrelia burgdorferi

<400> SEQUENCE: 22

```
Glu Gly Ala Ile Lys Gly Ala Ala Ala Ile Gly Glu Val Val Asp Asn
1               5                   10                  15

Ala Gly Ala Ala Lys Ala Lys Ala Asp Lys Asp Ser Val Lys Gly Ile Ala
            20                  25                  30

Lys Gly Ile Lys Glu Ile Val Glu Ala Ala Gly Gly Ser Glu Lys Leu
        35                  40                  45

Lys Ala Ala Ala Ala Glu Gly Glu Asn Asn Lys Lys Ala Gly Lys Leu
    50                  55                  60

Phe Gly Lys Val Asp Gly Ala Ala Gly Asp Ser Glu Ala Ala Ser Lys
65                  70                  75                  80

Ala Ala Gly Ala Val Ser Ala Val Ser Gly Glu Gln Ile Leu Ser Ala
                85                  90                  95
```

```
Ile Val Lys Ala Ala Gly Glu Ala Gln Asp Glu Lys Lys Pro Glu
            100                 105                 110

Asp Ala Lys Asn Pro Ile Ala Ala Ile Gly Lys Gly Asn Gly Asp
            115                 120                 125

Gly Ala Glu Phe Asp Gln Asp Glu Met Lys Lys Asp Asp Gln Ile Ala
130             135                 140

Ala Ala Ile Ala Leu Arg Gly Met Ala Lys Asp Gly Lys Phe Ala Val
145             150                 155                 160

Lys Gly Asn Asn Glu Lys Glu Lys Ala
                165
```

<210> SEQ ID NO 23
<211> LENGTH: 187
<212> TYPE: PRT
<213> ORGANISM: Borrelia burgdorferi

<400> SEQUENCE: 23

```
Glu Gly Ala Ile Lys Glu Val Ser Glu Leu Leu Asp Lys Leu Val Thr
 1               5                  10                  15

Ala Val Lys Thr Ala Glu Gly Ala Ser Ser Gly Thr Asp Ala Ile Gly
            20                  25                  30

Glu Val Val Asp Asn Asp Ala Lys Val Ala Asp Lys Ala Ser Val Thr
        35                  40                  45

Gly Ile Ala Lys Gly Ile Lys Glu Ile Val Glu Ala Ala Arg Gly Ser
    50                  55                  60

Glu Lys Leu Lys Ala Val Ala Ala Ala Lys Glu Gly Asn Glu Lys Ala
65                  70                  75                  80

Gly Lys Leu Phe Gly Lys Ala Gly Ala Asn Ala His Gly Asp Ser Glu
                85                  90                  95

Ala Ala Ser Lys Ala Gly Ala Val Ser Ala Val Ser Gly Glu Gln
            100                 105                 110

Ile Leu Ser Ala Ile Val Lys Ala Ala Asp Ala Glu Gln Asp Gly
        115                 120                 125

Lys Lys Pro Ala Asp Ala Thr Asn Pro Ile Ala Ala Ile Gly Asn
    130                 135                 140

Lys Asp Glu Asp Ala Asp Phe Gly Asp Gly Met Lys Lys Asp Asp Gln
145                 150                 155                 160

Ile Ala Ala Ala Ile Ala Leu Arg Gly Met Ala Lys Asp Gly Lys Phe
                165                 170                 175

Ala Val Lys Gly Asn Asn Glu Lys Gly Lys Ala
                180                 185
```

<210> SEQ ID NO 24
<211> LENGTH: 169
<212> TYPE: PRT
<213> ORGANISM: Borrelia burgdorferi

<400> SEQUENCE: 24

```
Glu Gly Ala Ser Ser Gly Thr Asp Ala Ile Gly Glu Val Val Asp Asn
 1               5                  10                  15

Asp Ala Lys Ala Ala Asp Lys Ala Ser Val Thr Gly Ile Ala Lys Gly
            20                  25                  30

Ile Lys Glu Ile Val Glu Ala Ala Gly Gly Ser Glu Lys Leu Lys Ala
        35                  40                  45

Val Ala Ala Ala Thr Arg Glu Asn Asn Lys Glu Ala Gly Lys Leu Phe
    50                  55                  60
```

```
Gly Lys Val Asp Asp Ala His Ala Gly Asp Ser Glu Ala Ala Ser Lys
 65                  70                  75                  80

Ala Ala Gly Ala Val Ser Ala Val Ser Gly Glu Gln Ile Leu Ser Ala
                 85                  90                  95

Ile Val Thr Ala Ala Ala Ala Gly Glu Gln Asp Gly Glu Lys Pro Ala
            100                 105                 110

Glu Ala Thr Asn Pro Ile Ala Ala Ile Gly Lys Gly Asn Glu Asp
            115                 120                 125

Gly Ala Asp Phe Gly Lys Asp Glu Met Lys Lys Asp Gln Ile Ala
130                 135                 140

Ala Ala Ile Ala Leu Arg Gly Met Ala Lys Asp Gly Lys Phe Ala Val
145                 150                 155                 160

Lys Ser Asn Asp Gly Lys Gly Lys Ala
                165
```

<210> SEQ ID NO 25
<211> LENGTH: 197
<212> TYPE: PRT
<213> ORGANISM: Borrelia burgdorferi

<400> SEQUENCE: 25

```
Glu Gly Ala Ile Lys Glu Val Ser Glu Leu Leu Asp Lys Leu Val Lys
 1               5                  10                  15

Ala Val Lys Thr Ala Glu Gly Ala Ser Ser Gly Thr Asp Ala Ile Gly
                20                  25                  30

Glu Val Val Ala Asn Ala Gly Ala Ala Lys Ala Ala Asp Lys Ala Ser
            35                  40                  45

Val Thr Gly Ile Ala Lys Gly Ile Lys Glu Ile Val Glu Ala Ala Gly
 50                  55                  60

Gly Ser Lys Lys Leu Lys Ala Ala Ala Glu Gly Glu Asn Asn Lys
 65                  70                  75                  80

Lys Ala Gly Lys Leu Phe Gly Lys Ala Gly Ala Gly Ala Asn
                85                  90                  95

Gly Asp Ser Glu Ala Ala Ser Lys Ala Ala Gly Ala Val Ser Ala Gly
                100                 105                 110

Cys Gly Glu Gln Ile Leu Ser Ala Ile Val Thr Ala Ala Gly Ala Ala
                115                 120                 125

Ala Ser Glu Ala Asp Gln Glu Gly Lys Lys Pro Ala Asp Ala Thr Asn
130                 135                 140

Pro Ile Ala Ala Ala Ile Gly Lys Gly Asp Ala Glu Asn Gly Ala Asp
145                 150                 155                 160

Phe Gly Asp Gly Met Lys Lys Asp Asp Gln Ile Ala Ala Ile Ala
                165                 170                 175

Leu Arg Gly Met Ala Lys Asp Gly Lys Phe Ala Val Lys Asn Asp Asp
                180                 185                 190

Glu Lys Gly Lys Ala
        195
```

<210> SEQ ID NO 26
<211> LENGTH: 189
<212> TYPE: PRT
<213> ORGANISM: Borrelia burgdorferi

<400> SEQUENCE: 26

```
Glu Gly Ala Ile Lys Gly Ala Ser Glu Leu Leu Asp Lys Leu Val Thr
 1               5                  10                  15
```

```
Ala Val Lys Thr Ala Glu Gly Ala Ser Ser Gly Thr Asp Ala Ile Gly
            20                  25                  30

Glu Val Val Ala Asp Ala Ala Lys Ala Ala Asp Lys Asp Ser Val Lys
        35                  40                  45

Gly Ile Ala Lys Gly Ile Lys Glu Ile Val Glu Ala Ala Gly Gly Ser
    50                  55                  60

Glu Lys Leu Lys Val Ala Ala Lys Glu Gly Asn Glu Lys Ala Gly
65                  70                  75                  80

Lys Leu Phe Gly Lys Val Gly Asp Ala Ala His Ala Gly Asp Ser Glu
                85                  90                  95

Ala Ala Ser Lys Ala Gly Ala Val Ser Ala Val Ser Gly Glu Gln
            100                 105                 110

Ile Leu Ser Ala Ile Val Thr Ala Gly Ala Ala Glu Gln Glu Gly
        115                 120                 125

Lys Lys Pro Ala Glu Ala Lys Asn Pro Ile Ala Ala Ile Gly Lys
    130                 135                 140

Gly Asn Glu Asn Gly Ala Glu Phe Lys Asp Glu Met Lys Lys Asp Asp
145                 150                 155                 160

Gln Ile Ala Ala Ala Ile Ala Leu Arg Gly Met Ala Lys Asp Gly Lys
                165                 170                 175

Phe Ala Val Lys Lys Asp Asn Asn Glu Lys Gly Lys Ala
                180                 185
```

<210> SEQ ID NO 27
<211> LENGTH: 190
<212> TYPE: PRT
<213> ORGANISM: Borrelia burgdorferi

<400> SEQUENCE: 27

```
Glu Gly Ala Ile Lys Glu Val Ser Glu Leu Leu Asp Lys Leu Val Thr
1               5                   10                  15

Ala Val Lys Thr Ala Glu Glu Ala Ser Ser Gly Thr Ala Ala Ile Gly
            20                  25                  30

Glu Val Val Ala Asp Asp Ala Ala Ala Lys Ala Ala Asp Lys Glu Ser
        35                  40                  45

Val Lys Gly Ile Ala Lys Gly Ile Lys Glu Ile Val Glu Ala Ala Gly
    50                  55                  60

Gly Ser Lys Lys Leu Lys Val Ala Ala Ala Thr Gly Glu Asn Asn Lys
65                  70                  75                  80

Lys Ala Gly Lys Leu Phe Gly Lys Val Asp Ala Gly Asn Ala Gly Asp
                85                  90                  95

Ser Glu Ala Ala Ser Lys Ala Ala Gly Ala Val Ser Gly Glu Gln Ile
            100                 105                 110

Leu Ser Ala Ile Val Lys Ala Ala Gly Ala Ala Gly Asp Asp Glu
        115                 120                 125

Lys Lys Pro Gly Asp Ala Lys Asn Pro Ile Ala Ala Ile Gly Lys
    130                 135                 140

Gly Asp Ala Glu Asn Gly Ala Glu Phe Asp His Glu Met Lys Lys Asp
145                 150                 155                 160

Asp Gln Ile Ala Ala Ala Ile Ala Leu Arg Gly Met Ala Lys Asp Gly
                165                 170                 175

Lys Phe Ala Val Lys Ser Asp Gly Asp Glu Lys Gly Lys Ala
                180                 185                 190
```

<210> SEQ ID NO 28

```
<211> LENGTH: 194
<212> TYPE: PRT
<213> ORGANISM: Borrelia burgdorferi

<400> SEQUENCE: 28

Glu Gly Ala Ile Lys Gly Ala Ser Glu Leu Leu Asp Lys Leu Val Lys
 1               5                  10                  15

Ala Val Lys Thr Ala Glu Gly Ala Ser Ser Gly Thr Asp Ala Ile Gly
            20                  25                  30

Glu Val Ala Asn Asp Ala Ala Lys Val Ala Asp Lys Glu Ser
        35                  40                  45

Val Thr Gly Ile Ala Lys Gly Ile Lys Glu Ile Val Glu Ala Ala Gly
    50                  55                  60

Gly Ser Glu Lys Leu Lys Val Ala Ala Thr Arg Glu Asn Asn Lys
65                  70                  75                  80

Lys Ala Gly Lys Leu Phe Gly Lys Ala Gly Asp Ala Ala Asn Gly Asp
                85                  90                  95

Ser Glu Ala Ala Ser Lys Ala Ala Gly Ala Val Ser Ala Val Ser Gly
            100                 105                 110

Glu Gln Ile Leu Ser Ala Ile Val Thr Ala Ala Ala Gly Ala Ala
        115                 120                 125

Glu Gln Glu Gly Lys Lys Pro Glu Glu Ala Lys Asn Pro Ile Ala Ala
    130                 135                 140

Ala Ile Gly Lys Gly Asn Ala Asp Asp Gly Ala Glu Phe Asn Lys Glu
145                 150                 155                 160

Gly Met Lys Lys Asp Asp Gln Ile Ala Ala Ile Ala Leu Arg Gly
                165                 170                 175

Met Ala Lys Asp Gly Lys Phe Ala Val Lys Ser Gly Gly Glu Lys Gly
            180                 185                 190

Lys Ala

<210> SEQ ID NO 29
<211> LENGTH: 190
<212> TYPE: PRT
<213> ORGANISM: Borrelia burgdorferi

<400> SEQUENCE: 29

Glu Gly Ala Ile Lys Glu Val Ser Glu Leu Leu Asp Lys Leu Val Thr
 1               5                  10                  15

Thr Val Lys Thr Ala Glu Gly Ala Ser Asn Gly Thr Asp Ala Ile Gly
            20                  25                  30

Lys Val Val Asp Asn Asn Ala Ala Lys Ala Ala Asp Lys Ala Ser
        35                  40                  45

Val Thr Gly Ile Ala Lys Gly Ile Lys Glu Ile Val Glu Ala Ala Gly
    50                  55                  60

Gly Ser Ser Glu Lys Leu Lys Ala Val Ala Ala Lys Gly Glu Ser
65                  70                  75                  80

Asn Glu Lys Ala Gly Lys Leu Phe Gly Lys Ala Gly Ala Ala Ala Gly
                85                  90                  95

Asp Ser Glu Ala Ala Ser Lys Ala Ala Gly Ala Val Ser Ala Val Ser
            100                 105                 110

Gly Glu Gln Ile Leu Ser Ala Ile Val Lys Ala Ala Gly Ala Ala Asp
        115                 120                 125

Gln Glu Gly Lys Lys Pro Glu Glu Asp Lys Asn Pro Ile Ala Ala Ala
    130                 135                 140
```

```
Ile Gly Asp Lys Asp Gly Gly Ala Glu Phe Asn His Glu Met Lys Lys
145                 150                 155                 160

Asp Asp Gln Ile Ala Ala Ile Ala Leu Arg Gly Met Ala Lys Asp
            165                 170                 175

Gly Lys Phe Ala Val Lys Ser Gly Gly Glu Lys Glu Lys Ala
        180                 185                 190
```

<210> SEQ ID NO 30
<211> LENGTH: 157
<212> TYPE: PRT
<213> ORGANISM: Borrelia burgdorferi

<400> SEQUENCE: 30

```
Glu Gly Ala Ile Lys Glu Val Ser Glu Leu Leu Asp Lys Leu Val Lys
1               5                   10                  15

Ala Val Lys Thr Ala Glu Gly Ala Ser Ser Gly Thr Asp Ala Ile Gly
            20                  25                  30

Glu Val Val Ala Asp Asn Ser Ala Ala Lys Ala Ala Asp Glu Ala Ser
        35                  40                  45

Val Thr Gly Ile Ala Lys Gly Ile Lys Glu Ile Val Glu Ala Ala Gly
    50                  55                  60

Gly Ser Glu Lys Leu Lys Val Ala Ala Ala Gly Glu Asn Asn Lys
65                  70                  75                  80

Lys Ala Gly Lys Leu Phe Gly Lys Val Asp Asn Ala Asn Ala Gly Asp
                85                  90                  95

Ser Glu Ala Ala Ser Lys Ala Ala Gly Ala Val Ser Gly Glu Gln Ile
            100                 105                 110

Leu Ser Ala Ile Val Lys Ala Ala Gly Glu Ala Glu Gln Asp Gly Glu
        115                 120                 125

Lys Pro Gly Glu Ala Thr Lys Gly Asp Glu Asp Ala Asp Phe Gly Asn
    130                 135                 140

Glu Met Lys Lys Asp Gly Lys Phe Ala Ile Leu Thr Phe
145                 150                 155
```

<210> SEQ ID NO 31
<211> LENGTH: 212
<212> TYPE: PRT
<213> ORGANISM: Borrelia burgdorferi

<400> SEQUENCE: 31

```
Ser Thr Thr Gly Lys Pro Asp Ser Thr Gly Ser Val Gly Thr Ala Val
1               5                   10                  15

Glu Gly Ala Ile Lys Glu Val Ser Glu Leu Leu Asp Lys Leu Val Lys
            20                  25                  30

Ala Val Lys Thr Ala Glu Gly Ala Ser Ser Gly Thr Ala Ala Ile Gly
        35                  40                  45

Glu Val Val Ala Asp Ala Asp Ala Ala Lys Val Ala Asp Lys Ala Ser
    50                  55                  60

Val Lys Gly Ile Ala Lys Gly Ile Lys Glu Ile Val Glu Ala Ala Gly
65                  70                  75                  80

Gly Ser Glu Lys Leu Lys Ala Val Ala Ala Ala Lys Gly Glu Asn Asn
                85                  90                  95

Lys Gly Ala Gly Lys Leu Phe Gly Lys Ala Gly Ala Ala Ala His Gly
            100                 105                 110

Asp Ser Glu Ala Ala Ser Lys Ala Ala Gly Ala Val Ser Ala Val Ser
        115                 120                 125
```

-continued

Gly Glu Gln Ile Leu Ser Ala Ile Val Thr Ala Ala Asp Ala Ala Glu
            130                 135                 140

Gln Asp Gly Lys Lys Pro Glu Ala Lys Asn Pro Ile Ala Ala Ala
145                 150                 155                 160

Ile Gly Asp Lys Asp Gly Gly Ala Glu Phe Gly Gln Asp Glu Met Lys
                    165                 170                 175

Lys Asp Asp Gln Ile Ala Ala Ala Ile Ala Leu Arg Gly Met Ala Lys
                180                 185                 190

Asp Gly Lys Phe Ala Val Lys Asp Gly Glu Lys Glu Lys Ala Glu Gly
                195                 200                 205

Ala Ile Lys Gly
        210

<210> SEQ ID NO 32
<211> LENGTH: 212
<212> TYPE: PRT
<213> ORGANISM: Borrelia burgdorferi

<400> SEQUENCE: 32

Ser Thr Thr Gly Lys Pro Asp Ser Thr Gly Ser Val Gly Thr Ala Val
1               5                   10                  15

Glu Gly Ala Ile Lys Glu Val Ser Glu Leu Leu Asp Lys Leu Val Lys
            20                  25                  30

Ala Val Lys Thr Ala Glu Gly Ala Ser Ser Gly Thr Asp Ala Ile Gly
        35                  40                  45

Glu Val Val Ala Asn Ala Gly Ala Ala Lys Val Ala Asp Lys Ala Ser
    50                  55                  60

Val Thr Gly Ile Ala Lys Gly Ile Lys Glu Ile Val Glu Ala Ala Gly
65                  70                  75                  80

Gly Ser Glu Lys Leu Lys Val Ala Ala Thr Gly Glu Ser Asn Lys
            85                  90                  95

Gly Ala Gly Lys Leu Phe Gly Lys Val Asp Ala His Ala Gly Asp
                100                 105                 110

Ser Glu Ala Ala Ser Lys Ala Ala Gly Ala Val Ser Ala Val Ser Gly
            115                 120                 125

Glu Gln Ile Leu Ser Ala Ile Val Thr Ala Ala Ala Gly Glu Gln
            130                 135                 140

Asp Gly Glu Lys Pro Glu Gly Asp Lys Asn Pro Ile Ala Ala Ile
145                 150                 155                 160

Gly Lys Gly Asp Ala Asp Gly Ala Asp Phe Gly Asp Gly Met Lys
                    165                 170                 175

Lys Asp Asp Gln Ile Ala Ala Ile Ala Leu Arg Gly Met Ala Lys
                180                 185                 190

Asp Gly Lys Phe Ala Val Lys Asn Asp Glu Lys Gly Lys Ala Glu Gly
                195                 200                 205

Ala Ile Lys Gly
        210

<210> SEQ ID NO 33
<211> LENGTH: 209
<212> TYPE: PRT
<213> ORGANISM: Borrelia burgdorferi

<400> SEQUENCE: 33

Ser Thr Thr Gly Lys Pro Asp Ser Thr Gly Ser Val Gly Thr Ala Val
1               5                   10                  15

Glu Gly Ala Ile Lys Glu Val Ser Glu Leu Leu Asp Lys Leu Val Lys
                20                  25                  30

Ala Val Lys Thr Ala Glu Gly Ala Ser Ser Gly Thr Asp Ala Ile Gly
            35                  40                  45

Glu Val Val Asp Asn Ala Ala Lys Ala Ala Asp Lys Ala Ser Val Thr
        50                  55                  60

Gly Ile Ala Lys Gly Ile Lys Glu Ile Val Glu Ala Ala Gly Gly Ser
65                  70                  75                  80

Glu Lys Leu Lys Val Ala Ala Ala Thr Gly Glu Ser Asn Lys Gly Ala
                85                  90                  95

Gly Lys Leu Phe Gly Lys Ala Gly Ala Gly Ala Asn Gly Asp Ser Glu
            100                 105                 110

Ala Ala Ser Lys Ala Ala Gly Ala Val Ser Ala Val Ser Gly Glu Gln
        115                 120                 125

Ile Leu Ser Ala Ile Val Lys Ala Ala Gly Ala Ala Asp Gln Asp Gly
    130                 135                 140

Glu Lys Pro Gly Asp Ala Lys Asn Pro Ile Ala Ala Ile Gly Lys
145                 150                 155                 160

Gly Asp Gly Asp Ala Glu Phe Asp Gln Asp Glu Met Lys Lys Asp Asp
                165                 170                 175

Gln Ile Ala Ala Ile Ala Leu Arg Gly Met Ala Lys Asp Gly Lys
            180                 185                 190

Phe Ala Val Lys Asn Asp Gl

```
Lys Lys Asp Asp Gln Ile Ala Ala Ile Ala Leu Arg Gly Met Ala
            180                 185                 190

Lys Asp Gly Lys Phe Ala Val Lys Asp Asp Glu Lys Glu Lys Ala
        195                 200                 205

Glu Gly Ala Ile Lys Gly
    210

<210> SEQ ID NO 35
<211> LENGTH: 214
<212> TYPE: PRT
<213> ORGANISM: Borrelia burgdorferi

<400> SEQUENCE: 35

Ser Thr Thr Gly Lys Pro Asp Ser Thr Gly Ser Val Gly Thr Ala Val
  1               5                  10                  15

Glu Gly Ala Ile Lys Glu Val Ser Glu Leu Leu Asp Lys Leu Val Lys
                 20                  25                  30

Ala Val Lys Thr Ala Glu Gly Ala Ser Ser Gly Thr Asp Ala Ile Gly
             35                  40                  45

Glu Val Val Ala Asp Asp Asn Ala Ala Lys Val Ala Asp Lys Ala Ser
 50                  55                  60

Val Thr Gly Ile Ala Lys Gly Ile Lys Glu Ile Val Glu Ala Ala Gly
 65                  70                  75                  80

Gly Ser Glu Lys Leu Lys Val Ala Ala Thr Gly Glu Ser Asn Lys
                 85                  90                  95

Gly Ala Gly Lys Leu Phe Gly Lys Val Gly Ala His Ala Gly Asp Ser
                100                 105                 110

Glu Ala Ala Ser Lys Ala Ala Gly Ala Val Ser Ala Val Ser Gly Glu
            115                 120                 125

Gln Ile Leu Ser Ala Ile Val Lys Ala Gly Ala Ala Glu Gln Glu
        130                 135                 140

Gly Lys Lys Pro Glu Glu Ala Lys Asn Pro Ile Ala Ala Ile Gly
145                 150                 155                 160

Lys Gly Asp Ala Glu Asn Gly Ala Glu Phe Asn His Asp Gly Met Lys
                165                 170                 175

Lys Asp Asp Gln Ile Ala Ala Ile Ala Leu Arg Gly Met Ala Lys
            180                 185                 190

Asp Gly Lys Phe Ala Val Lys Ser Gly Gly Glu Lys Gly Lys Ala
        195                 200                 205

Glu Gly Ala Ile Lys Gly
    210

<210> SEQ ID NO 36
<211> LENGTH: 215
<212> TYPE: PRT
<213> ORGANISM: Borrelia burgdorferi

<400> SEQUENCE: 36

Ser Thr Thr Gly Lys Pro Asp Ser Thr Gly Ser Val Gly Thr Ala Val
  1               5                  10                  15

Glu Gly Ala Ile Lys Glu Val Ser Glu Leu Leu Asp Lys Leu Val Thr
                 20                  25                  30

Ala Val Lys Thr Ala Glu Gly Ala Ser Ser Gly Thr Asp Ala Ile Gly
             35                  40                  45

Glu Val Val Asp Asn Asp Ala Ala Lys Ala Ala Asp Lys Glu Ser
 50                  55                  60
```

```
Val Thr Gly Ile Ala Lys Gly Ile Lys Glu Ile Val Glu Ala Ala Arg
 65                  70                  75                  80

Gly Ser Glu Lys Leu Lys Ala Val Ala Ala Lys Glu Gly Asn Glu
             85                  90                  95

Lys Ala Gly Lys Leu Phe Gly Lys Ala Gly Ala Ala Gly Asp Ser
            100                 105                 110

Glu Ala Ala Ser Lys Ala Ala Gly Ala Val Ser Ala Val Ser Gly Glu
            115                 120                 125

Gln Ile Leu Ser Ala Ile Val Lys Ala Ala Ala Ala Gly Asp
130                 135                 140

Gln Glu Gly Lys Lys Pro Gly Asp Ala Lys Asn Pro Ile Ala Ala
145                 150                 155                 160

Ile Gly Lys Gly Asp Ala Asp Gly Ala Glu Phe Asp His Glu Met
                165                 170                 175

Lys Lys Asp Asp Gln Ile Ala Ala Ala Ile Ala Leu Arg Gly Met Ala
            180                 185                 190

Lys Asp Gly Lys Phe Ala Val Lys Ser Gly Gly Glu Lys Glu Lys
                195                 200                 205

Ala Glu Gly Ala Ile Lys Gly
210                 215

<210> SEQ ID NO 37
<211> LENGTH: 211
<212> TYPE: PRT
<213> ORGANISM: Borrelia burgdorferi

<400> SEQUENCE: 37

Ser Thr Thr Gly Lys Pro Asp Ser Thr Gly Ser Val Gly Thr Ala Val
  1               5                  10                  15

Glu Gly Ala Ile Lys Glu Val Ser Gly Ala Ala Asp Lys Leu Val Lys
             20                  25                  30

Ala Val Lys Thr Ala Glu Gly Ala Ser Ser Gly Thr Ala Ala Ile Gly
             35                  40                  45

Glu Val Val Asp Asn Asn Ala Ala Lys Ala Ala Asp Lys Ala Ser
 50                  55                  60

Val Thr Gly Ile Ala Lys Gly Ile Lys Glu Ile Val Glu Ala Ala Gly
 65                  70                  75                  80

Gly Ser Glu Lys Leu Lys Val Ala Ala Thr Gly Glu Ser Asn Lys
             85                  90                  95

Gly Ala Gly Lys Leu Phe Gly Lys Ala Gly Ala Asp Ala His Gly Asp
            100                 105                 110

Ser Glu Ala Ala Ser Lys Ala Ala Gly Ala Val Ser Ala Val Ser Gly
            115                 120                 125

Glu Gln Ile Leu Ser Ala Ile Val Lys Ala Ala Asp Ala Ala Asp Gln
130                 135                 140

Asp Gly Glu Lys Pro Gly Asp Ala Lys Asn Pro Ile Ala Ala Ile
145                 150                 155                 160

Gly Lys Gly Asp Gly Ala Glu Phe Ser Gln Asp Glu Met Lys Lys
                165                 170                 175

Asp Asp Gln Ile Ala Ala Ala Ile Ala Leu Arg Gly Met Ala Lys Asp
            180                 185                 190

Gly Lys Phe Ala Val Lys Asn Asn Glu Lys Gly Lys Ala Glu Gly Ala
                195                 200                 205

Ile Lys Gly
210
```

<210> SEQ ID NO 38
<211> LENGTH: 216
<212> TYPE: PRT
<213> ORGANISM: Borrelia burgdorferi

<400> SEQUENCE: 38

Ser Thr Thr Gly Lys Pro Asp Ser Thr Gly Ser Val Gly Thr Ala Val
1               5                   10                  15

Glu Gly Ala Ile Lys Glu Val Ser Glu Leu Leu Asp Lys Leu Val Lys
            20                  25                  30

Ala Val Lys Thr Ala Glu Glu Ala Ser Ser Gly Thr Asp Ala Ile Gly
        35                  40                  45

Glu Val Val Asp Asn Ala Ala Ala Lys Ala Ala Asp Lys Ala Ser
    50                  55                  60

Val Thr Gly Ile Ala Lys Gly Ile Lys Glu Ile Val Glu Ala Ala Gly
65                  70                  75                  80

Gly Ser Glu Lys Leu Lys Ala Ala Ala Thr Gly Glu Asn Asn
                85                  90                  95

Lys Glu Ala Gly Lys Leu Phe Gly Lys Val Asp Ala Gly Asn Ala Gly
                100                 105                 110

Asp Ser Glu Ala Ala Ser Lys Ala Ala Gly Ala Val Ser Ala Val Ser
            115                 120                 125

Gly Glu Gln Ile Leu Ser Ala Ile Val Lys Ala Ala Gly Glu Ala Ala
        130                 135                 140

Gly Asp Gln Glu Gly Lys Lys Pro Gly Glu Ala Lys Asn Pro Ile Ala
145                 150                 155                 160

Ala Ala Ile Gly Lys Gly Asn Ala Asp Asp Gly Ala Glu Phe Gly Asp
                165                 170                 175

Gly Met Lys Lys Asp Asp Gln Ile Ala Ala Ala Ile Ala Leu Arg Gly
                180                 185                 190

Met Ala Lys Asp Gly Lys Phe Ala Val Lys Ser Gly Gly Glu Lys Glu
                195                 200                 205

Lys Ala Glu Gly Ala Ile Lys Gly
        210                 215

<210> SEQ ID NO 39
<211> LENGTH: 213
<212> TYPE: PRT
<213> ORGANISM: Borrelia burgdorferi

<400> SEQUENCE: 39

Ser Thr Thr Gly Lys Pro Asp Ser Thr Gly Ser Val Gly Thr Ala Val
1               5                   10                  15

Glu Gly Ala Ile Lys Glu Val Ser Glu Leu Leu Asp Lys Leu Val Lys
            20                  25                  30

Ala Val Lys Thr Ala Glu Gly Ala Ser Ser Gly Thr Asp Ala Ile Gly
        35                  40                  45

Glu Val Val Ala Asn Ala Gly Ala Ala Lys Val Ala Asp Lys Ala Ser
    50                  55                  60

Val Thr Gly Ile Ala Lys Gly Ile Lys Glu Ile Val Glu Ala Ala Gly
65                  70                  75                  80

Gly Ser Glu Lys Leu Lys Val Ala Ala Ala Thr Gly Glu Ser Asn Lys
                85                  90                  95

Gly Ala Gly Lys Leu Phe Gly Lys Val Asp Asp Ala His Ala Gly Asp
                100                 105                 110

```
Ser Glu Ala Ala Ser Lys Ala Gly Ala Val Ser Ala Val Ser Gly
        115                 120                 125

Glu Gln Ile Leu Ser Ala Ile Val Lys Ala Ala Asp Ala Ala Glu Gln
        130                 135                 140

Asp Gly Lys Lys Pro Glu Glu Ala Thr Asn Pro Ile Ala Ala Ala Ile
145                 150                 155                 160

Gly Glu Gly Asn Glu Asp Gly Ala Asp Phe Gly Lys Asp Glu Met Lys
                165                 170                 175

Lys Asp Asp Gln Ile Ala Ala Ile Ala Leu Arg Gly Met Ala Lys
                180                 185                 190

Asp Gly Lys Phe Ala Val Lys Asp Gly Gly Lys Gly Lys Ala Glu
        195                 200                 205

Gly Ala Ile Lys Gly
        210
```

<210> SEQ ID NO 40
<211> LENGTH: 211
<212> TYPE: PRT
<213> ORGANISM: Borrelia burgdorferi

<400> SEQUENCE: 40

```
Ser Thr Thr Gly Lys Pro Asp Ser Thr Gly Ser Val Gly Thr Ala Val
1               5                   10                  15

Glu Gly Ala Ile Lys Glu Val Ser Glu Leu Leu Asp Lys Leu Val Lys
                20                  25                  30

Ala Val Lys Thr Ala Glu Gly Ala Ser Ser Gly Thr Ala Ala Ile Gly
            35                  40                  45

Glu Val Val Asp Asn Asp Ala Lys Ala Asp Lys Ala Ser Val Thr
    50                  55                  60

Gly Ile Ala Lys Gly Ile Lys Glu Ile Val Glu Ala Ala Gly Gly Ser
65                  70                  75                  80

Glu Lys Leu Lys Ala Val Ala Ala Lys Gly Glu Asn Asn Lys Gly
                85                  90                  95

Ala Gly Lys Leu Phe Gly Lys Val Asp Asp Ala His Ala Gly Asp Ser
            100                 105                 110

Glu Ala Ala Ser Lys Ala Ala Gly Ala Val Ser Ala Val Ser Gly Glu
        115                 120                 125

Gln Ile Leu Ser Ala Ile Val Thr Ala Ala Asp Ala Ala Glu Gln Asp
        130                 135                 140

Gly Glu Lys Pro Glu Glu Ala Lys Asn Pro Ile Ala Ala Ala Ile Gly
145                 150                 155                 160

Lys Gly Asn Glu Asp Gly Ala Glu Phe Gly Lys Asp Glu Met Lys Lys
                165                 170                 175

Asp Asp Gln Ile Ala Ala Ile Ala Leu Arg Gly Met Ala Lys Asp
                180                 185                 190

Gly Lys Phe Ala Val Lys Asp Gly Glu Lys Glu Lys Ala Glu Gly Ala
        195                 200                 205

Ile Lys Gly
    210
```

<210> SEQ ID NO 41
<211> LENGTH: 212
<212> TYPE: PRT
<213> ORGANISM: Borrelia burgdorferi

<400> SEQUENCE: 41

-continued

```
Ser Thr Thr Gly Lys Pro Asp Ser Thr Gly Ser Val Gly Thr Ala Val
  1               5                  10

```
                145                 150                 155                 160
Asn Lys Asp Gly Gly Ala Asp Phe Gly Asp Gly Met Lys Lys Asp Asp
                    165                 170                 175

Gln Ile Ala Ala Ala Ile Ala Leu Arg Gly Met Ala Lys Asp Gly Lys
            180                 185                 190

Phe Ala Val Lys Glu Asp Glu Lys Glu Lys Ala Glu Gly Ala Ile Lys
        195                 200                 205

Gly

<210> SEQ ID NO 43
<211> LENGTH: 212
<212> TYPE: PRT
<213> ORGANISM: Borrelia burgdorferi

<400> SEQUENCE: 43

Ser Thr Thr Gly Lys Pro Asp Ser Thr Gly Ser Val Gly Thr Ala Val
  1               5                  10                  15

Glu Gly Ala Ile Lys Glu Val Ser Glu Leu Leu Asp Lys Leu Val Lys
             20                  25                  30

Ala Val Lys Thr Ala Glu Gly Ala Ser Ser Gly Thr Ala Ala Ile Gly
         35                  40                  45

Glu Val Val Ala Asp Ala Asp Ala Ala Lys Val Ala Asp Lys Ala Ser
 50                  55                  60

Val Lys Gly Ile Ala Lys Gly Ile Lys Glu Ile Val Glu Ala Ala Gly
 65                  70                  75                  80

Gly Ser Glu Lys Leu Lys Ala Val Ala Ala Ala Lys Gly Glu Asn Asn
                 85                  90                  95

Lys Gly Ala Gly Lys Leu Phe Gly Lys Ala Gly Ala Ala Ala His Gly
            100                 105                 110

Asp Ser Glu Ala Ala Ser Lys Ala Ala Gly Ala Val Ser Ala Val Ser
        115                 120                 125

Gly Glu Gln Ile Leu Ser Ala Ile Val Thr Ala Ala Asp Ala Ala Glu
    130                 135                 140

Gln Asp Gly Lys Lys Pro Glu Glu Ala Lys Asn Pro Ile Ala Ala Ala
145                 150                 155                 160

Ile Gly Asp Lys Asp Gly Gly Ala Glu Phe Gly Gln Asp Glu Met Lys
                165                 170                 175

Lys Asp Asp Gln Ile Ala Ala Ile Ala Leu Arg Gly Met Ala Lys
            180                 185                 190

Asp Gly Lys Phe Ala Val Lys Asp Gly Glu Lys Glu Lys Ala Glu Gly
        195                 200                 205

Ala Ile Lys Gly
    210

<210> SEQ ID NO 44
<211> LENGTH: 212
<212> TYPE: PRT
<213> ORGANISM: Borrelia burgdorferi

<400> SEQUENCE: 44

Ser Thr Thr Gly Lys Pro Asp Ser Thr Gly Ser Val Gly Thr Ala Val
  1               5                  10                  15

Glu Gly Ala Ile Lys Glu Val Ser Glu Leu Leu Asp Lys Leu Val Lys
             20                  25                  30

Ala Val Lys Thr Ala Glu Gly Ala Ser Ser Gly Thr Asp Ala Ile Gly
         35                  40                  45
```

```
Glu Val Val Ala Asn Ala Gly Ala Ala Lys Val Ala Asp Lys Ala Ser
 50                  55                  60

Val Thr Gly Ile Ala Lys Gly Ile Lys Glu Ile Val Glu Ala Ala Gly
 65                  70                  75                  80

Gly Ser Glu Lys Leu Lys Ala Val Ala Ala Lys Thr Glu Asn Ser Lys
                 85                  90                  95

Gly Ala Gly Lys Leu Phe Gly Lys Val Asp Asp Ala His Ala Gly Asp
                100                 105                 110

Ser Glu Ala Ala Ser Lys Ala Ala Gly Ala Val Ser Ala Val Ser Gly
                115                 120                 125

Glu Gln Ile Leu Ser Ala Ile Val Thr Ala Ala Ala Gly Glu Gln
130                 135                 140

Asp Gly Glu Lys Pro Gly Asp Ala Lys Asn Pro Ile Ala Ala Ala Ile
145                 150                 155                 160

Gly Lys Gly Asp Ala Asp Asp Gly Ala Asp Phe Gly As 195             200             205

Gly

<210> SEQ ID NO 46
<211> LENGTH: 216
<212> TYPE: PRT
<213> ORGANISM: Borrelia burgdorferi

<400> SEQUENCE: 46

Ser Thr Thr Gly Lys Pro Asp Ser Thr Gly Ser Val Gly Thr Ala Val
  1               5                  10                  15

Glu Gly Ala Ile Lys Glu Val Ser Glu Leu Leu Asp Lys Leu Val Lys
             20                  25                  30

Ala Val Lys Thr Ala Glu Gly Ala Ser Ser Gly Thr Ala Ala Ile Gly
         35                  40                  45

Glu Val Val Ala Asp Ala Ala Lys Ala Ala Asp Lys Asp Ser Val Lys
     50                  55                  60

Gly Ile Ala Lys Gly Ile Lys Glu Ile Val Glu Ala Ala Gly Gly Ser
 65                  70                  75                  80

Glu Lys Leu Lys Ala Val Ala Ala Ala Lys Thr Glu Asn Ser Lys Gly
                 85                  90                  95

Ala Gly Lys Leu Phe Gly Lys Val Asp Gly Ala Ala His Gly Asp Ser
            100                 105                 110

Glu Ala Ala Ser Lys Ala Ala Gly Ala Val Ser Ala Val Ser Gly Glu
        115                 120                 125

Gln Ile Leu Ser Ala Ile Val Thr Ala Ala Gly Ala Ala Ala Ser Glu
    130                 135                 140

Ala Asp Gln Glu Gly Lys Lys Pro Ala Asp Ala Thr Asn Pro Ile Ala
145                 150                 155                 160

Ala Ala Ile Gly Lys Gly Asn Glu Glu Asn Gly Ala Glu Phe Gly Asp
                165                 170                 175

Gly Met Lys Lys Asp Asp Gln Ile Ala Ala Ile Ala Leu Arg Gly
            180                 185                 190

Met Ala Lys Asp Gly Lys Phe Ala Val Lys Asn Asp Asp Glu Lys Gly
        195                 200                 205

Lys Ala Glu Gly Ala Ile Lys Gly
    210                 215

<210> SEQ ID NO 47
<211> LENGTH: 208
<212> TYPE: PRT
<213> ORGANISM: Borrelia burgdorferi

<400> SEQUENCE: 47

Ser Thr Thr Gly Lys Pro Asp Ser Thr Gly Ser Val Gly Thr Ala Val
  1               5                  10                  15

Glu Gly Ala Ile Lys Glu Val Ser Glu Leu Leu Asp Lys Leu Val Thr
             20                  25                  30

Ala Val Lys Thr Ala Glu Gly Ala Ser Ser Gly Thr Asp Ala Ile Gly
         35                  40                  45

Glu Val Val Asp Asn Asp Ala Lys Ala Ala Asp Lys Ala Ser Val Thr
     50                  55                  60

Gly Ile Ala Lys Gly Ile Lys Glu Ile Val Glu Ala Ala Gly Gly Ser
 65                  70                  75                  80

Glu Lys Leu Lys Ala Ala Ala Ala Lys Gly Glu Asn Ser Lys Gly Ala
                 85                  90                  95

```
Gly Lys Leu Phe Gly Lys Ala Gly Ala Asp Ala Asn Gly Asp Ser Glu
                100                 105                 110
Ala Ala Ser Lys Ala Ala Gly Ala Val Ser Ala Val Ser Gly Glu Gln
            115                 120                 125
Ile Leu Ser Ala Ile Val Thr Ala Ala Asp Ala Ala Glu Gln Asp Gly
        130                 135                 140
Glu Lys Pro Gly Asp Ala Lys Asn Pro Ile Ala Ala Ile Gly Lys
145                 150                 155                 160
Gly Asp Gly Asp Ala Asp Phe Gly Asp Gly Met Lys Lys Asp Asp Gln
                165                 170                 175
Ile Ala Ala Ala Ile Ala Leu Arg Gly Met Ala Lys Asp Gly Lys Phe
            180                 185                 190
Ala Val Lys Asn Asp Glu Lys Gly Lys Ala Glu Gly Ala Ile Lys Gly
        195                 200                 205
```

<210> SEQ ID NO 48
<211> LENGTH: 212
<212> TYPE: PRT
<213> ORGANISM: Borrelia burgdorferi
<400> SEQUENCE: 48

```
Ser Thr Thr Gly Lys Pro Asp Ser Thr Gly Ser Val Gly Thr Ala Val
 1               5                  10                  15
Glu Gly Ala Ile Lys Glu Val Ser Glu Leu Leu Asp Lys Leu Val Lys
            20                  25                  30
Ala Val Lys Thr Ala Glu Gly Ala Ser Ser Gly Thr Ala Ala Ile Gly
        35                  40                  45
Glu Val Val Asp Asn Ala Ala Lys Ala Ala Asp Lys Ala Ser Val Thr
    50                  55                  60
Gly Ile Ala Lys Gly Ile Lys Glu Ile Val Glu Ala Ala Gly Gly Ser
65                  70                  75                  80
Glu Lys Leu Lys Ala Val Ala Ala Ala Lys Thr Glu Asn Ser Lys Gly
                85                  90                  95
Ala Gly Lys Leu Phe Gly Lys Ala Gly Ala Asp Ala Asn Ala Gly Asp
                100                 105                 110
Ser Glu Ala Ala Ser Lys Ala Ala Gly Ala Val Ser Ala Val Ser Gly
            115                 120                 125
Glu Gln Ile Leu Ser Ala Ile Val Thr Ala Ala Asp Ala Ala Glu Gln
        130                 135                 140
Glu Gly Lys Lys Pro Glu Glu Ala Lys Asn Pro Ile Ala Ala Ala Ile
145                 150                 155                 160
Gly Lys Gly Asn Ala Asp Asp Gly Ala Asp Phe Gly Gln Asp Met Lys
                165                 170                 175
Lys Asp Asp Gln Ile Ala Ala Ile Ala Leu Arg Gly Met Ala Lys
            180                 185                 190
Asp Gly Lys Phe Ala Val Lys Lys Asp Glu Lys Gly Lys Ala Glu Gly
        195                 200                 205
Ala Ile Lys Gly
    210
```

<210> SEQ ID NO 49
<211> LENGTH: 1141
<212> TYPE: DNA
<213> ORGANISM: Borrelia hermsii
<220> FEATURE:
<221> NAME/KEY: CDS

<222> LOCATION: (1)..(1062)

<400> SEQUENCE: 49

| | | | | | | | | | | | | | | | | |
|---|---|---|---|---|---|---|---|---|---|---|---|---|---|---|---|---|
| atg | aga | aaa | aga | ata | agt | gca | ata | ata | atg | act | tta | ttt | atg | gta | tta | 48 |
| Met | Arg | Lys | Arg | Ile | Ser | Ala | Ile | Ile | Met | Thr | Leu | Phe | Met | Val | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gta | agc | tgt | aat | agc | ggt | ggg | gtt | gcg | gaa | gat | cct | aaa | act | gtg | tat | 96 |
| Val | Ser | Cys | Asn | Ser | Gly | Gly | Val | Ala | Glu | Asp | Pro | Lys | Thr | Val | Tyr | |
| | | | 20 | | | | | 25 | | | | | 30 | | | |

| | | | | | | | | | | | | | | | | |
|---|---|---|---|---|---|---|---|---|---|---|---|---|---|---|---|---|
| tta | aca | tct | ata | gct | aat | tta | ggg | aaa | gga | ttt | tta | gat | gtt | ttt | gtg | 144 |
| Leu | Thr | Ser | Ile | Ala | Asn | Leu | Gly | Lys | Gly | Phe | Leu | Asp | Val | Phe | Val | |
| | | 35 | | | | | 40 | | | | | 45 | | | | |

| | | | | | | | | | | | | | | | | |
|---|---|---|---|---|---|---|---|---|---|---|---|---|---|---|---|---|
| act | ttt | gga | gat | atg | gtt | act | gga | gct | ttt | ggt | att | aag | gca | gat | act | 192 |
| Thr | Phe | Gly | Asp | Met | Val | Thr | Gly | Ala | Phe | Gly | Ile | Lys | Ala | Asp | Thr | |
| | 50 | | | | | 55 | | | | | 60 | | | | | |

| | | | | | | | | | | | | | | | | |
|---|---|---|---|---|---|---|---|---|---|---|---|---|---|---|---|---|
| aag | aaa | agt | gat | ata | ggg | aag | tat | ttt | act | gat | att | gag | agc | act | atg | 240 |
| Lys | Lys | Ser | Asp | Ile | Gly | Lys | Tyr | Phe | Thr | Asp | Ile | Glu | Ser | Thr | Met | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| aca | tca | gtt | aaa | aag | aag | ttg | caa | gat | gaa | gtt | gct | aag | aat | ggt | aac | 288 |
| Thr | Ser | Val | Lys | Lys | Lys | Leu | Gln | Asp | Glu | Val | Ala | Lys | Asn | Gly | Asn | |
| | | | | 85 | | | | | 90 | | | | | 95 | | |

| | | | | | | | | | | | | | | | | |
|---|---|---|---|---|---|---|---|---|---|---|---|---|---|---|---|---|
| tat | cca | aag | gta | aag | aca | gct | gtt | gac | gaa | ttt | gtt | gca | atc | tta | gga | 336 |
| Tyr | Pro | Lys | Val | Lys | Thr | Ala | Val | Asp | Glu | Phe | Val | Ala | Ile | Leu | Gly | |
| | | | 100 | | | | | 105 | | | | | 110 | | | |

| | | | | | | | | | | | | | | | | |
|---|---|---|---|---|---|---|---|---|---|---|---|---|---|---|---|---|
| aag | atc | gag | aaa | gga | gca | aaa | gaa | gca | tct | aaa | ggg | gct | act | ggt | gat | 384 |
| Lys | Ile | Glu | Lys | Gly | Ala | Lys | Glu | Ala | Ser | Lys | Gly | Ala | Thr | Gly | Asp | |
| | | 115 | | | | | 120 | | | | | 125 | | | | |

| | | | | | | | | | | | | | | | | |
|---|---|---|---|---|---|---|---|---|---|---|---|---|---|---|---|---|
| gtt | att | att | ggg | aat | act | gtt | aag | aat | ggt | gat | gct | gta | cct | gga | gaa | 432 |
| Val | Ile | Ile | Gly | Asn | Thr | Val | Lys | Asn | Gly | Asp | Ala | Val | Pro | Gly | Glu | |
| | 130 | | | | | 135 | | | | | 140 | | | | | |

| | | | | | | | | | | | | | | | | |
|---|---|---|---|---|---|---|---|---|---|---|---|---|---|---|---|---|
| gca | aca | agt | gtc | aat | tct | ctt | gtt | aaa | gga | att | aaa | gaa | ata | gtt | ggg | 480 |
| Ala | Thr | Ser | Val | Asn | Ser | Leu | Val | Lys | Gly | Ile | Lys | Glu | Ile | Val | Gly | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gta | gtc | ttg | aag | gaa | ggt | aag | gca | gat | gct | gat | gct | act | aaa | gat | gat | 528 |
| Val | Val | Leu | Lys | Glu | Gly | Lys | Ala | Asp | Ala | Asp | Ala | Thr | Lys | Asp | Asp | |
| | | | | 165 | | | | | 170 | | | | | 175 | | |

| | | | | | | | | | | | | | | | | |
|---|---|---|---|---|---|---|---|---|---|---|---|---|---|---|---|---|
| agt | aag | aaa | gat | att | ggt | aaa | tta | ttt | acc | gca | acc | act | gat | gcg | aat | 576 |
| Ser | Lys | Lys | Asp | Ile | Gly | Lys | Leu | Phe | Thr | Ala | Thr | Thr | Asp | Ala | Asn | |
| | | | 180 | | | | | 185 | | | | | 190 | | | |

| | | | | | | | | | | | | | | | | |
|---|---|---|---|---|---|---|---|---|---|---|---|---|---|---|---|---|
| aga | gct | gat | aat | gcg | gca | gct | caa | gca | gct | gca | gcg | tca | ata | gga | gca | 624 |
| Arg | Ala | Asp | Asn | Ala | Ala | Ala | Gln | Ala | Ala | Ala | Ala | Ser | Ile | Gly | Ala | |
| | | 195 | | | | | 200 | | | | | 205 | | | | |

| | | | | | | | | | | | | | | | | |
|---|---|---|---|---|---|---|---|---|---|---|---|---|---|---|---|---|
| gtg | aca | ggt | gct | gat | atc | ttg | caa | gct | ata | gta | caa | tct | aag | gaa | aat | 672 |
| Val | Thr | Gly | Ala | Asp | Ile | Leu | Gln | Ala | Ile | Val | Gln | Ser | Lys | Glu | Asn | |
| | 210 | | | | | 215 | | | | | 220 | | | | | |

| | | | | | | | | | | | | | | | | |
|---|---|---|---|---|---|---|---|---|---|---|---|---|---|---|---|---|
| cct | gtt | gca | aat | agt | act | gat | gga | att | gaa | aaa | gca | aca | gat | gca | gct | 720 |
| Pro | Val | Ala | Asn | Ser | Thr | Asp | Gly | Ile | Glu | Lys | Ala | Thr | Asp | Ala | Ala | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gag | att | gca | gtt | gct | cca | gct | aaa | gat | aat | aaa | aaa | gag | att | aaa | gat | 768 |
| Glu | Ile | Ala | Val | Ala | Pro | Ala | Lys | Asp | Asn | Lys | Lys | Glu | Ile | Lys | Asp | |
| | | | | 245 | | | | | 250 | | | | | 255 | | |

| | | | | | | | | | | | | | | | | |
|---|---|---|---|---|---|---|---|---|---|---|---|---|---|---|---|---|
| gga | gca | aaa | aaa | gac | gca | gtt | att | gct | gca | ggc | att | gca | ctg | cga | gca | 816 |
| Gly | Ala | Lys | Lys | Asp | Ala | Val | Ile | Ala | Ala | Gly | Ile | Ala | Leu | Arg | Ala | |
| | | | 260 | | | | | 265 | | | | | 270 | | | |

| | | | | | | | | | | | | | | | | |
|---|---|---|---|---|---|---|---|---|---|---|---|---|---|---|---|---|
| atg | gct | aag | aat | ggt | aca | ttt | tct | att | aaa | aac | aat | gaa | gat | gcg | gct | 864 |
| Met | Ala | Lys | Asn | Gly | Thr | Phe | Ser | Ile | Lys | Asn | Asn | Glu | Asp | Ala | Ala | |
| | | 275 | | | | | 280 | | | | | 285 | | | | |

| | | | | | | | | | | | | | | | | |
|---|---|---|---|---|---|---|---|---|---|---|---|---|---|---|---|---|
| gta | acg | acg | ata | aat | agt | gca | gca | gca | agc | gca | gtg | aac | aag | att | tta | 912 |
| Val | Thr | Thr | Ile | Asn | Ser | Ala | Ala | Ala | Ser | Ala | Val | Asn | Lys | Ile | Leu | |
| | 290 | | | | | 295 | | | | | 300 | | | | | |

```
agc act cta ata ata gca ata agg aat aca gtt gat agt ggt tta aaa      960
Ser Thr Leu Ile Ile Ala Ile Arg Asn Thr Val Asp Ser Gly Leu Lys
305                 310                 315                 320 aca ata aat gag gct ctt gct aca gtt aaa caa gaa gat aaa tct gta     1008
Thr Ile Asn Glu Ala Leu Ala Thr Val Lys Gln Glu Asp Lys Ser Val
                325                 330                 335 gaa gca act aat act gca gaa gca aca act agt ggt cag caa gcg aaa     1056
Glu Ala Thr Asn Thr Ala Glu Ala Thr Thr Ser Gly Gln Gln Ala Lys
            340                 345                 350 aac tag ttaagggtaa atataaagga taaagttatt gtaagggaaa agcttttctt      1112
Asn gtttttaatg caggaatgta gtttctctg                                     1141

<210> SEQ ID NO 50
<211> LENGTH: 353
<212> TYPE: PRT
<213> ORGANISM: Borrelia hermsii

<400> SEQUENCE: 50

Met Arg Lys Arg Ile Ser Ala Ile Ile Met Thr Leu Phe Met Val Leu
 1               5                  10                  15

Val Ser Cys Asn Ser Gly Gly Val Ala Glu Asp Pro Lys Thr Val Tyr
                20                  25                  30

Leu Thr Ser Ile Ala Asn Leu Gly Lys Gly Phe Leu Asp Val Phe Val
            35                  40                  45

Thr Phe Gly Asp Met Val Thr Gly Ala Phe Gly Ile Lys Ala Asp Thr
        50                  55                  60

Lys Lys Ser Asp Ile Gly Lys Tyr Phe Thr Asp Ile Glu Ser Thr Met
65                  70                  75                  80

Thr Ser Val Lys Lys Leu Gln Asp Glu Val Ala Lys Asn Gly Asn
                85                  90                  95

Tyr Pro Lys Val Lys Thr Ala Val Asp Glu Phe Val Ala Ile Leu Gly
                100                 105                 110

Lys Ile Glu Lys Gly Ala Lys Glu Ser Lys Gly Ala Thr Gly Asp
            115                 120                 125

Val Ile Ile Gly Asn Thr Val Lys Asn Gly Asp Ala Val Pro Gly Glu
130                 135                 140

Ala Thr Ser Val Asn Ser Leu Val Lys Gly Ile Lys Glu Ile Val Gly
145                 150                 155                 160

Val Val Leu Lys Glu Gly Lys Ala Asp Ala Asp Ala Thr Lys Asp Asp
                165                 170                 175

Ser Lys Lys Asp Ile Gly Lys Leu Phe Thr Ala Thr Asp Ala Asn
            180                 185                 190

Arg Ala Asp Asn Ala Ala Gln Ala Ala Ala Ser Ile Gly Ala
        195                 200                 205

Val Thr Gly Ala Asp Ile Leu Gln Ala Ile Val Gln Ser Lys Glu Asn
        210                 215                 220

Pro Val Ala Asn Ser Thr Asp Gly Ile Glu Ala Thr Asp Ala Ala
225                 230                 235                 240

Glu Ile Ala Val Ala Pro Ala Lys Asp Asn Lys Lys Glu Ile Lys Asp
                245                 250                 255

Gly Ala Lys Lys Asp Ala Val Ile Ala Ala Gly Ile Ala Leu Arg Ala
            260                 265                 270

Met Ala Lys Asn Gly Thr Phe Ser Ile Lys Asn Asn Glu Asp Ala Ala
        275                 280                 285
```

-continued

```
Val Thr Thr Ile Asn Ser Ala Ala Ala Ser Ala Val Asn Lys Ile Leu
    290                 295                 300
Ser Thr Leu Ile Ile Ala Ile Arg Asn Thr Val Asp Ser Gly Leu Lys
305                 310                 315                 320
Thr Ile Asn Glu Ala Leu Ala Thr Val Lys Gln Glu Asp Lys Ser Val
                325                 330                 335
Glu Ala Thr Asn Thr Ala Glu Ala Thr Thr Ser Gly Gln Gln Ala Lys
                340                 345                 350
Asn
```